United States Patent
Champlin et al.

(10) Patent No.: US 10,061,972 B2
(45) Date of Patent: Aug. 28, 2018

(54) IMAGE ANALYSIS SYSTEMS AND RELATED METHODS

(71) Applicant: Tokitae LLC, Bellevue, WA (US)

(72) Inventors: Cary Richard Champlin, Bellevue, WA (US); Charles Delahunt, Seattle, WA (US); Matthew P. Horning, Redmond, WA (US); Liming Hu, Kent, WA (US); Shawn Keith McGuire, Seattle, WA (US); Courosh Mehanian, Redmond, WA (US); Clay Matthew Thompson, Camano Island, WA (US); Benjamin K. Wilson, Kirkland, WA (US)

(73) Assignee: TOKITAE LLC, Bellevue, WA (US)

(*) Notice: Subject to any disclaimer, the term of this patent is extended or adjusted under 35 U.S.C. 154(b) by 0 days.

(21) Appl. No.: 15/433,656

(22) Filed: Feb. 15, 2017

(65) Prior Publication Data

US 2017/0161545 A1 Jun. 8, 2017

Related U.S. Application Data

(63) Continuation-in-part of application No. 15/154,824, filed on May 13, 2016, now Pat. No. 9,836,839.

(60) Provisional application No. 62/167,452, filed on May 28, 2015.

(51) Int. Cl.
| | |
|---|---|
| *G06K 9/00* | (2006.01) |
| *G06K 9/46* | (2006.01) |
| *G01N 33/49* | (2006.01) |
| *G06T 7/00* | (2017.01) |
| *G02B 21/36* | (2006.01) |

(52) U.S. Cl.
CPC .......... *G06K 9/0014* (2013.01); *G01N 33/49* (2013.01); *G06K 9/00147* (2013.01); *G06K 9/4652* (2013.01); *G06T 7/0012* (2013.01); *G02B 21/365* (2013.01); *G06T 2207/10024* (2013.01); *G06T 2207/30004* (2013.01)

(58) Field of Classification Search
None
See application file for complete search history.

(56) References Cited

U.S. PATENT DOCUMENTS

| | | |
|---|---|---|
| 6,172,349 B1 | 1/2001 | Katz et al. |
| 7,706,606 B1 | 4/2010 | Ruzon et al. |
| 8,103,102 B2 | 1/2012 | Chien et al. |

(Continued)

FOREIGN PATENT DOCUMENTS

WO 2015007697 1/2015

OTHER PUBLICATIONS

PCT International Search Report; International App. No. PCT/US2016/034050; Sep. 19, 2016; pp. 1-3.
(Continued)

*Primary Examiner* — Atiba O Fitzpatrick
(74) *Attorney, Agent, or Firm* — Dorsey & Whitney LLP

(57) ABSTRACT

Embodiments disclosed herein are directed to systems and methods for determining a presence and an amount of an analyte in a biological sample. The systems and methods for determining the presence of an analyte utilize a plurality of images of a sample slide including multiple fields-of-view having multiple focal planes therein. The systems and methods utilize algorithms configured to balance the color and grayscale intensity of the plurality of images and based thereon determine if the plurality of images contain the analyte therein.

48 Claims, 22 Drawing Sheets

(56) References Cited

U.S. PATENT DOCUMENTS

| | | | |
|---|---|---|---|
| 8,326,084 | B1 | 12/2012 | Marrion, Jr. et al. |
| 8,760,756 | B2 | 6/2014 | Price et al. |
| 8,768,065 | B2 | 7/2014 | Melikian |
| 2004/0126008 | A1 | 7/2004 | Chapoulaud et al. |
| 2012/0002871 | A1 | 1/2012 | Hu et al. |
| 2012/0194729 | A1 | 8/2012 | Zahniser |
| 2012/0207360 | A1 | 8/2012 | Mehanian et al. |
| 2013/0100272 | A1 | 4/2013 | Price et al. |
| 2013/0267032 | A1 | 10/2013 | Tsai et al. |
| 2013/0279789 | A1 | 10/2013 | Elter et al. |
| 2015/0186755 | A1 | 7/2015 | Mehanian et al. |
| 2015/0211987 | A1 | 7/2015 | Burg et al. |

OTHER PUBLICATIONS

Harvey et al.; "Comparison of GENIE and Conventional Supervised Classifiers for Multispectral Image Feature Extraction"; IEEE Transactions on Geoscience and Remote Sensing; Feb. 2002; pp. 393-404; vol. 40, No. 2.

Krizhevsky et al.; "ImageNet Classification with Deep Convolutional Neural Networks"; 2012; pp. 1-9; last accessed on May 19, 2016.

Linder et al.; "A Malaria Diagnostic Tool Based on Computer Vision Screening and Visualization of Plasmodium falciparum Candidate Areas in Digitized Blood Smears" PLOS ONE, www.Qlosone om, Aug. 2014, vol. 9, Issue 8.

Tek et al., "Computer vision for microscopy diagnosis of malaria" Malaria Journal 2009, 8:153, http://www.rnalariajoumal.corn/contentJ8/i !153 (14 pages).

Wikipedia; Author Unknown; Comparison Chromatic Focus Shift Pits, Apochromat, (2 pages) retrieved on May 13, 2016. httgs://en.wikigeclia.orq/wiki/AQochrornat.

PCT International Search Report; International App. No. PCT/US2018/018113; dated May 29, 2018; pp. 1-3.

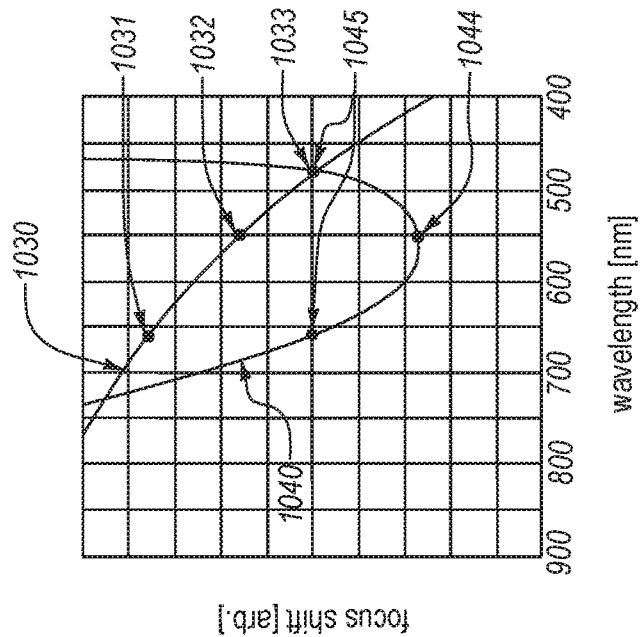
FIG. 10C
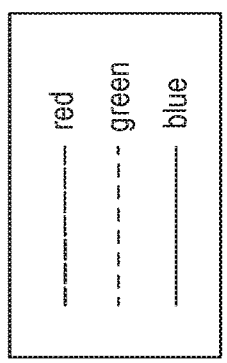 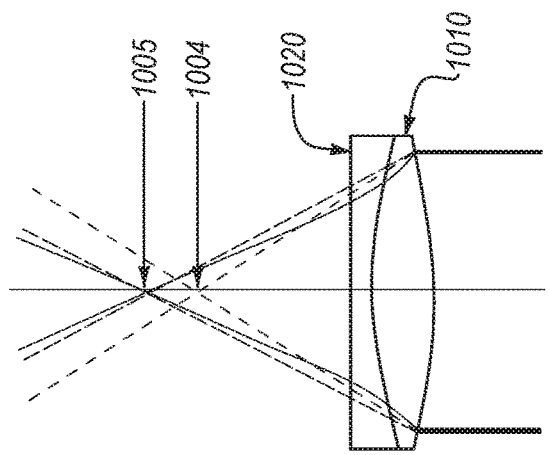
FIG. 10B
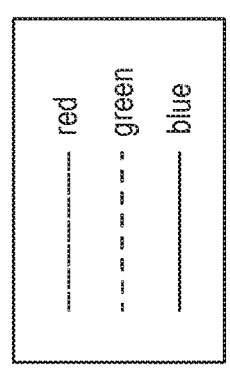 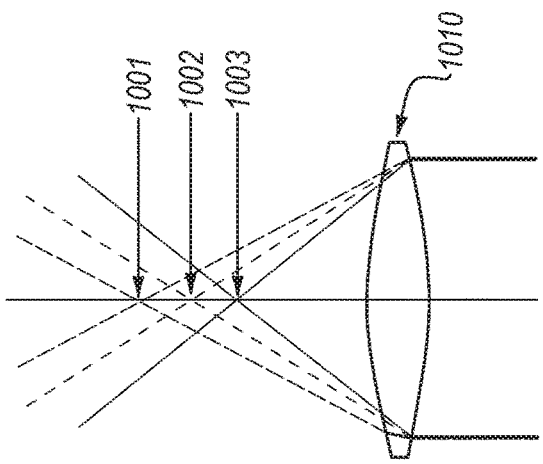
FIG. 10A

IMAGE ANALYSIS SYSTEMS AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc., applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 U.S.C. § 119(e) for provisional patent applications, for any and all parent, grandparent, great-grandparent, etc. applications of the Priority Application(s)).

A. Priority Applications

For purposes of the USPTO extra-statutory requirements, the present application constitutes a continuation-in-part of U.S. patent application Ser. No. 15/154,824, entitled IMAGE ANALYSIS SYSTEMS AND RELATED METHODS, filed May 13, 2016, which is currently co-pending or is an application of which a currently co-pending application is entitled to the benefit of the filing date, which constitutes a non-provisional application of U.S. Provisional Patent Application No. 62/167,452, entitled AUTOMATED MICROSCOPY AND MACHINE LEARING FOR EXPERT-LEVEL MALARIA FIELD DIAGNOSIS, filed May 28, 2015, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Microscopy techniques are used to diagnosis several diseases, hematology conditions, etc. Some microscopy techniques require specialized microscopes or other equipment to achieve sufficient resolution for proper diagnoses.

Microscopes can be used to detect analytes such as malaria using a smear, such as a thick blood smear. Typically, the microscope includes an oil immersion lens having a relatively shallow depth of field to achieve resolutions required to detect the parasitic protozoans that cause malaria. The lens typically exhibits a depth of field that is only a few micrometers, about a micrometer, or less than a micrometer. Typically, an entire thickness of a smear is imaged to conclusively diagnose a condition indicated by the presence of the analyte. However, the thickness of the smear is greater than a few micrometers, which can cause problems with diagnosis, depending on the focal plane of the image. To ensure that the entire smear is analyzed, the distance between the sample and the lens can be decreased or increased to capture multiple focal planes of each field-of-view (FoV) in a smear.

A typical microscope includes a conventional focusing system configured to increase or decrease a distance between the lens and the sample in micrometer displacements. However, such a conventional focusing system can be expensive and complex, which makes the conventional focusing systems unsuitable for areas where is malaria is most prevalent, such as in poverty-stricken areas. Typical diagnostic measures include employing a human technician to scan the slide in the microscope to visually determine if the analyte is present. However, factors that limit the sensitivity and consistency of human microscopists include inter- and intra-person variability, inattentiveness, eyestrain, fatigue, and lack of training. Lack of training is especially relevant in low-resource settings, where highly-qualified microscopists can be in short supply compared to the burden of diseases such as malaria. Additionally, human technicians may not be able to identify or quantify particularly low concentrations of an analyte (e.g., low parasitemia) in a sample slide.

Therefore, developers and users of microscopes continue to seek improvements to microscopes and diagnostic techniques for use in determining a presence of analytes.

SUMMARY

Embodiments disclosed herein relate to systems and methods for diagnosing identifying, and quantifying biological analytes in biological samples. In an embodiment, a system for determining the presence of an analyte in blood is disclosed. The system includes at least one memory storage medium configured to store a plurality of images of a sample slide. The plurality of images include a plurality of fields-of-view, each including a unique x and y coordinate of the sample slide; and a plurality of focal planes, each having a unique z coordinate of the sample slide. The system includes at least one processor operably coupled to the at least one memory storage medium. The at least one processor is configured to determine and apply a white balance transform to each of the plurality of images effective to produce a plurality of color-corrected images. The at least one processor is configured to determine and apply an adaptive grayscale transform to each of the plurality of images to provide an adaptive grayscale intensity image for each of the plurality of images. The at least one processor is configured to detect and identify one or more candidate objects in the plurality of color-corrected images and the adaptive grayscale intensity images. The at least one processor is configured to extract and score the one or more candidate objects based at least in part on one or more characteristics of the one or more candidate objects, filter the one or more candidate objects based at least in part on the score, and output one or more color-corrected image patches and one or more adaptive grayscale intensity image patches for each filtered candidate object. The at least one processor is configured to extract one or more feature vectors from the color-corrected image patches and the adaptive grayscale intensity image patches and output the one or more feature vectors. The at least one processor is configured to classify each feature vector as corresponding to an artifact or an analyte. The at least one processor is configured to determine if the feature vectors classified as analytes are above or below a threshold level associated with a positive diagnosis.

In an embodiment, a method of determining the presence of an analyte in blood is disclosed. The method includes receiving a plurality of images of a sample slide. The plurality of images include a plurality of fields-of-view, each including a unique x and y coordinate of the sample slide; and a plurality of focal planes, each having a unique z coordinate of the sample slide. The method includes applying a white balance transform to each of the plurality of images effective to produce a plurality of color-corrected images. The method includes applying an adaptive grayscale transform to each of the plurality of images to provide an adaptive grayscale intensity image for each of the plurality of images. The method includes detecting and identifying one or more candidate objects in the plurality of color-corrected images and the adaptive grayscale intensity images. The method includes filtering the one or more candidate objects based at least in part on a score that is based at least in part on one or more characteristics thereof and outputting one or more color-corrected image patches and one or more adaptive grayscale intensity image patches for each filtered candidate object. The method includes extracting one or more feature vectors from the color-corrected image patches and the adaptive grayscale intensity image patches and outputting the one or more feature vectors. The method includes classifying each feature vector as corresponding to an artifact or an analyte. The method includes determining if the feature vectors classified as analytes are above or below a threshold level associated with a positive diagnosis.

In an embodiment, a system for determining the presence of a malaria parasite in blood is disclosed. The system includes a microscope configured to capture a plurality of images of a blood slide. Each of the plurality of images includes a plurality of fields-of-view, each including a unique x and y coordinate of the blood slide; and a plurality of focal planes, each having a unique z coordinate of the blood slide. The system includes at least one memory storage medium configured to store the plurality of images of the blood slide. The system includes at least one processor operably coupled to the at least one memory storage medium. The at least one processor is configured to determine and apply a white balance transform to each of the plurality of images effective to produce a plurality of color-corrected images. The at least one processor is configured to determine and apply an adaptive grayscale transform to each of the plurality of images to provide an adaptive grayscale intensity image for each of the plurality of images. The at least one processor is configured to detect and identify one or more candidate objects in the plurality of color-corrected images and the adaptive grayscale intensity images. The at least one processor is configured to extract and score one or more characteristics of the one or more candidate objects, filter the one or more candidate objects based at least in part on the score. The at least one processor is configured to extract color-corrected image patches and adaptive grayscale intensity image patches of the one or more filtered candidate objects and output one or more feature vectors for each filtered candidate object. The at least one processor is configured to classify each feature vector as an artifact or an analyte. The at least one processor is configured to determine if the feature vectors classified as analytes are above or below a threshold level associated with a positive diagnosis.

In an embodiment, a system for determining a presence of an analyte in blood is disclosed. The system includes at least one memory storage medium configured to store a plurality of images of a sample slide, the plurality of images including a plurality of fields-of-view, each including a unique x and y coordinate of the sample slide; and a plurality of focal planes, each having a unique z coordinate of the sample slide. The system includes at least one processor operably coupled to the at least one memory storage medium. The at least one processor of the system is configured to determine and apply a white balance transform to each of the plurality of images effective to produce a plurality of color-corrected images. The at least one processor of the system is configured to determine and apply an adaptive grayscale transform to each of the plurality of images to provide an adaptive grayscale intensity image for each of the plurality of images. The at least one processor of the system is configured to detect and identify one or more candidate objects in color-corrected images and adaptive grayscale intensity images. The at least one processor of the system is configured to perform an adaptive thresholding operation on the adaptive grayscale intensity images and output one or more candidate objects based thereon. The at least one processor of the system is configured to cluster the one or more detected candidate objects into clusters including one or more adjacent candidate objects per cluster and associate clusters of detected candidate objects indicating that a cluster of one or more adjacent candidate objects are a single candidate object and output locations of the clusters of one or more adjacent candidate objects, the locations including one or more image patches containing the one or more adjacent candidate objects. The at least one processor of the system is configured to locate the focal plane having a best focus for each single candidate object. The at least one processor of the system is configured to determine attributes of each single candidate object in the focal plane having the best focus for each single candidate object. The at least one processor of the system is configured to filter each single candidate object based at least in part on one or more determined attributes. The at least one processor of the system is configured to extract and output one or more image patches each containing at least one filtered single candidate object of the one or more candidate objects.

In an embodiment, a method for determining a presence of an analyte in blood is disclosed. The method includes receiving a plurality of images of a sample slide, the plurality of images including, a plurality of fields-of-view, each including a unique x and y coordinate of the sample slide; and a plurality of focal planes, each having a unique z coordinate of the sample slide. The method includes applying a white balance transform to each of the plurality of images effective to produce a plurality of color-corrected images. The method includes applying an adaptive grayscale transform to each of the plurality of images to provide adaptive grayscale intensity images for each of the plurality of images. The method includes detecting and identifying one or more candidate objects in the plurality of color-corrected images and the adaptive grayscale intensity images. The detecting and identifying one or more candidate objects of the method includes performing an adaptive thresholding operation on the adaptive grayscale intensity images and outputting one or more candidate objects based thereon. The detecting and identifying one or more candidate objects of the method includes clustering the one or more detected candidate objects into clusters including one or more candidate objects per cluster and associating clusters of detected candidate objects indicating that one or more adjacent candidate objects are a single candidate object and outputting locations of the clusters of one or more adjacent candidate objects, the locations including one or more image patches containing the clusters of one or more adjacent candidate objects. The detecting and identifying one or more candidate objects of the method includes identifying the focal plane having a best focus for each single candidate object. The detecting and identifying one or more candidate objects of the method includes determining attributes of each single candidate object in the focal plane having the best focus for each single candidate object. The detecting and identifying one or more candidate objects of the method includes filtering each single candidate object based at least in part on one or more determined attributes. The detecting and identifying one or more candidate objects of the method includes extracting and outputting one or more image patches each containing at least one filtered single candidate object of the one or more candidate objects.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrate aspects, embodiments, and features described above, further aspects, embodiments, and features will become apparent by reference to the drawings and the following detailed description.

BRIEF DESCRIPTION OF THE FIGURES

FIGS. 10A and 10B are illustrations of light rays being refracted to different focal planes through a simple lens and a lens with an achromatic correction, respectively.

FIG. 10C is a graph of focus versus wavelength curves for the simple lens and lens with an achromatic correction shown in FIGS. 10A and 10B.

DETAILED DESCRIPTION

Figure 1:
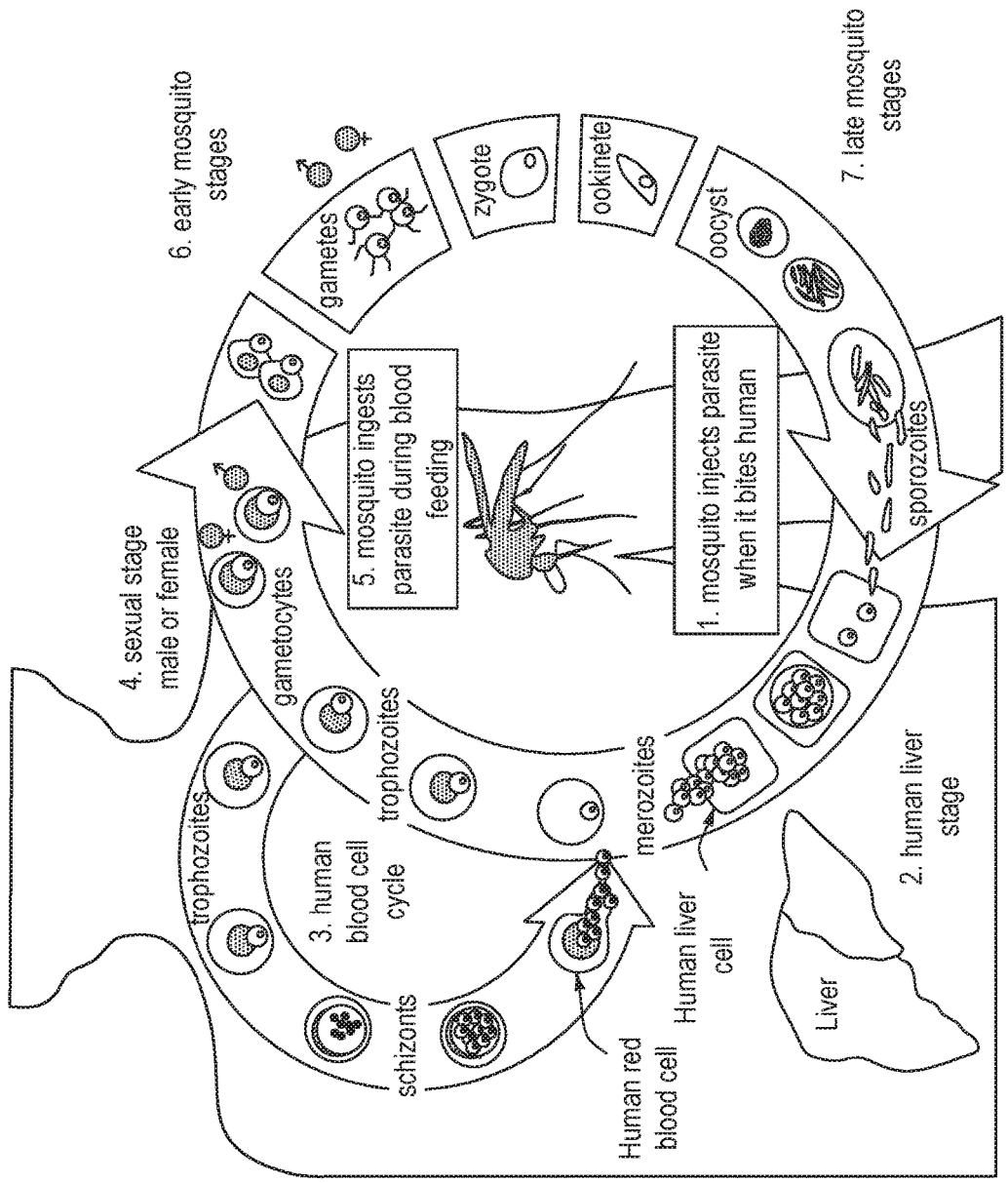
FIG. 1 is a diagram of the malaria life cycle.

Embodiments disclosed herein relate to image analysis systems, and methods of using the same. The images disclosed herein include images in any computer readable format, such as png, jpeg, gif, tiff, bmp, or any other suitable file type. The image analysis systems and related methods herein can resolve and analyze images throughout an entire vertical thickness (e.g., substantially parallel to an optical or z-axis on a microscope) and lateral sections (e.g., x and y axis based dimensions) of a sample smear (e.g., a thick blood smear) on a slide. The systems and methods herein can identify objects in different focal planes (z-levels) that are in fact the same object, but which appear different due to differing focal depth or which have different x-y coordinates due to camera jitter. As explained in more detail below, the blood smear can be analyzed using multiple fields-of-view (FoVs) defining discrete lateral (sub)sections of the blood smear and multiple focal planes defining discrete (vertically stacked) planes throughout the thickness of the blood smear. The image analysis systems herein can accurately identify a presence and, in some embodiments, species or stages of parasite(s) or other analytes in a sample. The systems and methods disclosed herein can provide one or more of automatic diagnosis and of quantification of one or more analytes in biological specimens at a performance level equal to or better than a highly-trained human microscopist. As used herein, the term "analyte" is not intended to be limited to a specific chemical species, but is intended to extend at least to one or more of parasites (e.g., malaria, etc.), blood components, or other objects in a sample for which an analysis is carried out. The systems and methods disclosed herein provide a comprehensive machine learning framework, which uses computer vision and machine learning techniques including support vector machines (SVMs) and convolutional neural networks (CNNs) to detect analytes.

The image analysis systems and related methods herein include a plurality of modules (e.g., programs or algorithms) configured to carry out different functions to accurately determine a presence of an infection or a condition in a sample even at low concentrations (e.g., low parasitemia) and without the need for human observation. The plurality of modules can include a preprocessing module, a candidate detection module, a feature extraction module, a classification module, and a diagnosis module. While described herein as individual "modules" for clarity, each of the "modules" can be one or more algorithms, or machine-readable programs based on the same, stored in at least one memory storage device and can be executable by a processor operably coupled thereto. The plurality of modules can include discrete programing modules and submodules stored in the memory storage medium of at least one controller (e.g., computer) or in one or more processors therein each having programming configured to carry out the functions of the related modules. The terms "modules" and "submodules" are used to differentiate between components and subcomponents of an algorithm or system and can be used interchangeably depending upon context. For example, a submodule can also be termed a module, such as when the submodule is discussed without respect to a parent module of the submodule.

Generally, each module is configured to cause the controller or processor to perform the functions described below. While a high level overview of the functions are described generally immediately below for ease of understanding, specific aspects of each module are disclosed in more detail below.

The image preprocessing module can generate adaptively white balanced color images and adaptive grayscale intensity images of multiple images, including multiple FoVs and a plurality of focal planes (e.g., each of the plurality of focal planes being substantially perpendicular to the optical axis) of a sample slide. The candidate detection module can identify one or more candidate objects based at least in part on one or more attributes of candidate objects in the images (e.g., intensity, color type, level of focus, or other attributes), identify and exclude one or more artifacts (e.g., non-analyte objects such as non-parasitic objects including white blood cells in the sample) based on the same, and can extract color-corrected image patches and adaptive grayscale intensity image patches containing each candidate object. The feature extraction module can identify and output one or more data sets of the candidate object(s) in the specific image (e.g., one or more vectors of a specific FoV and focal plane thereof). The feature extraction module can base said identification on manual features including one or more of best focus score of the candidate object, the standard deviation (or other measure of dispersion) of the focus score across the focal planes in a FoV, or a red-shift score. The feature extraction module can additionally or alternatively identify and output one or more images based at least in part on one or more automatic features including computer-learned characteristics (e.g., one or more vectors learned by a convolutional neural network) of positive samples, negative samples, or both. The classification module can be configured to determine if the extracted features have high probability scores (indicating that an analyte or artifact is present) based at least in part on weights learned from known positive and negative samples (e.g., including presence, type, stage, or species of a parasite) and determine an estimate of the concentration of the analyte (e.g., the parasitemia) in the sample.

The following mathematical notations will be used in the equations used in the algorithms disclosed throughout this disclosure. A lowercase or uppercase letter in italics represents a scalar value (e.g., k). A lower case letter in bold italics represents a column vector (e.g., $\xi$). An uppercase letter in bold italics represents a matrix (e.g., A). The superscript T stands for the matrix transpose, (e.g., $\xi^T$). Image plane coordinates are referred to as <x, y>, and coordinates in the vertical direction, that is, parallel to the optical axis are referred to as <z>.

The image analysis system of the present disclosure receives as input a series of images of a biological specimen acquired from a high-resolution image capture device (e.g., high-resolution microscope), and produces as output, diagnostic information about the status of the biological specimen with respect to the presence, species, and count of one or more analytes (e.g., disease agents such as parasites or naturally-occurring components such as blood components).

In an embodiment, the biological specimen includes a microscope slide of a sample (e.g., a blood smear) and the image analysis system herein analyzes one or more acquired sample slide images to determine the presence or absence of one or more analytes (e.g., malaria parasites) therein. The image analysis system herein analyzes sample slides for the presence, count, and species identification of an analyte. While the systems and methods disclosed herein are not limited to use with blood smears, the blood smear will be used throughout this disclosure as an embodiment to illustrate concepts and it should be understood that the disclosure applies to other biological samples without limitation.

In an embodiment, blood smears are stained with Giemsa stain prior to histopathological diagnosis of one or more analytes therein such as malaria. The Giemsa stain is a combination of Methylene blue, Eosin Y, and Azure B; it stains erythrocytes (red blood cells, hereinafter "RBCs") pink and leukocyte nuclei (white blood cells, hereinafter "WBCs") dark magenta. Malaria parasite nuclei will also stain magenta, although not as dark in appearance as leukocyte nuclei. Malaria parasite cytoplasm will stain light to medium blue. While the systems and methods disclosed herein are not limited to detecting malaria, malaria will be used throughout this disclosure as an example embodiment to illustrate concepts and it should be understood that the disclosure applies to other analytes without limitation. Further, other stains and methods of staining may be used which are complementary to the analyte being tested. For example, suitable stains may include a Field stain, Jaswant Singh Bhattacharya (JSB) stain, Leishman stain, etc.

In an embodiment, the systems and methods herein can be used to detect and quantify an amount of an analyte in a sample based at least in part on one or more of shape, color, or size of the analyte. In some embodiments, the analyte can have more than one conformation or appearance. The systems and methods herein can be configured to detect or quantify the one or more conformations, types, or species of analytes. As an example embodiment, human malaria parasites belong to five different species of the genus *Plasmodium: falciparum, vivax, ovale, malariae,* and *knowlesi*. Individuals of each of these species go through a complex series of stages in their life cycle. At each stage, the parasite takes on a different physical appearance, and the systems and methods herein can detect and identify parasites from each of the five different species.

FIG. 1 is a diagram of the malaria life cycle courtesy of the National Institute of Allergy and Infectious Diseases. The right side of FIG. 1 shows stages in the malaria parasite life cycle that take place within a mosquito. The left side of the figure shows the stages within an infected human. In the mosquito, malaria parasites start out as gametocytes, both male and female. The gametocytes reproduce to form gametes, which eventually develop and multiply into sporozoites. The sporozoites migrate to the mosquito salivary gland.

When the mosquito bites a human, the sporozoites enter the bloodstream and travel to the liver and infect hepatocytes (liver cells). The sporozoites multiply into merozoites, rupture liver cells of the infected host, and return to the bloodstream. Individual merozoites infect red blood cells and develop into a ring form, which is an immature trophozoite. The ring form develops into a more mature trophozoite and eventually into a schizont. Each schizont will break apart into multiple merozoites, each of which seeks its own red blood cell to infect. In this way, the asexual portion of the reproductive cycle repeats itself, indicated by the human blood cell cycle shown to the top left of FIG. 1. Some merozoites can develop into gametocytes, which if ingested by a biting mosquito, will continue the parasite life cycle.

The different species have different life cycle durations and, even at the same life cycle stage, distinctive physical appearances. Because the treatment regimens vary between malaria species, it is important to distinguish between them when doing histopathological malaria diagnosis. The systems and methods of the present disclosure can automatically differentiate between the different malaria stages or species (or analytes).

Figure 2B:
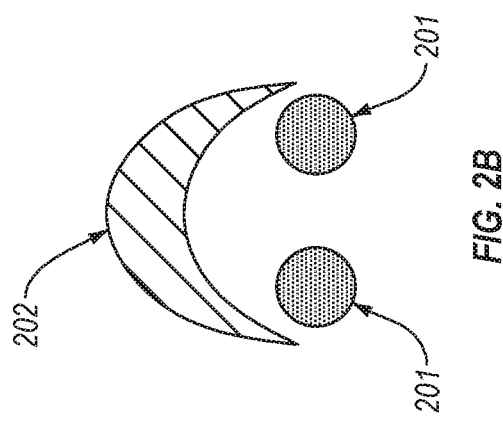
FIGS. 2A and 2B are schematics of ring-form parasites.
Figure 2A:
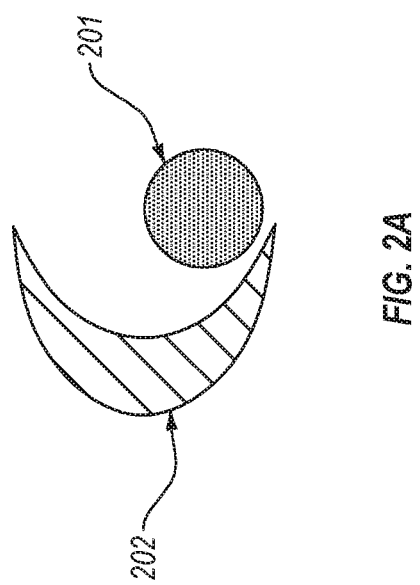

FIGS. 2A and 2B are schematics of ring-form parasites. The ring-form parasite is commonly seen in the peripheral blood. The physical appearance of ring-form parasites varies greatly. The ring-form parasite typically features one (FIG. 2A) or two (FIG. 2B) chromatin dots 201, which contain the parasite's nuclear material. The chromatin dots 201 stain magenta under Giemsa stain as noted above. The ring-form parasite also features a wispy cytoplasm 202, which stains light to medium blue under Giemsa as noted above. The chromatin dots 201 are typically about 1 µm in diameter and the entire ring form under about 3 µm in diameter. The systems and methods herein can be used to identify or quantify analytes that are about 200 nm or larger, such as about 200 nm to about 100 µm, about 500 nm to about 10 µm, about 1 µm to about 5 µm, or less than about 50 µm. In an embodiment, to obtain high-quality images of objects this small, a microscope featuring a high resolution lens is used. For example, a suitable high-resolution microscope can include an oil-immersion 100× objective with a numerical aperture greater than or equal to about 1.2. The microscope can be fitted with a digital image capture device, such as a camera. The depth-of-field of the high-magnification optical systems herein can be about 0.35 µm or less (e.g., 0.3 µm, 0.2 µm, 0.1 µm, or ranges between any of the preceding), whereas blood smears can be several times thicker than this. In embodiments, multiple focal planes are captured for each FoV to capture in-focus images of parasites that can be vertically located anywhere between the bottom and the top of the blood smear. The number of focal planes captured per FoV is designated $n_z$.

Figure 2C:
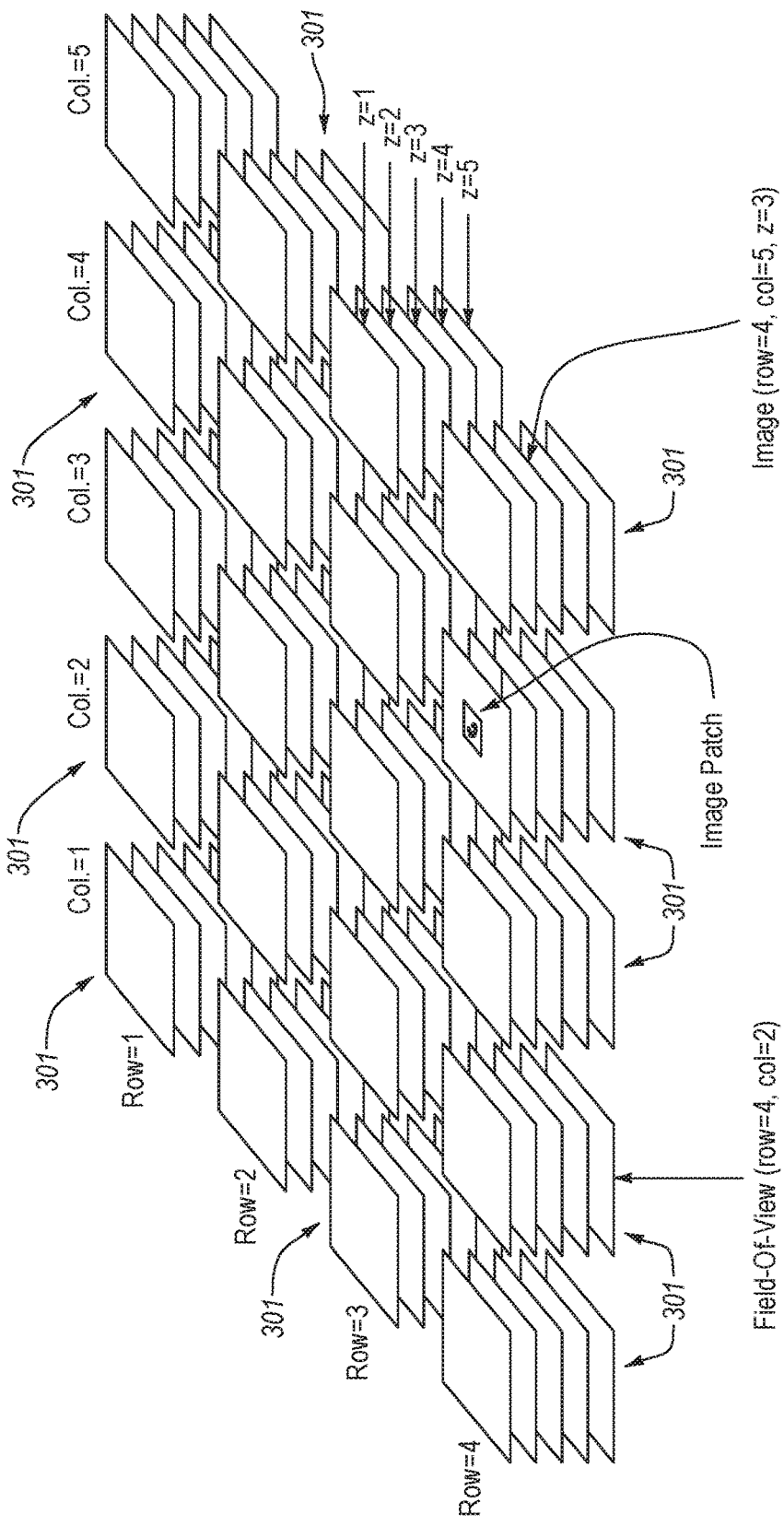
FIG. 2C is a schematic view of a plurality of images, according to an embodiment.

FIG. 2C is a schematic view of a plurality of images 301, according to an embodiment. The plurality of images 301 are arranged in multiple rows and columns. The rows and columns of images collectively define a blood smear or other sample slide. For example, a blood smear may be substantially entirely captured by a plurality of images arranged in a collection of y rows, x columns, and z focal planes. The number of captured FoVs is designated $n_{x,y}$. The lateral extent (e.g., x and y extents) of each FOV is limited by one or more the magnification of the lens or the image sensor size of the imaging device. A given size of a blood smear may require a plurality of FoVs to provide suitable image resolution for the purposes herein. Each FoV may have a plurality of focal plane images corresponding thereto. For example, an FoV corresponding to an x,y-coordinate in the plurality of images may include z focal plane images corresponding to the number of focal planes at which the images were captured at the respective FoV. That is, a particular image corresponding to an FoV can be designated by a unique x and y coordinate and the focal plane can be designated by a unique z coordinate in the FoV. Each image (e.g., specific FoV and focal plane) may contain a number of image patches therein. An image patch is a lateral subsection of an FoV (at a specific focal plane) having one or more candidate objects therein and defining an even smaller subsection of the blood slide. The systems and methods disclosed herein utilize pluralities of images including $n_{x,y}$ FoVs and $n_z$ focal planes to identify and quantify analytes in samples.

In some embodiments, the size of an FoV captured by the microscopes herein can be on the order of 10,000 µm$^2$ or more, such as 10,000 µm$^2$ to about 20,000 µm$^2$. In some embodiments, the size of an FoV captured by the microscopes herein can be less than about 10,000 µm$^2$, such as 1,000 µm$^2$ to about 10,000 µm$^2$. An FoV of about 10,000 µm$^2$ corresponds to about $3 \times 10^{-4}$ µL of blood in a thick smear blood sample. The number of parasites in an FoV of the blood smear of a malaria patient with a parasitemia of 100 parasites/µL will be Poisson distributed, having, on average, $3 \times 10^{-2}$ parasites per FoV.

In some embodiments, 300 FoVs or more can be captured to achieve sufficient statistics for a reliable detection and count of parasites at low parasitemia. For example, about 300 to 2000 FoVs can be captured or about 500 to 1000 FoVs can be captured. In some embodiments, 300 FoVs or less can be captured to achieve sufficient statistics for a reliable detection and count of parasites at low parasitemia. For example, about 10 to 300 FoVs can be captured or about 50 to 200 FoVs can be captured. The lowest detectable parasitemia level for particular analyte is called the limit-of-detection (LoD). Generally speaking, the larger the number of captured FoVs, the lower will be the LoD.

The foregoing paragraphs provide an overview of the characteristics of the images that serve as input to the image analysis system disclosed herein.

Figure 3A:
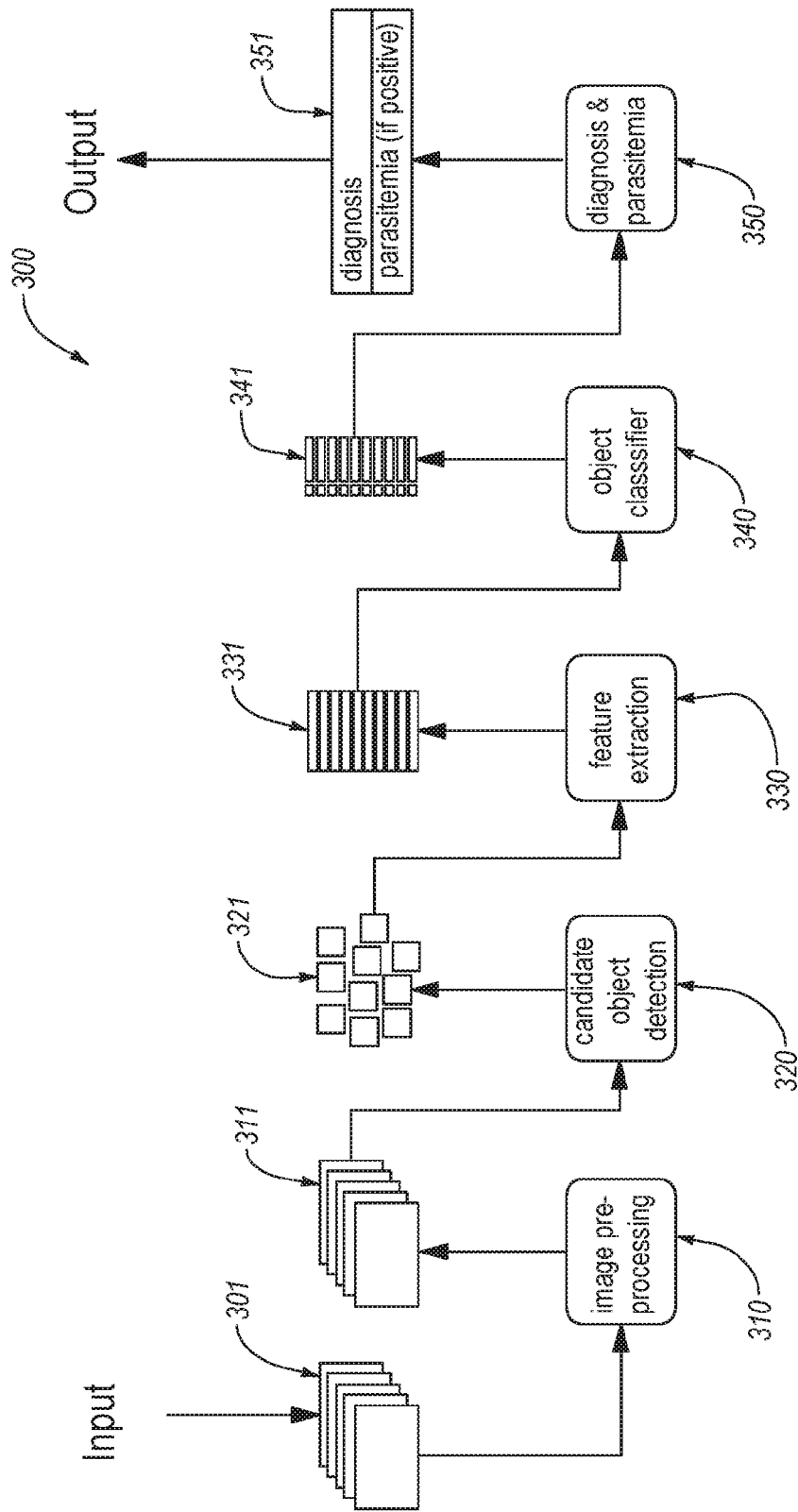
FIG. 3A is a schematic of a plurality of modules of a system to automatically detect and quantify one or more analytes in a sample, according to an embodiment.
Figure 3C:
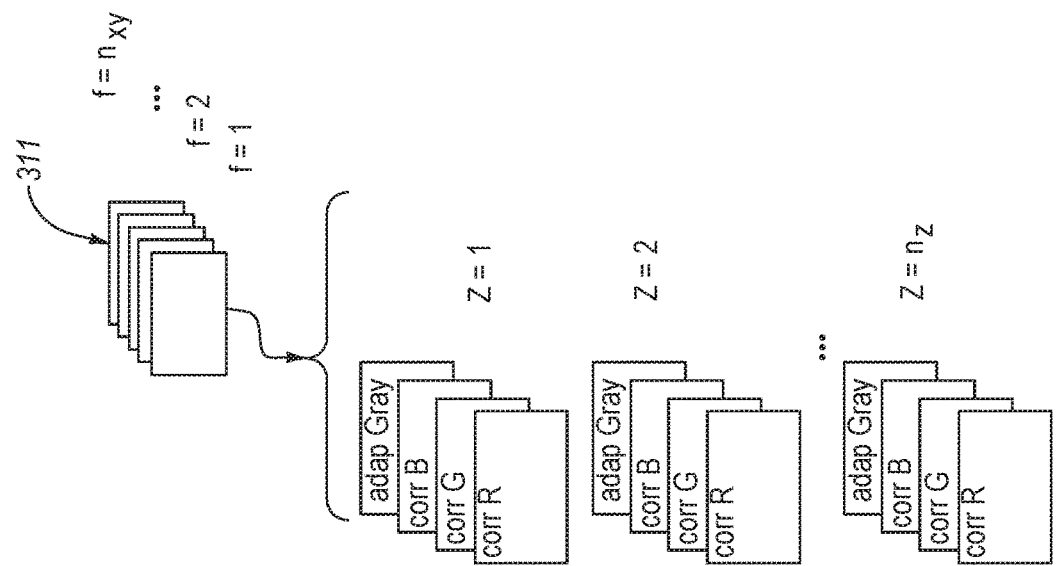
FIGS. 3B and 3C are schematics of a plurality of images input into a module of the system of FIG. 3A, according to an embodiment.
Figure 3B:
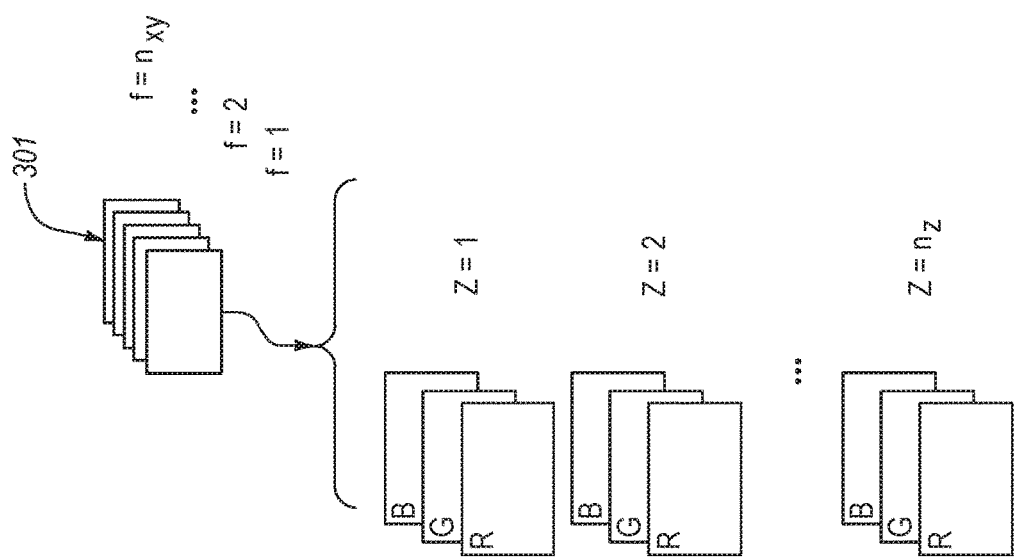

FIG. 3A is a schematic of a plurality of modules of a system 300 to automatically detect and quantify one or more analytes in a sample, according to an embodiment. The modules can be algorithms or controllers including the same (e.g., stored electronically therein) collectively configured to determine the presence of a parasite in a sample. FIGS. 3B and 3C are schematics of a plurality of images 301 input into a module of the system 300 and the output images 311 of the module, respectively.

Referring to FIG. 3A, the one or more modules include an image preprocessing module 310, a candidate object detection module 320, a feature extraction module 330, an object classifier module 340, and a diagnosis module 350. As noted above, the modules and submodules herein can refer to one or more algorithms and machine-readable programs stored in at least one memory storage device (e.g., computer hard-drive) and are executable by at least one processor operably coupled thereto. The modules and submodules described herein can likewise refer to acts in a method of automatically detecting and quantifying one or more analytes in a sample.

An input 301 into the system can include one or more FoV images of a sample slide. There are $n_{x,y}$ FoVs each of which includes $n_z$ focal planes, with each focal plane including a red, green, and blue channel images (as shown in FIG. 3B).

In the embodiment shown in FIG. 3A, the system 300 can receive as input the plurality of images 301 at the image pre-processing module 310. The plurality of images 301 can include a plurality of FoVs and a plurality of focal planes for each FoV. The image pre-processing module 310 can output a plurality of output images 311, including color-corrected images and adaptive grayscale intensity images. The plurality of color-corrected images and adaptive grayscale intensity images can be received as input at the candidate object detection module 320 and the feature extraction module 330. The candidate object detection module 320 receives the color-corrected images and adaptive grayscale intensity images and outputs color-corrected R, G, B image patches 321 containing the candidate objects and all $n_z$ focal planes thereof. The feature extraction module 330 receives as input the color-corrected R, G, B image patches 321 (based upon the plurality of color-corrected images and adaptive grayscale intensity images in the output images 311). The feature extraction module 330 extracts and outputs feature vectors 331 of the candidate objects in the color-corrected R, G, B image patches 321, and adaptive grayscale intensity image patches. A feature vector is multidimensional vector of numerical features that represent an object. In other terms, a feature vector is a vector representation including one or more variables that describe one or more characteristics (e.g., color, size, position, etc.) of the object. The object classifier 340 receives the feature vectors 331 as input and outputs classified object data 341 corresponding to the classification of each candidate object as an analyte or artifact. The classified object data is received as input at the diagnosis module 350, which determines and provides a diagnosis for the sample. The diagnosis module can output a diagnosis 351 and a relative concentration of the analyte (e.g., parasitemia). Each of the image analysis system modules 310, 320, 330, 340, and 350 are described in detail below.

A. Image Preprocessing Module

Microscope slides that are histologically stained (e.g., with Giemsa stain) typically display color variation within a slide (intra-slide) and between slides from different specimens (inter-slide). This color variation can result from differences in the pH of the stain and the duration of the staining procedure. Uncorrected, these color differences can degrade the performance of an image analysis system whose purpose is to detect and classify objects of interest in the images.

White balancing techniques can be used to standardize colors in an image. A white balance technique can compute a linear color transform as follows. The average color of the brightest pixels in an image is computed and represented as a red-green-blue column vector:

$$\bar{\xi} \stackrel{def}{=} \begin{bmatrix} \bar{R} \\ \bar{G} \\ \bar{B} \end{bmatrix} = \frac{1}{N} \sum \begin{bmatrix} R \\ G \\ B \end{bmatrix}$$

where R, G, B are the red, green, and blue channel pixel values respectively. The sum is taken over the brightest pixels, and N is the number of pixels included in the sum.

A diagonal transformation matrix A is computed as follows:

$$A = \begin{bmatrix} 1/\bar{R} & 0 & 0 \\ 0 & 1/\bar{G} & 0 \\ 0 & 0 & 1/\bar{B} \end{bmatrix}$$

The color-corrected value $\xi'$ of a pixel $$\xi \stackrel{def}{=} [R \ G \ B]^T$$

is obtained through the linear transformation defined by equation 1:

$$\xi' \stackrel{def}{=} \begin{bmatrix} R' \\ G' \\ B' \end{bmatrix} = k \cdot (A\xi + b) \quad \text{Eq. 1}$$

where b is chosen so that the color-corrected pixel values are within the range [0, k]; k is usually chosen to be 1 or 255. From this point forward in the present disclosure, the primes $\xi'$ and R', G', B' will be dropped in favor of $\xi$ and R, G, B for simplicity of notation, with the understanding that the color-corrected values are intended.

As noted above, in some embodiments, on the order of at least 300 FoVs can be captured for each blood sample. Not all of these images will contain white portions and, thus, white balancing every individual FoV image can lead to color distortion. To remedy this problem, it is possible to determine the white balance transform by separately acquiring one or more image(s) on a white portion of the microscope slide. This, however, introduces an extra scanning step into the workflow.

The systems and methods herein avoid color distortion introduced by forcing every FoV to be white balanced according to its own brightest pixels. The systems and methods herein also circumvent the need to additionally scan a clear region of the slide as an extra step.

Figure 4:
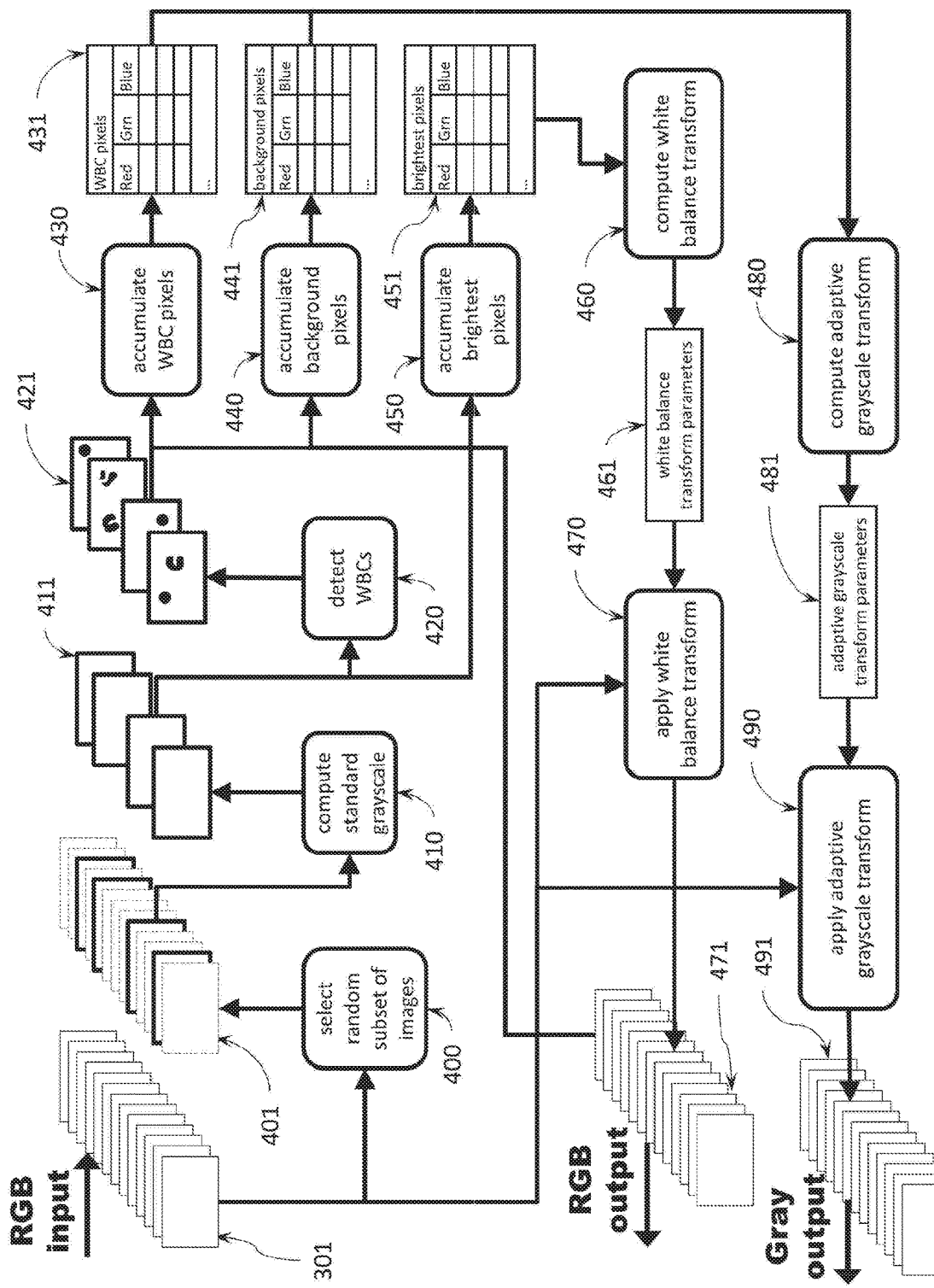
FIG. 4 is a detailed schematic of an image preprocessing module of the system of FIG. 3A, according to an embodiment.

The image preprocessing module 310 in FIG. 3A can be configured to determine the white balance transform for a sample by accumulating the brightest pixels across multiple FoVs. FIG. 4 shows a block diagram of the image preprocessing module 310. In an embodiment, a subset 401 of the totality of input FoV images 301 are selected at random at submodule 400. The number of FoVs in the subset of FoV images 401 is large enough so that the probability of including a clear region in the collection of pixels approaches one. The subset of FoV images 401 are converted to standard grayscale intensity images 411 by submodule 410 using a weighted sum of the color-corrected red, green, and blue channel pixel values defined by the formula in equation 2:

$$\phi_s = 0.299R + 0.587G + 0.114B \quad \text{Eq. 2}$$

where $\phi_s$ is the standard grayscale intensity value of a pixel.

Using the grayscale intensity values; the red, green, and blue values of a sampling of the brightest pixels 451 in the subset 411 are selected by submodule 450 and stored in a data store (e.g., memory storage medium). Submodule 460 computes the white balance transform 461 from stored red, green, and blue color values from each of the sampling of brightest pixels 451. The white balance transform parameters 461 can be saved in the data store. Submodule 470 applies the white balance transform to the input images 301 to produce the color-corrected FoV images 471. The white balance transform algorithm and its associated parameters are described in detail herein.

The image preprocessing module allows for a general affine matrix for the transformation matrix in Eq. 1.

$$A = \begin{bmatrix} a_{11} & a_{12} & a_{13} \\ a_{21} & a_{22} & a_{23} \\ a_{31} & a_{32} & a_{33} \end{bmatrix}$$

In an embodiment, the affine matrix A is a rotation matrix (also noted as A).

Figure 5:
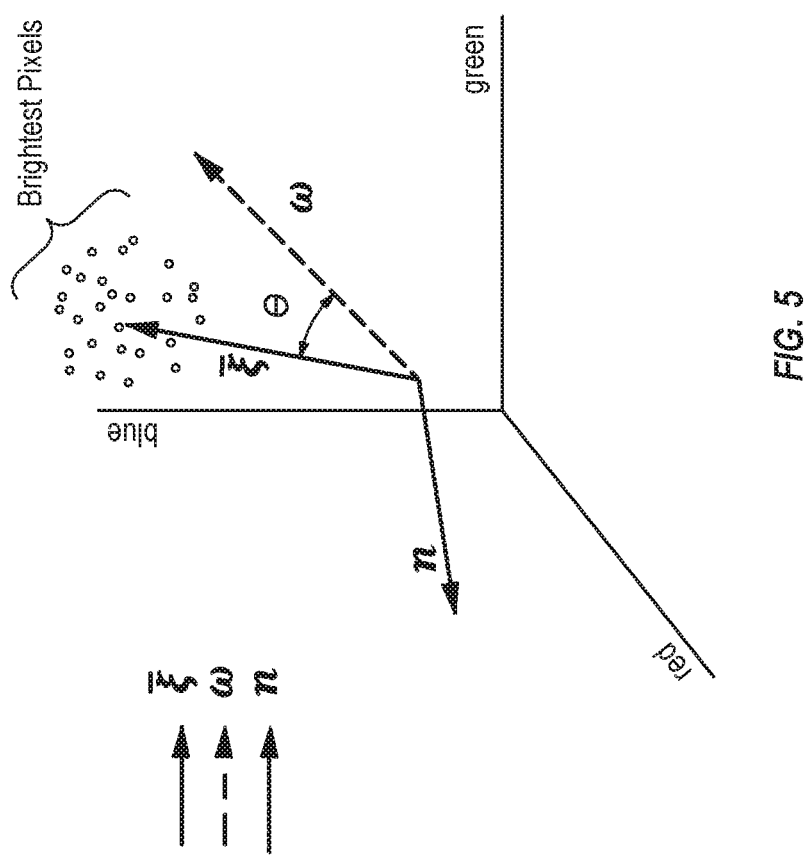
FIG. 5 is an illustration of the relationship between various vectors in a color value space of red, green and blue axes, according to an embodiment.

As stated above, the vector $\bar{\xi}$ is the average color of the sampling of brightest pixels 451. These pixels are shown in the red, green, blue pixel value space in FIG. 5. The color white is represented by the white vector $\omega=[k\ k\ k]^T$. The white balance transformation is defined by the rotation that rotates the vector $\bar{\xi}$ to the vector $\omega$ about an axis vector n that is perpendicular to both the white vector to and average color vector $\bar{\Xi}$. FIG. 5 is an illustration of the relationship between vectors $\bar{\xi}$, $\omega$, and n in a color value space of red, green and blue axes. The axis of rotation vector n can be computed by the system using the cross product:

$$n = \bar{\xi} \times \omega = \begin{bmatrix} \omega_2 \bar{B} - \omega_3 \bar{G} \\ \omega_3 \bar{R} - \omega_1 \bar{B} \\ \omega_1 \bar{G} - \omega_2 \bar{R} \end{bmatrix}$$

The rotation matrix A can be computed by the system using equation 3 below:

$$A = \begin{bmatrix} \hat{n}_1\hat{n}_1(1-\cos\theta)+\cos\theta & \hat{n}_1\hat{n}_2(1-\cos\theta)+\hat{n}_3\cos\theta & \hat{n}_1\hat{n}_3(1-\cos\theta)+\hat{n}_2\sin\theta \\ \hat{n}_2\hat{n}_1(1-\cos\theta)+\hat{n}_3\sin\theta & \hat{n}_2\hat{n}_2(1-\cos\theta)+\cos\theta & \hat{n}_2\hat{n}_3(1-\cos\theta)-\hat{n}_1\sin\theta \\ \hat{n}_3\hat{n}_1(1-\cos\theta)-\hat{n}_2\sin\theta & \hat{n}_3\hat{n}_2(1-\cos\theta)-\hat{n}_1\sin\theta & \hat{n}_3\hat{n}_3(1-\cos\theta)+\cos\theta \end{bmatrix} \qquad \text{Eq. 3}$$

In equation 3, $\hat{n}=n/\|n\|$ is a unit vector in the direction of the axis of rotation n, where $\|\cdot\|$ denotes the standard $L^2$ norm. The cosine of the angle $\theta$ between the vectors $\bar{\xi}$ and $\omega$ can be computed via the dot product $\cos\theta=\hat{\omega}^T\hat{\xi}$, where $\hat{\omega}=\omega/\|\omega\|$ and $\hat{\xi}=\bar{\xi}/\|\bar{\xi}\|$.

Referring again to FIG. 3A, the image preprocessing module 310 can compensate for color variation in input images 301 as outlined above and outputs a plurality of output images 311 including color-corrected FoV images and adaptive grayscale intensity images, each including one or more focal planes therein. The next stage in the processing pipeline of the image analysis system 300 is the candidate object detection module 320. The candidate object detection module 320 is configured to find image locations that could potentially be analytes (e.g., malaria parasites). In order to find such potential analyte locations, the candidate object detection module 320 can use a plurality of adaptive grayscale transform images and a plurality of color-corrected (e.g., white balance transformed) images in the plurality of output images 311. The plurality of output images 311 including the plurality of adaptive grayscale transform images and plurality of color-corrected images can be determined and output by the image preprocessing module 310.

The candidate parasite nuclei can be detected by applying a dark threshold to a standard grayscale intensity image, which is calculated via the weighted sum shown in Eq. 2. This weighted sum can be viewed as a projection in the red, green, and blue pixel space that was introduced previously and shown in FIG. 5. The projection is in the direction of the vector defined by equation 4:

$$w_s = \begin{bmatrix} 0.299 \\ 0.587 \\ 0.114 \end{bmatrix} \qquad \text{Eq. 4}$$

Representing the red, green, and blue values of a pixel as the column vector $\xi$, the grayscale projection in Eq. 2 can be written $\phi_s = w_s^T \xi$. To detect candidate parasite nuclei, a dark threshold can be applied to the standard grayscale intensity image intensity $\phi_s$ of each pixel, followed by one or more of area, color, and shape filters that may be applied to the blobs (e.g., candidate object clusters) detected by applying the dark threshold. The standard dark threshold is a filter that functions based at least in part on a determined difference between the grayscale intensity of each pixel of the candidate object and the grayscale intensity of the background or other non-analyte pixels present in the sample. Accordingly, the standard dark threshold can be used to filter (select or delete) pixels that are not beyond (e.g., above) the darkness threshold.

Figure 6:
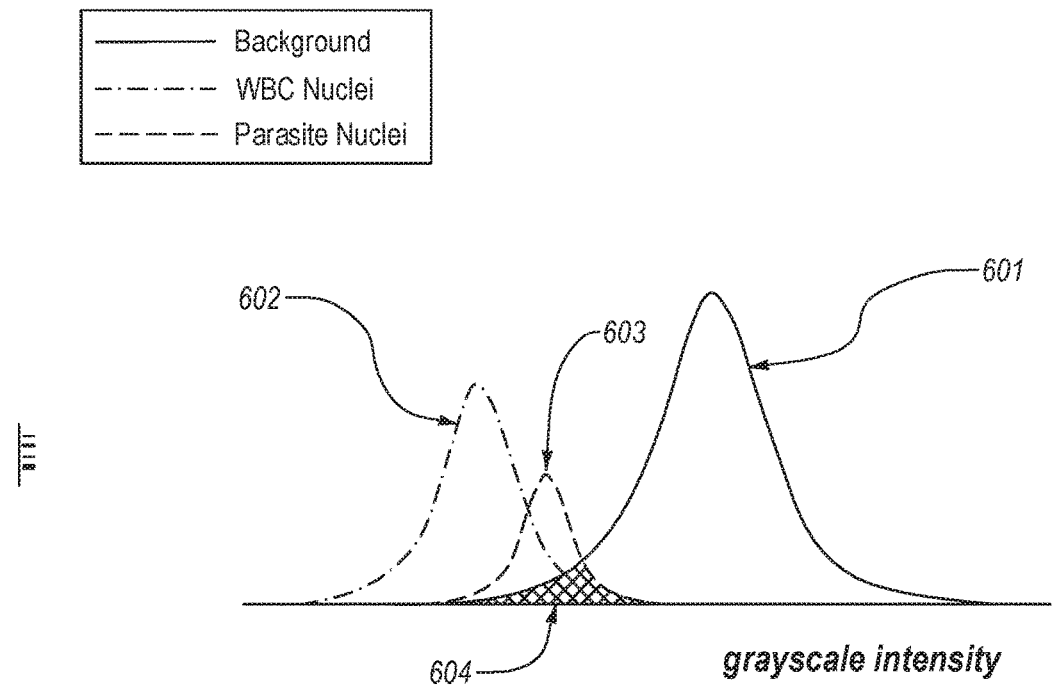
FIGS. 6A and 6B are grayscale intensity histograms for various pixels of various grayscale images, according to different embodiments.
Figure 6:
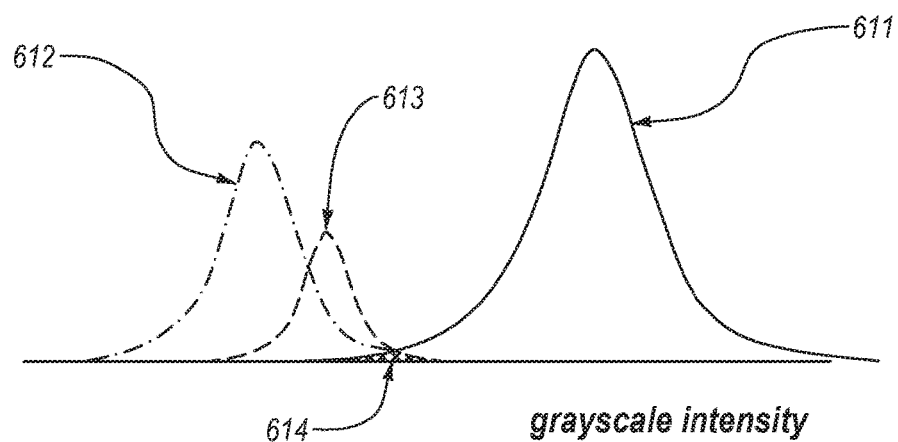

The sensitivity and specificity performance of the above noted technique for detecting candidate parasite nuclei is limited. Despite the general trend that parasite nuclei are dark and the background is light, there is a great deal of overlap between the parasite nuclei and background grayscale pixel values. FIG. 6A shows the grayscale intensity histograms for the background pixels 601, WBC nuclei pixels 602, and parasite nuclei pixels 603. The overlap between the parasite nuclei and background grayscale intensity values is shown as the cross-hatched area 604 in FIG. 6A.

Minimizing the overlap between the parasite nuclei and background grayscale intensity values enhances the sensitivity and specificity performance of the detection algorithm herein. The systems and methods herein determine (e.g., learn) and apply an adaptive grayscale projection vector $w_a$ that takes the place of the standard grayscale projection vector $w_s$ defined in Eq. 4. Such determination can be accomplished using machine learning techniques. Such application can provide a greater separation of grayscale intensity values corresponding to white blood cell nuclei pixels and analyte (e.g., malaria parasite) pixels from grayscale intensity values corresponding to background pixels.

The minimization of overlap disclosed herein leverages the presence of blood components that are simple to detect in the standard grayscale intensity image and which stain similarly to parasite nuclear material.

Under Giemsa stain, a ring-form parasite's nuclear material stains magenta as noted above. In particular, the nuclear material is, in general, darker than the surrounding background material, which consists of red blood cell (RBC) material that has been lysed by the action of the water used in the Giemsa staining process as well as other blood components such as platelets. This background material can stain a broad spectrum of colors from light pink to medium blue. In addition to parasites (if the blood is so infected), lysed RBCs, and platelets; WBCs are a ubiquitous presence in blood smears. As noted above, WBC nuclei stain dark magenta under Giemsa, the same color as parasite nuclear material, albeit stained WBC nuclei are, for the most part, darker than stained parasite nuclei as they are larger and absorb more light. WBC nuclei are relatively easy to detect and classify as they are large, regularly shaped, and dark magenta in color. Accordingly, in some embodiments, the WBC nuclei can serve as an easily detectable analog for a parasite nuclei. The systems and methods herein apply a dark threshold to the standard grayscale intensity images, followed by one or more of an area, color, or shape filter to obtain WBC nuclei at sufficiently high sensitivity and specificity.

Referring again to the schematic of the image preprocessing module in FIG. 4, WBC detector submodule 420 is applied to the subset of grayscale FoV images 411 using the straightforward WBC detection algorithm outlined above, thereby producing a series of binary images 421 that indicate which image pixels are part of WBC nuclei. Submodule 430 accumulates a random sample of the R, G, B values of the detected WBC nuclei pixels 431 and stores them in a data store. Pixels that are not part of WBCs are categorized as potential background pixels. Dark pixels are excluded from background pixels to avoid pollution of the background pixels with either parasite nuclei pixels (which are not detected by the WBC detector because they are too small) or pixels from dark regions that correspond to staining artifacts (e.g., RBCs, platelets, etc.). The systems and methods herein can include submodule 440 which can accumulate a random sample of the qualified background pixels 441 store the same in a data store.

The WBC nuclei pixel values 431 and the background pixel values 441 can be used by a machine learning algorithm (or module) to determine an adaptive grayscale projection vector $w_a$ (in the red, green, blue pixel value space) that optimizes the separation between WBC nuclei and background. In an embodiment, a ridge regression technique can be used (e.g., by at least one processor as stored in at least one memory storage medium) to learn the optimal vector $w_a$. In some embodiments, a design matrix X can be constructed by stacking the red, green, and blue values for the WBC nuclei and background pixels such as according to the following matrix:

$$X = \begin{bmatrix} R_1 & G_1 & B_1 \\ \cdots & & \\ R_N & G_N & B_N \\ R_{N+1} & G_{N+1} & B_{N+1} \\ \cdots & & \\ R_{N+M} & G_{N+M} & B_{N+M} \end{bmatrix} \begin{matrix} \} \ N \ WBC \ \text{nuclei pixel values} \\ \\ \} \ M \ \text{backround pixel values} \end{matrix}$$

where N is the number of WBC nuclei pixels and M is the number of background pixels accumulated. A corresponding target variable η vector can be constructed as N ones stacked on top of M zeros such as according to the following matrix:

$$\eta = \begin{bmatrix} 1 \\ \cdots \\ 1 \\ 0 \\ \cdots \\ 0 \end{bmatrix} \begin{matrix} \} \ WBC \ \text{nuclei} \\ \\ \} \ \text{background} \end{matrix}$$

In some embodiments, a ridge regression aims to find the vector $w_a$ that minimizes the following $L^2$-regularized optimization problem having the formula defined by equation 5 below:

$$w_a = \text{Arg Min}_w \|Xw - \eta\|^2 + C\|w\|^2 \qquad \text{Eq. 5}$$

where C is a suitably chosen regularization constant. The methods and systems herein can use the adaptive grayscale direction vector $w_a$ is to compute an adaptive grayscale intensity $\phi_a$ via the projection having the formula $\phi_a = w_a^T \xi$.

As shown in FIG. 6B, the use of the adaptive grayscale intensity image in place of the standard grayscale intensity image results in a greater separation between WBC nuclei and background grayscale intensity values than the separation found in standard grayscale intensity images, and hence also between parasite nuclei and background grayscale intensity values. The grayscale intensity histograms for the background pixels 611, WBC nuclei pixels 612, and parasite nuclei pixels 613 for the adaptive grayscale intensity image are shown in FIG. 6B, where it can be seen that the overlap area 614 is substantially reduced compared to the overlap area 604 in FIG. 6A which was determined using the standard grayscale intensity images.

In some embodiments, a polynomial regression can be used instead of a linear regression as describe above. The polynomial regression is an extension of linear regression and permits a non-linear relationship between the target variable η vector and the predictor variable(s) (e.g., $\xi$). For example, polynomial regression can be used by the methods and systems herein to find a linear relationship between the target variable η and the second order polynomial predictor variable $\zeta$. In one embodiment, a second order polynomial predictor variable $\zeta$ can be defined by equation 6 below.

$$\zeta = [R \ G \ B \ R^2 \ G^2 \ B^2 \ RG \ RB \ GB]^T \qquad \text{Eq. 6}$$

In some embodiments, higher order polynomials can be incorporated into regressions used to determine the adaptive grayscale intensity, to provide adaptive grayscale intensity images. This concept can be further generalized to include predictor variable components that are rational functions of the R, G, and B values. In one embodiment, a 24-component predictor variable $\zeta$ can be used to determine an adaptive gray scale intensity to provide adaptive grayscale intensity images having greater separation of intensity values between background pixels and WBC and analyte pixels. In an embodiment, the 24-component predictor variable $\zeta$ can have the formula defined by equation 7 below:

Eq. 7
$$= \begin{bmatrix} R & G & B & R^2 & G^2 & B^2 & RG & RB & GB & \dfrac{R}{G+\in} & \dfrac{R}{B+\in} & \dfrac{G}{R+\in} & \dfrac{G}{B+\in} & \dfrac{B}{R+\in} & \dfrac{B}{G+\in} & \cdots \\ \dfrac{R}{G+B+\in} & \dfrac{G}{R+B+\in} & \dfrac{B}{R+G+\in} & \dfrac{R}{R+G+B+\in} & \dfrac{G}{R+G+B+\in} & \dfrac{B}{R+G+B+\in} & \dfrac{R+G}{R+G+B+\in} & \dfrac{G+B}{R+G+B+\in} & \dfrac{R+B}{R+G+B+\in} \end{bmatrix}^T$$

where $\in$ is a suitably chosen constant to prevent the denominator of the ratios from vanishing. In other embodiments, other non-linear functions of the R, G, and B components are used. Introduction of a non-linear relationship between the target and predictor variables serves to further enhance the separation between parasite nuclei pixels and background pixels in the adaptive grayscale intensity images. Some form of regularization is used for the regression computations disclosed above. Regularization serves to offset the negative consequences of multicollinearity between components of the predictor variable ζ. In various embodiments, the regularized regression technique is chosen from among the following: ridge regression, lasso regression, principal components regression, and partial least-squares regression.

Referring again to FIG. 4, submodule 480 computes a regression model between the predictor variables ξ or ζ, and the target variable η. The parameters of the regression model 481 can be stored in the data store and used by submodule 490, along with the input images 301, to compute the adaptive grayscale intensity images 491. The color-corrected images 471 along with the adaptive grayscale intensity images 491 are the output images 311 (FIGS. 3A and 3C) of the image preprocessing module 310. The output images 311 include $n_{xy}$ FoVs, each including $n_z$ focal planes, each focal plane including the color-corrected red, green, and blue component image(s) as well as adaptive grayscale intensity image(s), as shown in FIG. 3C.

Figure 7:
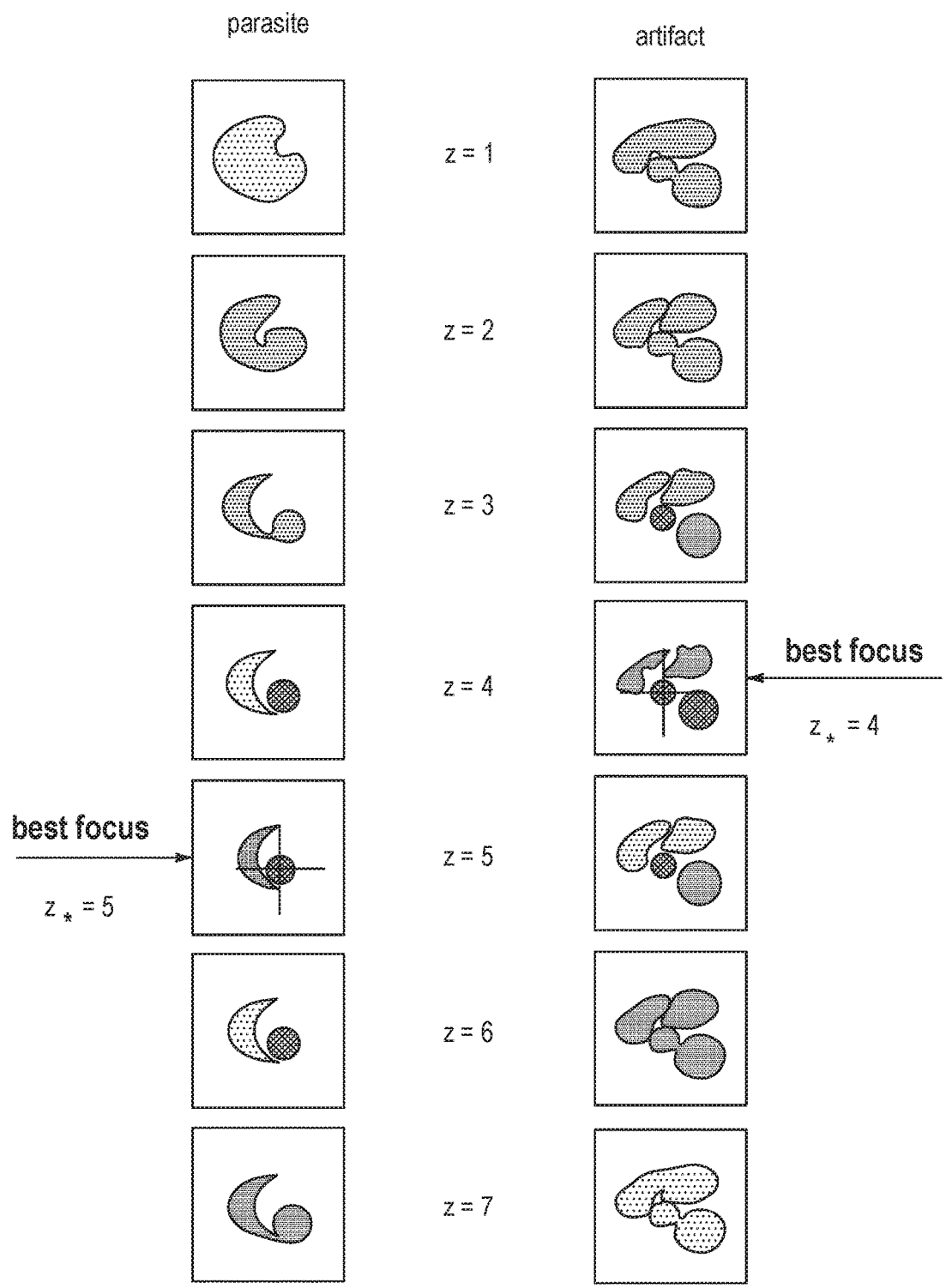
FIG. 7 is a side-by-side comparison of images of different FoVs having multiple focal planes, where one FoV includes a parasite and the other FoV includes an artifact therein, according to an embodiment.

As noted previously, a parasite located in an FoV can be in best focus in any one of the $n_z$ focal planes that are captured. FIG. 7 is a side-by-side comparison of FoVs having multiple focal planes, one FoV includes an analyte (e.g., parasite) and the other FoV includes an artifact (e.g., platelet) therein. The image analysis systems herein are configured to examine all the focal planes for every input FoV to find potential parasite locations. The appearance of a parasite will be different in each focal plane image. Each FoV can include 1 or more focal planes such as 1, 2, 3, 4, 5, 6, 7, 8, 9, or more than 9 focal planes. The left column of FIG. 7 shows a small section of an FoV containing a parasite in an embodiment with $n_z$=7 focal planes (e.g., seven different focal planes). In some embodiments, one or more clusters of pixels indicating a candidate object (e.g., blob(s)) can be detected in one or more focal planes in the vicinity of a parasite, such as by applying a threshold on the adaptive grayscale intensity images for each of the focal planes. In this same manner, candidate objects can be detected in the vicinity of artifacts that are darker than the background, for example in the vicinity of platelets. The right column of FIG. 7 shows a small section of an FoV containing a candidate object that is not a parasite, but rather an artifact (e.g., it can be a platelet or stain aggregate).

B. Candidate Object Detection Module

Figure 8A:
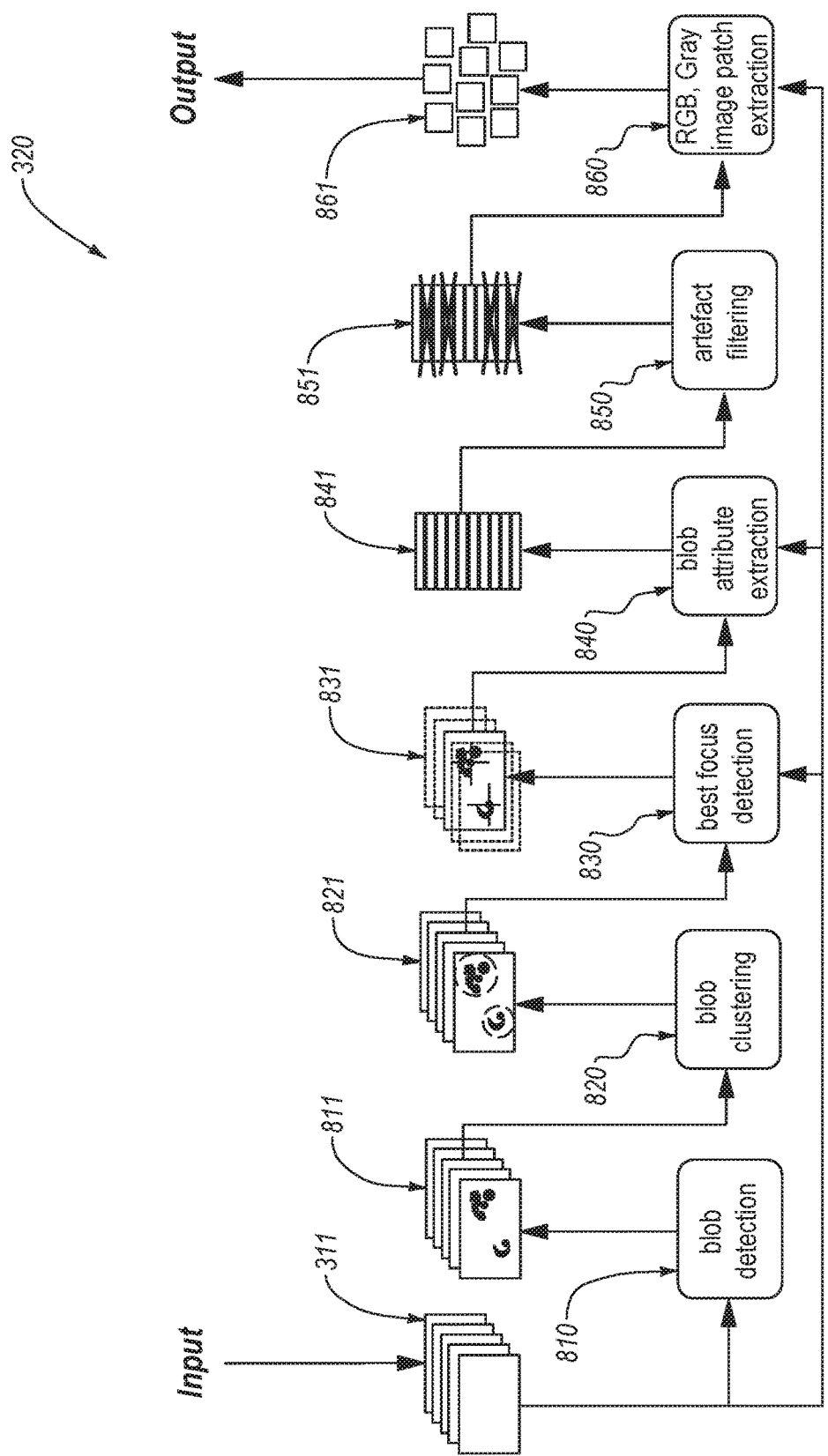
FIG. 8A is a detailed schematic of a candidate object detection module of the system of FIG. 3A, according to an embodiment.

FIG. 8A is a schematic of the candidate object detection module 320 also shown in FIG. 3A. The output images 311 (e.g., set of color-corrected RGB and adaptive gray images) are input to the candidate object detection module 310. The candidate object detection module 310 can include a plurality of submodules each configured as described below.

The submodule 810 can perform a thresholding operation on the adaptive gray images and output one or more detection masks 811. The submodule 820 can be configured to associate detected clusters of pixels indicating a candidate object (referred to hereinafter as "blobs") that are close to each other (in the <x, y> image coordinates) as part of one candidate object and output the locations of the object clusters 821. The submodule 830 can be configured to find the plane of best focus 831 for each candidate object or a portion thereof by determining the focal plane with the highest focus score for an image patch (e.g., subsection of an FoV having a candidate object therein) containing the detected candidate object. The submodule 830 can determine, select, and output the focal plane(s) with the highest focus score 831 for each candidate object. In an embodiment, a Brenner score can be used to find the plane of best focus 831, which is denoted by $z_*$. Other focus scores can be used in other embodiments. In the embodiment shown in FIG. 7, $z_*$=5 is the best focal plane for the candidate object (parasite) in the left column therein. The best focal plane for the candidate object (artifact) in the right column of FIG. 7 is $z_*$=4. Submodule 830 also identifies the darkest blob in the best focal plane and considers (e.g., determines, assumes, or at least temporarily assigns) that this blob represents the candidate object of interest. In another embodiment, the roundest blob is assigned to represent the candidate object of interest. A rounder blob may more closely correspond to a malaria parasite or portion thereof such as a cytoplasm or nuclei. In various embodiments, other attributes or combinations of attributes are used to select the representative blob. The blob centers are marked by a cross-hair in both columns of FIG. 7, $z_*$=5 and $z_*$=4, respectively.

Referring to FIG. 8A, submodule 840 is configured to determine (e.g., compute) attributes 841 of the main blob for each candidate object. Attributes such as area, roundness, grayscale intensity, etc. are computed by submodule 840. Submodule 850 can be configured to filter the candidate objects based at least in part on at least in part on the determined attributes. Filtering the candidate objects based at least in part on the determined attributes reduces the number of artifacts in the collection of candidate objects as indicated at 851. Submodule 850 can be configured as or include an artifact classifier configured to score the candidate objects based at least in part on one or more attributes. The submodule 850 can be configured to determine a score for a candidate object based on one or more of any of the determined attributes disclosed herein, such as scores relating to probability that the candidate object is an analyte based at least in part on one or more characteristics (intensity, color, shape, size, etc.) of the one or more candidate objects. The submodule 850 can be configured to discard candidate objects with a score below a threshold score.

The artifact classifier of submodule 850 can be pre-trained with images of objects whose ground truth identity (as an analyte or non-analyte) are known through an annotation process, whereby parasites are marked in advance by a human expert. The annotation process stores the <x, y> location and best focal plane <z> of a large number of parasites. Candidate objects that are close to the known parasite locations are considered to represent parasites. Candidate objects that are not close to a known parasite location are considered to represent artifacts. The attributes and ground truth class of known parasites and artifacts are used to pre-train the artifact classifier 850. In one embodiment, the artifact classifier is configured as a non-linear kernel SVM. In other embodiments, other classifiers are used. Submodule 860 can be configured to extract and output image patches 861 of the filtered candidate objects. The image patches 861 are small sections of the color-corrected RGB images and the adaptive grayscale intensity images that contain a candidate object. These image patches 861 (321 in FIG. 3A) are output to the feature extraction module, which is shown as block 330 in FIG. 3A.

Additional aspects of the candidate object detection module are disclosed below with respect to (FIGS. 8B-8G). For example, the systems and methods of the present disclosure may be used to detect objects that are very small and comprise a negligible fraction of the total pixels in an image (e.g., 10% or less, 5% or less, or 2% or less). The systems and methods of the present disclosure can compute a spatially varying/adaptive threshold (for grayscale intensity) that avoids false positive detections in high noise regions by riding the noise floor, and that responds to low noise regions by lowering the grayscale intensity threshold to achieve maximum sensitivity in low noise regions. The systems and methods disclosed herein do not rely on the presence of large dark objects such as WBCs (or bright objects) from which to infer a reasonable threshold; while at the same time taking into account known large dark objects such as WBCs (or bright objects) in order to avoid having them distort the computation of the spatially varying noise floor. Additional aspects of the candidate object detection module are disclosed below with respect to (FIGS. 8B-8G).

Figure 8B:
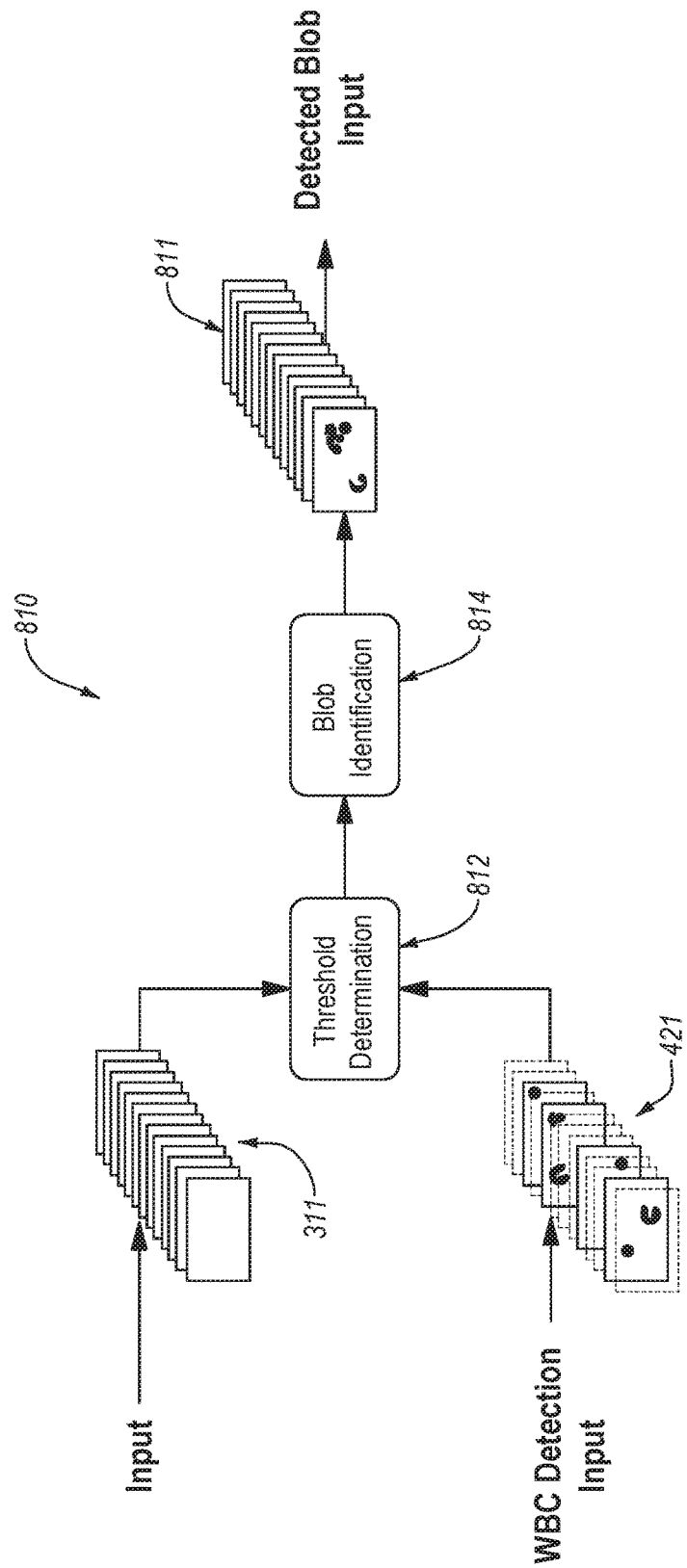
FIG. 8B is a schematic of a blob detection submodule of the candidate object detection module of FIGS. 3A and 8A, according to an embodiment.

FIG. 8B is a schematic of a blob detection submodule 810 of the candidate object detection module 320 of FIGS. 3A and 8A. The blob detection submodule 810 can receive as inputs the one or more output images 311 (e.g., adaptive grayscale intensity images from the image preprocessing module 310); and the one or more binary images 421 (e.g., from the image preprocessing module 310), such as WBC detection input(s) (e.g., masks). The adaptive gray scale intensity images of the output images 311 and the binary images 421 are received by the threshold determination submodule 812 of the blob detection submodule 810. The threshold determination submodule 812 can output an adaptive grayscale (intensity) threshold for each image patch and/or FOV of an image, based upon a number of operations performed on the adaptive gray scale intensity images and binary images 421. The adaptive grayscale (intensity) threshold(s) that are output from the threshold determination submodule 812 can aid in determining if a blob is a candidate object, a WBC, background, or any other aspect of an image. The adaptive grayscale intensity threshold(s) are then applied by blob identification submodule 814 to detect and locate the blobs (e.g., candidate object clusters) which are output from the blob identification submodule 814 as one or more (candidate object) detection masks 811.

The typical background of a grayscale intensity image or portion thereof (e.g., FoV or image patch) can include stain and other noise (e.g., artefacts such as platelets, partially-lysed or un-lysed red blood cells, stain aggregates, and the like). Candidate parasite nuclei (e.g., candidate objects) are generally darker than the background in the images from stained slides. Thus, they can be detected by applying a darkness threshold to a grayscale intensity image or, equivalently, by applying a brightness threshold to an inverted grayscale intensity image. These darkness and/or brightness thresholds can be expressed as a grayscale intensity threshold. Throughout this disclosure, the convention of an inverted grayscale intensity image can be adopted. Therefore, a bright threshold can applied to the inverted grayscale intensity image(s) to detect potential parasite locations.

The value of the grayscale intensity threshold may be critical to the detection sensitivity achieved by an image analysis system or technique. However, a single grayscale intensity threshold for an entire image, FOV, and/or image patch, can lead to false positives and missed parasites (e.g., parasites that are not easily distinguishable from the background). Such false positives and/or missed parasites can be due to local variation(s) in characteristics and content of the image(s), FoVs, or images patches (e.g., variations in one or more of color or grayscale intensity of the background, or presence of WBC and/or RBCs).

A local grayscale (intensity) threshold having a selected value can effectively divide image pixels into one of two classes; pixels with a grayscale intensity at or below the threshold or pixels with grayscale intensity above the threshold. Depending on whether or not the brightness of the image has been inverted, a grayscale intensity at, below, or above the threshold can indicate that a pixel is either part of the background or a candidate object. Further, when WBCs are factored into the calculation of the overall grayscale intensity of an image or FoV, the calculated grayscale intensity threshold can be too dark or too bright to provide a reliable candidate object detection, especially at low population levels of the target parasite.

In the image analysis applications and systems disclosed herein, high noise regions may benefit from a high grayscale intensity threshold in order to avoid false positives that may be triggered by the artefacts in the region. Whereas, low noise regions may benefit from a low grayscale intensity threshold (e.g., lower than the high grayscale intensity threshold) to provide a relatively higher sensitivity to candidate objects (e.g., parasites). A single global threshold applied to all FoVs or image patches for an image may be a compromise between the conflicting demands of the high noise and low noise regions in the image. The single global threshold applied to an image, FOV, or image patch may cause some false positives and missed candidate objects (e.g., parasites) due to the loss of local sensitivity around candidate objects and artifacts.

Some thresholding techniques assume a bimodal distribution of pixels in an FoV or image patch, such as a class or population above a threshold and a class or population below the threshold, and calculate a threshold based on the bimodal populations. Such techniques may minimize the weighted average of the within-class grayscale intensity variances or, equivalently, maximize the between-class difference of the mean grayscale intensities (hereinafter "Simple Bimodal Techniques"), but are inaccurate compared to the techniques disclosed herein when the parasites being detected make up a small portion of the image (e.g., less than 10%, less than 5%, less than 2%, less than 1%, or less than 0.5%). For example, such Simple Bimodal Techniques are based on relatively balanced image content (e.g., a relatively close split of two classes of pixels, such as 70%:30% to 50%:50% or even 80%:20%) lose accuracy or fail to identify objects when the objects to be detected represent a small fraction of the total population of pixels in the image (e.g., less than 10%, less than 5%, less than 2%, less than 1%, or less than 0.5%). This loss of accuracy may occur when small malaria parasites (compared to WBCs), which may make up a relatively small fraction of a blood sample, are to be detected in a grayscale intensity image of a blood smear.

Some thresholding techniques can model each class of bimodal classes of pixels, respectively at or below the threshold or above the threshold, with a Gaussian distribution whose proportion, mean, and variance are computed from the pixels in the class (hereinafter "Gaussian Bimodal Techniques"). Such Gaussian Bimodal Techniques may select a threshold that minimizes the error between the modeled distributions and an empirical grayscale intensity distribution computed from the grayscale intensity image itself. However, Gaussian Bimodal Techniques still fail to identify a grayscale intensity threshold that separates objects from background when the imbalance of classes is extreme, such as when one class only comprises less than 10%, less than 5%, less than 2%, less than 1%, or less than 0.5% of the total pixels, as may be the case of malaria parasites on blood smear images. In instances when a WBC and parasite appear in the same FoV, the Gaussian Bimodal Techniques may calculate a reasonable threshold if the populations therein are relatively balanced. However, Gaussian Bimodal Techniques rely on the presence of WBCs to provide some of the pixels in a class, and WBCs do not appear and cannot be depended upon to appear, in every image, FoV, or image patch. Accordingly, thresholds determined by Gaussian Bimodal Techniques may not be reliable.

Both of the afore-mentioned thresholding techniques (Simple and Gaussian Bimodal Techniques) only compute a single, constant grayscale intensity threshold for the entire FoV. In many FoVs, there may be both regions dense with artifacts (high noise floor) and regions with very few artefacts (low noise floor). The word "noise" in this context is used to indicate image elements that are not of interest (e.g., artefacts such as platelets, partially-lysed or un-lysed red blood cells, stain aggregates and the like). The noise may also be called the background in the present disclosure. This is somewhat the reverse of most image processing applications where the word "noise" refers to small unwanted elements in the image (e.g. dropout pixels) and the aim is to reduce the noise and preserve the background. The "noise floor" may be a local median grayscale intensity value (discounting WBCs) for a window, image patch, or FoV as explained in more detail below.

The systems and methods disclosed herein both determine a grayscale intensity threshold for one or more windows, image patches, or regions in each FoV, and do so without incorporating pixel information or characteristics of objects that are not of interest (e.g., WBCs) into the determination. For example, adaptive grayscale intensity thresholds (e.g., individual and unique grayscale intensity thresholds for each of multiple image patches (e.g., regions) of an FoV) are determined by substituting grayscale intensity values of WBC pixels with a replacement median grayscale intensity value which can be median or average grayscale intensity of pixels from across the adaptive grayscale intensity image (e.g., a random sampling having a large enough population to ensure accuracy of the average grayscale intensity of the pixels). Following such a substitution, the adaptive grayscale intensity threshold is calculated using the median grayscale intensity of pixels from across the window, including the replacement medial grayscale intensity values used in the place of the values of pixels of WBCs. The local adaptive threshold can include the local median grayscale intensity value(s) as calculated in each window, or can include some value deviating therefrom by a selected amount (e.g., a value 10% brighter or darker than the local median grayscale intensity value). Computation of the local median grayscale intensity values and local adaptive thresholds base thereon is further described below.

FIG. 8B is a schematic of a blob detection submodule of the candidate object detection module of FIGS. 3A and 8A, according to an embodiment. The threshold determination submodule 812 shown in FIG. 8B can compute an accurate local threshold of local median grayscale intensity values (which may vary between windows, FoVs, and/or image patches) even when the objects to be detected represent a miniscule fraction of the pixels in the image (e.g., 10% or less, 5% or less, 2% or less, 1% or less, or 0.5% or less). The threshold determination submodule 812 does not rely on the presence of WBCs in an FoV to compute an accurate or effective threshold. Neither does the presence of WBCs in an FoV throw off threshold determinations as disclosed herein (e.g., threshold determination computations). The threshold determination submodule 812 computes a spatially varying threshold (e.g., local adaptive threshold), choosing a high threshold in high noise regions, thereby avoiding high false positive rates in these regions, while at the same time choosing a low threshold in low noise regions, thereby achieving high sensitivity in those regions as well. The threshold determination submodule 812 can compute a spatially varying (e.g., local adaptive) threshold by locally estimating the noise floor.

Figure 8C:
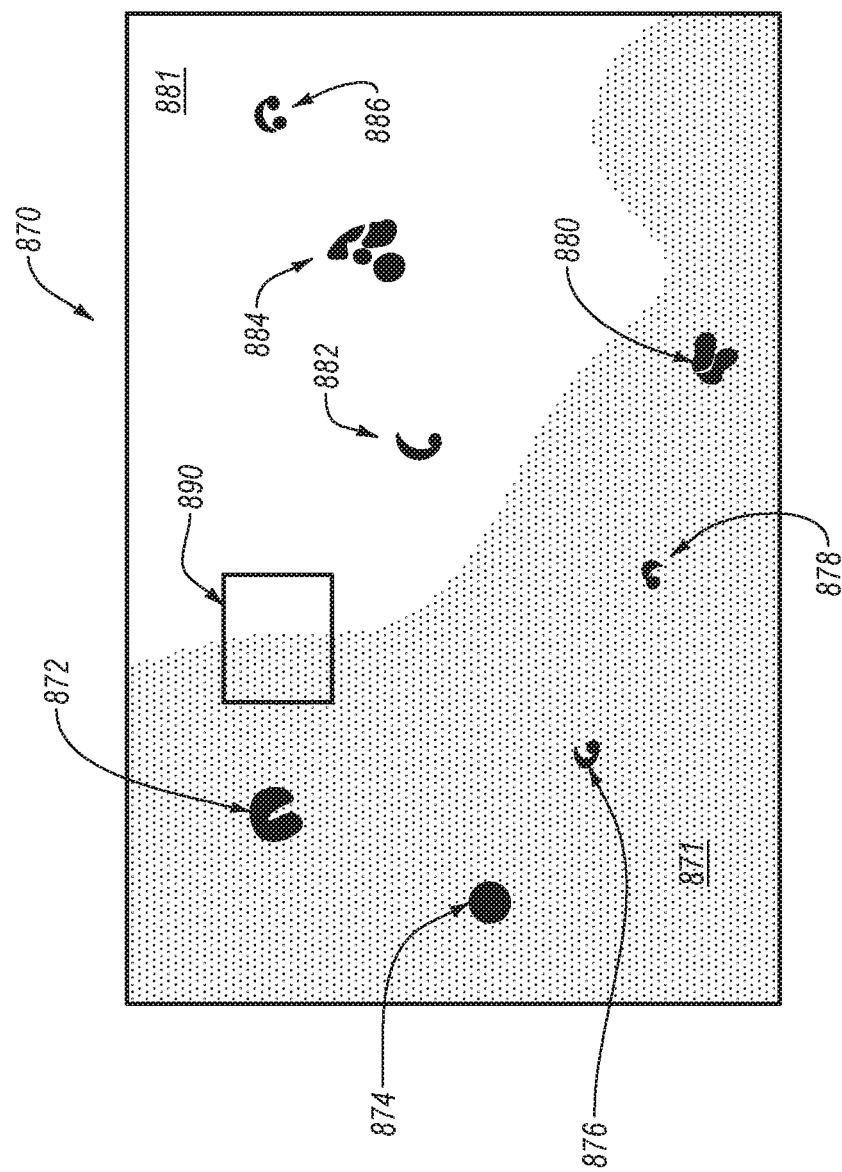
FIG. 8C is an FoV input image to the blob detection submodule of FIG. 8B, according to an embodiment.
Figure 8D:
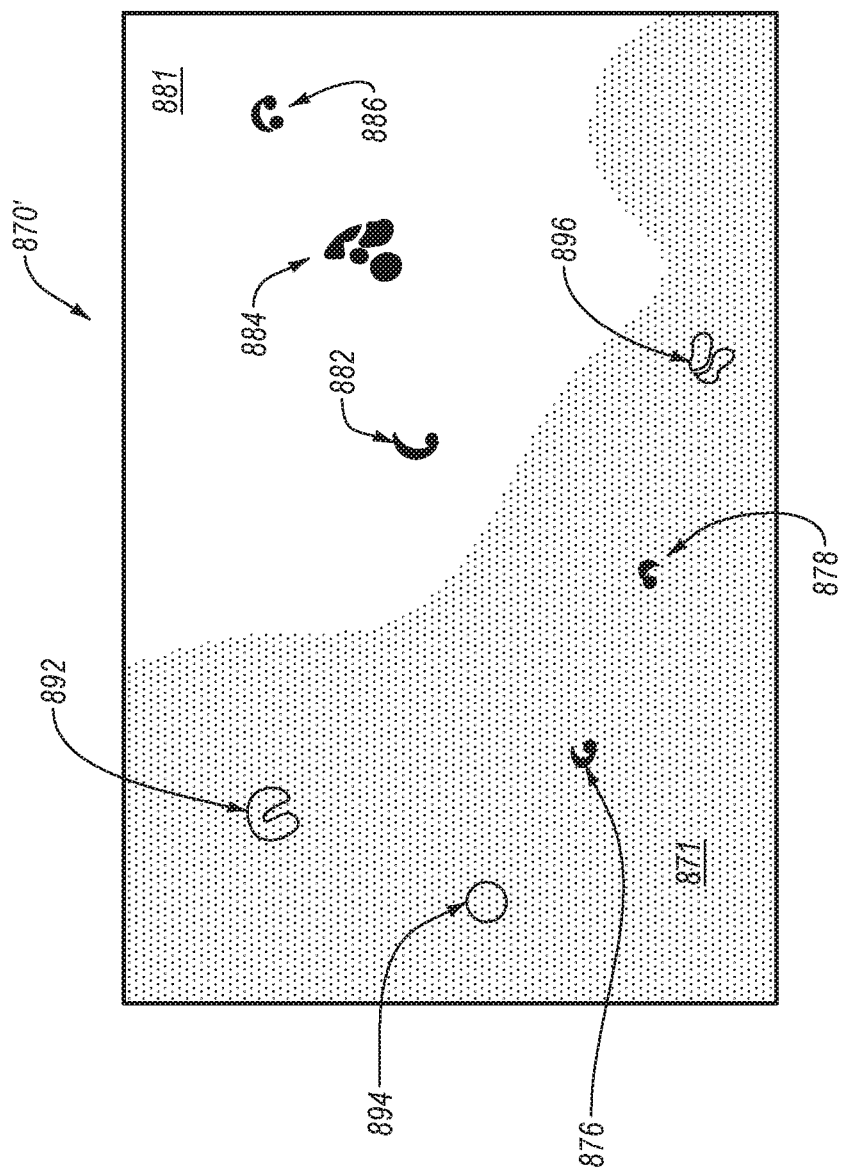
FIG. 8D is the FoV input image of FIG. 8C that has been modified, according to an embodiment.

The blob detection submodule 810 can include and perform a plurality of operations on the images to identify blobs therein. A schematic illustration of operations performed by the blob detection submodule 810 is depicted in FIGS. 8C-8D. The threshold determination submodule 812 can determine a local adaptive grayscale intensity threshold for an image as explained below.

FIG. 8C is a field-of-view image input into the blob detection submodule of FIG. 8B. FIG. 8C is illustrates an FoV 870 of an image of a blood smear. The FoV 870 may be provided as adaptive grayscale intensity images from the output images 311 and/or one of binary images 421. The input FoV 870 shown in FIG. 8C contains four malaria parasites, 876, 878, 882, and 886. The input FoV 870 also contains three WBCs, 872, 874, and 880. The input FoV 870 has an artefact 884 (e.g. a platelet or stain aggregation). In addition, the input FoV 870 has a high noise region 871, as well as a low noise region 881.

The threshold determination submodule 812 can estimate the noise floor by locally determining the median grayscale intensity value over one or more windows 890 in the image (e.g., adaptive grayscale intensity image). The threshold determination submodule 812 can determine an image-wide or local (e.g., one or more discrete windows in an FoV) median grayscale intensity value for an FoV or window 890. For example, the threshold determination submodule 812 can calculate (e.g., determine) the median grayscale intensity value for the window 890 shown in FIG. 8C. The median grayscale intensity value for a location in an image (e.g., window) can provide a value for a local adaptive threshold, above or below which, the pixel intensity values from within the window may indicate the presence of a candidate object or cluster thereof (e.g., blob).

FIG. 8D is the field-of-view input image of FIG. 8C that has been modified. FIG. 8D is illustrates a corrected FoV 870' of an image of a blood smear. The threshold determination module 812 can receive information about the presence of WBCs 872, 874, and 884 in the FoV 870 from the WBC detection mask input (e.g., binary images 421). If the input FoV 870 contains one or more WBCs 872, 874, and 884, the threshold determination module 812 can replace the pixels belonging to the WBCs 872, 874, and 880 with the median grayscale pixel intensity from across the image (e.g., the median grayscale intensity of the entire image or one or more portions thereof, or the median grayscale pixel intensity that excludes pixels with WBCs) to produce a corrected FoV 870'. This is schematically depicted in FIG. 8D where the grayscale intensity of the pixels belonging to WBCs 872, 874, and 880 of FIG. 8C have been replaced with the image-wide median grayscale pixel intensity value shown in objects 892, 894, and 896, respectively. With the WBC pixels replaced in the corrected FoV 870' by the median grayscale pixel intensity, the noise floor or threshold estimation (e.g., median pixel intensity estimation for a window) will not respond to WBCs by raising the threshold in the vicinity of the WBCs. Consideration of WBCs would have the undesired effect of reducing the sensitivity to parasites proximate to WBCs. Stated another way, consideration of WBCs in the determination of median pixel intensity estimation for a window (e.g., local noise floor estimation) would skew the noise floor estimation toward thresholds that tend to reduce sensitivity to parasites (e.g., parasites such as malaria that are similar in grayscale intensity to WBCs). Accordingly, the threshold determination submodule 812 can estimate the noise floor by locally determining the median grayscale intensity value over one or more windows in the image while discounting any variations in medial pixel grayscale intensity due to the presence of WBCs. The positions of the WBCs are known and provided in the WBC detection masks. In some embodiments, at least some of the windows may contain one or more candidate objects (e.g., blobs) therein, and pixels from the candidate object contribute to the calculation of the median pixel intensity of the window when the noise floor estimation is made. For example, the grayscale intensity values of the pixels in the of the candidate objects are considered when calculating the median grayscale intensity or local noise floor because the pixels corresponding to the hitherto unknown candidate objects or clusters thereof do not correspond to a WBC and are therefore used in the calculation(s). In some embodiments, the amount of candidate objects in a window can represent a population of pixels that is so small (e.g., less than 10%, less than 5%, less than 2%) that the adaptive grayscale threshold determined therefrom is not skewed to provide inaccurate results. The local noise floor can be used to set or determine the local adaptive grayscale (intensity) threshold. For example, the local noise floor can be used as the local adaptive grayscale threshold, or some grayscale intensity value above or below the local noise floor can be used as the local adaptive grayscale threshold.

Returning to FIG. 8C, the median grayscale intensity value (for the pixels) may be determined over one or more of a plurality of windows 890 in an image. The windows 890 may be located (e.g., tiled or placed) in/over the image (e.g., FoV) in a regular pattern in what is known as a "sliding window filter." While the sliding window approach may be applied to reduce noise in an image; in the present disclosure, the sliding window filter is used to estimate the noise (e.g., the background) in the FoV or window 890. The size of window 890 may be selected to provide a desired noise floor estimation sample size or spatial resolution. For example, larger windows may result in more robust noise floor estimation, but would also enlarge the spatial scale of the noise floor estimation, which may result in missing small, low noise regions. Conversely, smaller windows may allow better spatial resolution, but may be less robust in noise floor estimation. In some embodiments, the size of the window 890 can have at least one dimension (e.g., a width and/or height) of at least about 10 pixels, such as about 10 pixels to about 100,000 pixels, about 100 pixels to about 10,000 pixels, about 10 pixels to about 1000 pixels, less than about 10,000 pixels, or less than about 100,000 pixels.

The "stride" of the sliding window filter (e.g., distance between successive applications of the window filter) may be selected to provide a selected resolution or computational burden. For example, the sliding window filter may be computed with a stride of one pixel, such that when the median grayscale intensity value is calculated across window 890, then window 890 is moved by one pixel to the right and the median grayscale intensity value is computed again, and so on. In embodiments, each of the local median grayscale intensity values (e.g., calculated by replacing the WBC pixels) can be correlated to the corresponding window they were determined from. A stride of one pixel can compute a median filtered grayscale intensity image at the same resolution as the original image, but the computational burden may be very high (e.g., four times as high as a stride of two pixels). In embodiments, the stride may be two or more pixels, such as at least two pixels, at least five pixels, at least 10 pixels, at least 50 pixels, at least 100 pixels, at least 1000 pixels, or at least 10,000 pixels. This may reduce the computational burden, but decrease the resolution of the filtered image, which may decrease the fidelity of the noise floor estimation. In some embodiments, when the sliding window stride is more than one pixel, the median filtered image may be interpolated up to the original resolution of the input image. In some embodiments, different strides can be selected responsive to a specifically selected resolution or computational burden.

In some embodiments, one or more windows 890 can be used to determine the median grayscale intensity value (e.g., noise floor estimation for adaptive grayscale threshold) for each portion of an image, such as a locally varying/adaptive median grayscale intensity of (e.g., noise floor) each portion of the image. In some embodiments, an image-wide grayscale intensity value or the locally varying median grayscale intensity value for an FoV or window therein can be used to replace WBC pixels in the image to determine the local adaptive grayscale threshold. Such a technique may allow a closer approximation of the actual background (e.g., noise) in the image by reducing the impact of variations due to a known non-analyte such as a WBC. For example, the pixels corresponding to a known WBC in a window can be replaced with the median grayscale intensity value determined for the window or with an image-wide median grayscale intensity value. As noted above, the value of the median gray scale intensity may vary over an image or portions thereof Likewise, the determined local adaptive grayscale (intensity) thresholds can vary over an image or portions thereof. Accordingly, a system and method for detecting analytes in a fluid such as blood can apply a plurality of local adaptive grayscale (intensity) thresholds to the corresponding windows of an image to produce a spatially varying/adaptive estimate of the noise floor (e.g., median grayscale intensity values of the background and candidate objects) in the image or portion thereof.

The noise floor can be estimated (e.g., by the threshold determination module 812) for each window in an FoV, the entire FoV, or the entire image, and can be spatially varying according to the portion of the image in question. A median filtered grayscale intensity image or noise floor image, is an image of the spatially varying/adaptive estimate of the noise floor in the FoV or image. The pixels of the objects of interest may, for the most part, may have grayscale intensity values above the median grayscale intensity value of the noise floor image (e.g., the local adaptive threshold) at their location in the image. Objects of interest may include parasites and WBCs. Objects of interest may be detected by subtracting the noise floor image from the grayscale intensity image and applying a threshold.

The blob detection submodule 814 may apply a threshold (e.g., local adaptive threshold) to identify the presence and/or location of any objects of interest (e.g., blobs) in the FoV(s)/image(s). The local adaptive threshold may include some grayscale or color intensity value(s) in excess of or below a selected value (e.g., noise floor estimate or amount above the noise floor estimate). For example, the local adaptive threshold may be selected to identify grayscale or color intensity value(s) above the noise floor or some value(s) thereabove. Accordingly, the noise floor image plus the local adaptive threshold value may be considered as the (spatially varying/adaptive) threshold image. Any pixels in an image having a grayscale intensity above (e.g., or below depending on whether the image is a non-inverted grayscale intensity image) values in the threshold image may be considered objects of interest. Stated another way, objects of interest (e.g., blobs) may be identified or detected by subtracting the noise floor image from the grayscale intensity image and identifying any pixels having a grayscale intensity value greater than a selected (grayscale intensity) threshold value (e.g., applying the threshold). Groups or clusters of pixels of objects of interest may indicate the presence of one or more blobs. The blob detection module 814 may identify one or more groups or clusters of pixels in one or more windows, FoVs, and/or focal planes, as a blob and output one or more detection masks 811 noting the location of the blob(s), such as in specific window(s), FoV(s), and/or focal plane(s). The blob detection module 814 can output the one or more detection masks 811 to the blob clustering submodule 220 of FIG. 2.

Figure 8E:
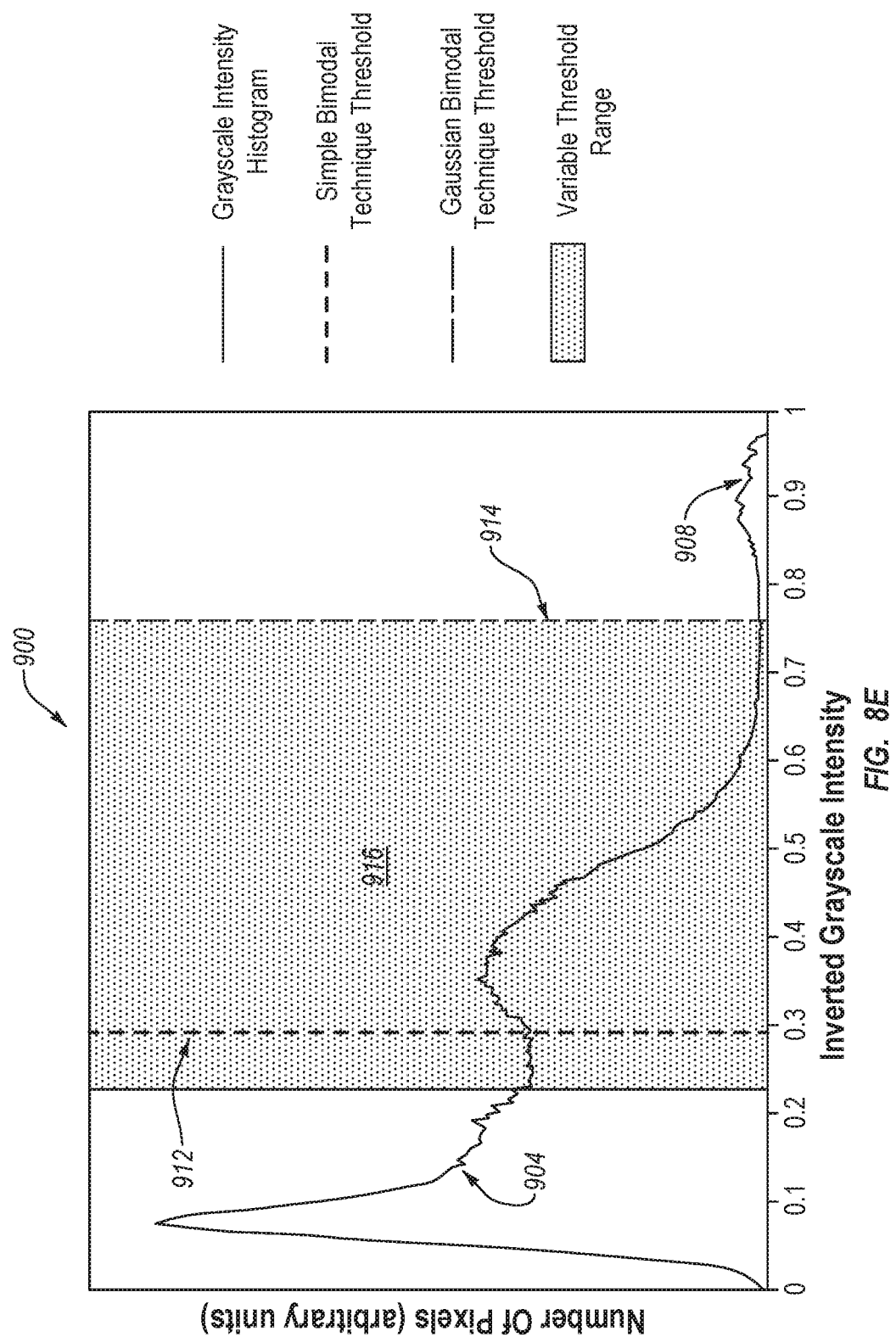
FIG. 8E is a grayscale intensity histogram for the pixels of the FoV image of FIG. 8C, according to an embodiment.

FIG. 8E is a grayscale intensity histogram 900 for the pixels of the field-of-view image of FIG. 8C. FIG. 8E shows the grayscale intensity histogram 900 of the FoV image of FIG. 8C as a solid line 904. The histogram 900 depicts the inverted grayscale intensity (expressed as a value extending from 0 to 1.0 from right to left, with 1 being 100%) versus the number of pixels (in arbitrary units). The grayscale intensity of the background extends from zero up to about 0.75. The bump 908 in the histogram at about 0.9 may correspond to the grayscale intensity values of WBCs in the image 870 (FIG. 8C). The grayscale intensity values of the parasites in the image 870 (FIG. 8C) may range from about 0.3 to around 0.8. Accordingly, the grayscale intensities of the background and the parasites may overlap. Additionally, there are no conspicuous peaks in the histogram from the parasites because the number of pixels is negligible compared to the entirety of the image.

The vertical line 912 corresponds to the (constant) threshold computed by the Simple Bimodal Technique. It can be seen that the application of the Simple Bimodal Technique threshold to the grayscale intensity image will result in a large number of false positive detections (values to the right of the line 912) which may overwhelm an image analysis system. The vertical line 914 corresponds to the (constant) Gaussian Bimodal Technique threshold. As depicted in FIGS. 8C and 8E, the application of the Gaussian Bimodal Technique threshold will succeed in detecting one parasite in the high noise region (e.g., object indicated by the values of grayscale intensity above the threshold of about 0.76 as shown (e.g., above 0.76 but below about 0.8)), but will miss the three other parasites altogether (e.g., objects within the grayscale intensity range below about 0.76).

The thresholding techniques disclosed herein can provide a locally varying threshold capable of resolving objects having similar grayscale intensities to the background in a specific region of an image. For example, the region 916 corresponds to the range of threshold values which can be computed by the technique of the present disclosure. These are the values of the pixels in the threshold image mentioned above. Accordingly, any values above the values for pixels in the threshold image calculated above, may indicate the presence of an object of interest or blob (e.g., a parasite).

Figure 8F:
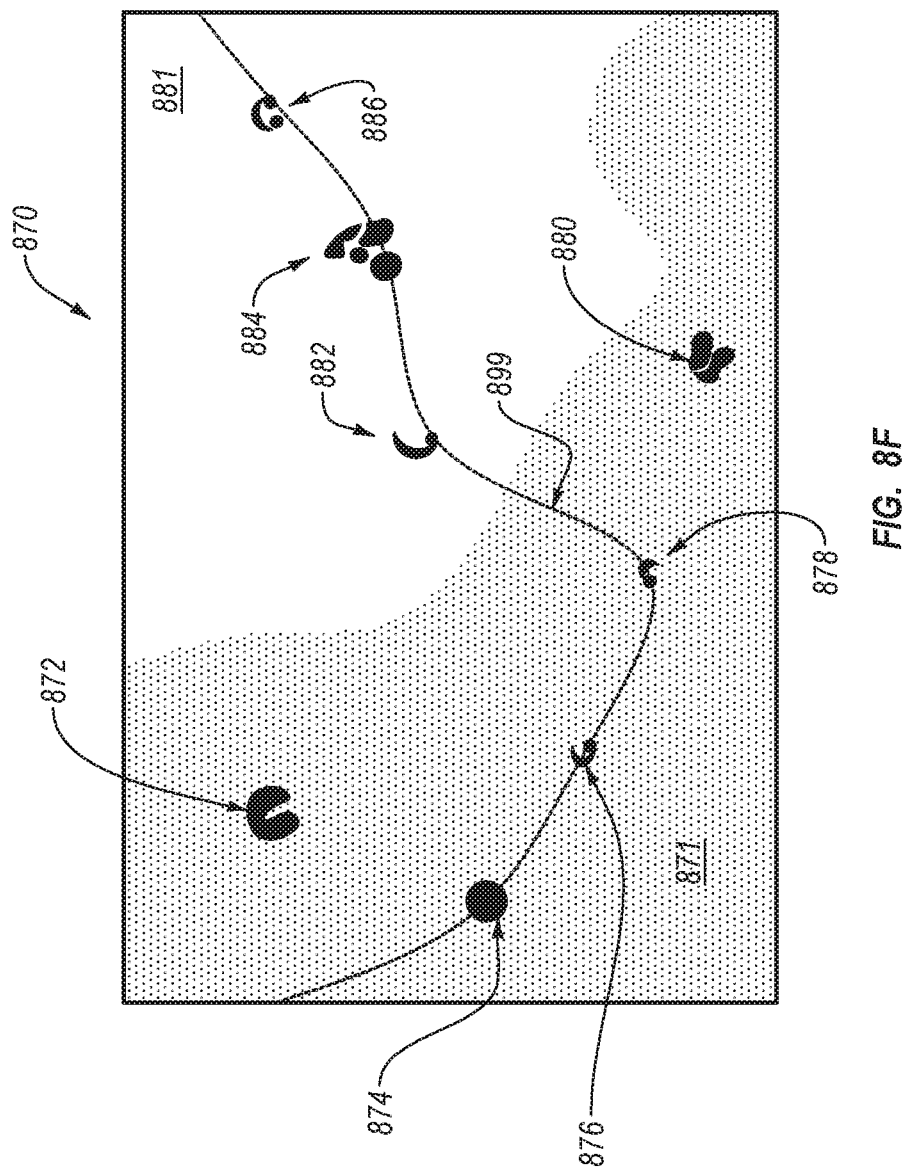
FIG. 8F is an illustration of a path that traverses the FoV image of FIG. 8C, according to an embodiment.

An illuminating view of these results may be obtained by examining the grayscale intensity and threshold values along a path through the image 870 of FIG. 8C. FIG. 8F is an illustration of a path that traverses the field-of-view image of FIG. 8C. FIG. 8F shows a path 899 through the image 870 of FIG. 8C. The windows 890 (FIG. 8C) may trace along the path 899 to produce a varying grayscale intensity threshold determination of the pixels along the path 899. The path 899 passes through WBC 874, parasite 876, parasite 878, parasite 882, artifact 884, and parasite 886. The path 899 passes through both the high noise region 871 and the low noise region 881.

Figure 8G:
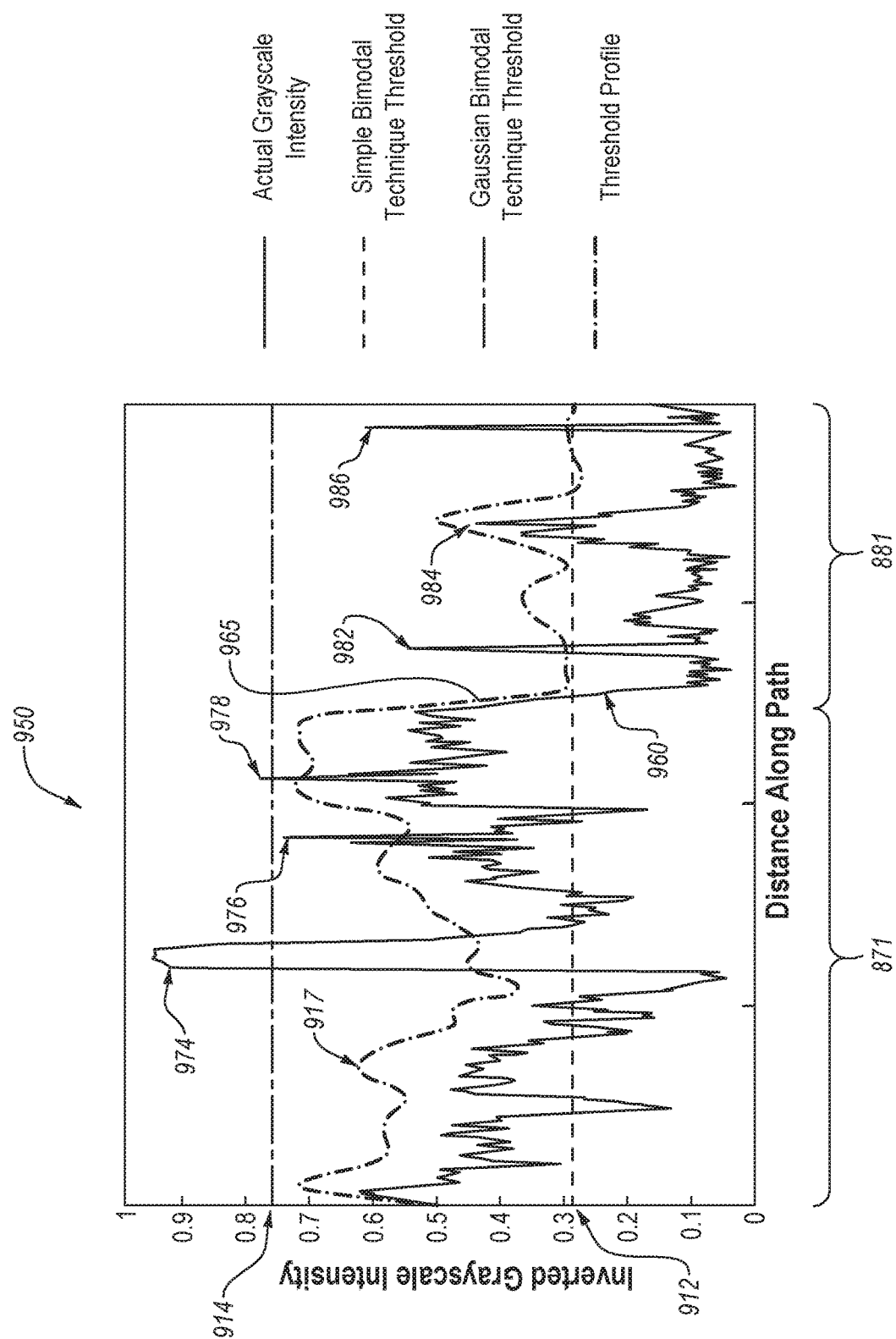
FIG. 8G is a graph of inverted grayscale intensity as function of position on the path of FIG. 8F, according to an embodiment.

The local adaptive threshold can vary depending upon the location in the image. The values of the local adaptive threshold along the path 899 in FIG. 8F are shown as line 917 (e.g., threshold profile) having variable values in FIG. 8G. FIG. 8G is a graph 950 of the inverted grayscale intensity as function of position on the path 899 of FIG. 8F (in arbitrary units correlating the position as the path 899 travels from left to right). The high noise region 871 corresponds to the portion of the graph 950 left of the abscissa position 965 and the low noise region 881 to the portion of graph 950 to the right of the abscissa position 965 in FIG. 8G. The peaks 974, 976, 978, 982, 984, and 986 in FIG. 8G correspond to WBC 874, parasite 876, parasite 878, parasite 882, artefact 884, and parasite 886 (each in FIG. 8F), respectively. In FIG. 8G, the Simple Bimodal Technique threshold 912, Gaussian Bimodal Technique threshold 914, Variable Threshold (local adaptive threshold shown as the threshold profile at line 917 and calculated as described herein), and actual grayscale intensity 960 are shown. It can be seen that the Simple Bimodal Technique threshold 912 has a constant value which may identify WBC 874 and all four parasites 876, 878, 882, and 886 as evidenced by the corresponding peaks 974, 976, 978, 982, and 986 of the actual grayscale intensity 960 extending above the Simple Bimodal Technique threshold 912. However, many false positive detections may also be indicated by the Simple Bimodal Technique threshold 912 (e.g., due to a large imbalance in the respective populations of the classes of the pixels in the bi-modal population), which, as mentioned previously, may cause problems for the image analysis system. For example, the peak 984 corresponding to the artefact 884 may be incorrectly identified as an object of interest.

It can also be seen that the Gaussian Bimodal Technique threshold 914 has a constant value and may detect only WBC 874 and parasite 878 as shown by the peaks 974 and 978 which extend above the Gaussian Bimodal Technique threshold 914. Using the Gaussian Bimodal Technique threshold 914 may cause parasites 876, 882, and 886 (each in FIG. 8F) to go undetected as the corresponding peaks 976, 982, and 986 are below the Gaussian Bimodal Technique threshold 914.

The local adaptive (grayscale intensity) threshold (e.g., grayscale intensity of the threshold image) along path 899 of FIG. 8F is shown as the dashed and dotted line (threshold profile of line 917) in FIG. 8G. The local adaptive threshold for a particular path, line, or window of an image can adaptively vary between any of the values of the region 916 (FIG. 8E). The grayscale intensity value of the threshold image along path 899 corresponds to the threshold profile at line 917. As shown, the threshold profile at line 917 (and the techniques for determining and applying the threshold described herein) can provide the variable or adaptive threshold to identify objects of interest (e.g., blobs) that would go otherwise undetected with the Simple Gaussian Bimodal Technique threshold 914 and preventing over inclusive threshold Bimodal Technique threshold 912 (preventing false positives); while allowing artefacts 884 (FIG. 8F) and/or other non-analytes (e.g., non-parasites) to be excluded as objects of interest.

While the threshold profile set at line 917 detects all of the desired objects, namely, WBC 874 and all four parasites 876, 878, 882, and 886, it also does not detect large numbers of false positives because it rides the noise floor. That is, the threshold profile set at line 917 roughly tracks the local average grayscale intensity in an image. For example, it can be seen that the values of the threshold profile set at line 917 in the high noise region 871 are generally above the actual grayscale intensity value 960 (e.g., except for at peaks corresponding to objects of interest) so that false positives are avoided in the high noise region 871. The values of threshold profile set at the line 917 are relatively lower in the low noise region 881, responding to the lower levels of noise in that region, but are still generally above the actual grayscale intensity value 960 (e.g., except for peaks corresponding to objects of interest). The threshold profile set at the line 917 may ride over (e.g., extend above) artefact 884 at peak 984 because the artefact 884 was not present in the WBC detection input mask (e.g., the artefact 884 was not identified as a WBC) of the binary images 421 of FIG. 8B. Such absence from the WBC input detection mask of the binary images 421 would cause the artefact 884 to be to be treated as background when determining the grayscale intensity threshold of a window containing the artefact 884, thereby leading to a grayscale intensity threshold value that rides over the grayscale intensity value of the artefact 884. As differentiated from drastically smaller parasites (e.g., at least 50%, 75%, or 90% smaller than the artefact 884), the relative size of the artefact 884 may skew the grayscale intensity threshold determination far enough to cause the threshold profile set at line 917 (e.g., local adaptive threshold) to exceed the artefact grayscale intensity. The inventors currently believe that in most cases, certain parasites (e.g., ring-form malaria parasites) are not large enough to cause the threshold determination module 812 (FIG. 8B) to skew the local grayscale intensity threshold determination(s) enough to cause the threshold profile to ride over the parasites. Such determinations may depend on the relative size of the window(s) and the artefacts and/or parasites therein. For example, a window having a large percentage of pixels (e.g., 50% or more) corresponding to an artefact may produce and adaptive threshold that rides over any parasites therein. In contrast, a window having only a minute amount of pixels (e.g., less than 10%, 5%, 2%, 1%) containing parasites may not result in a calculated adaptive threshold above the intensity of the pixels corresponding to the parasites. Accordingly, the size of the windows may be selected to provide an adaptive (grayscale intensity) threshold capable of riding over artefacts 884 while detecting parasites.

Returning to FIG. 8B and in accordance with FIG. 8G, the blob identification module 814 can be used to identify the presence of one or more peaks of the actual grayscale intensity 960 that exceed the threshold profile set at the line 917 (or local adaptive threshold). The one or more peaks of the actual grayscale intensity 960 that exceed the threshold profile set at the line 917 may be identified as objects of interest (e.g., blobs) by the blob identification submodule 814 and output as detection masks 811. The blob identification submodule 814 can output the detection masks 811 to the blob clustering submodule 820 (FIG. 8A) as described herein.

C. Feature Extraction Module

Figure 9:
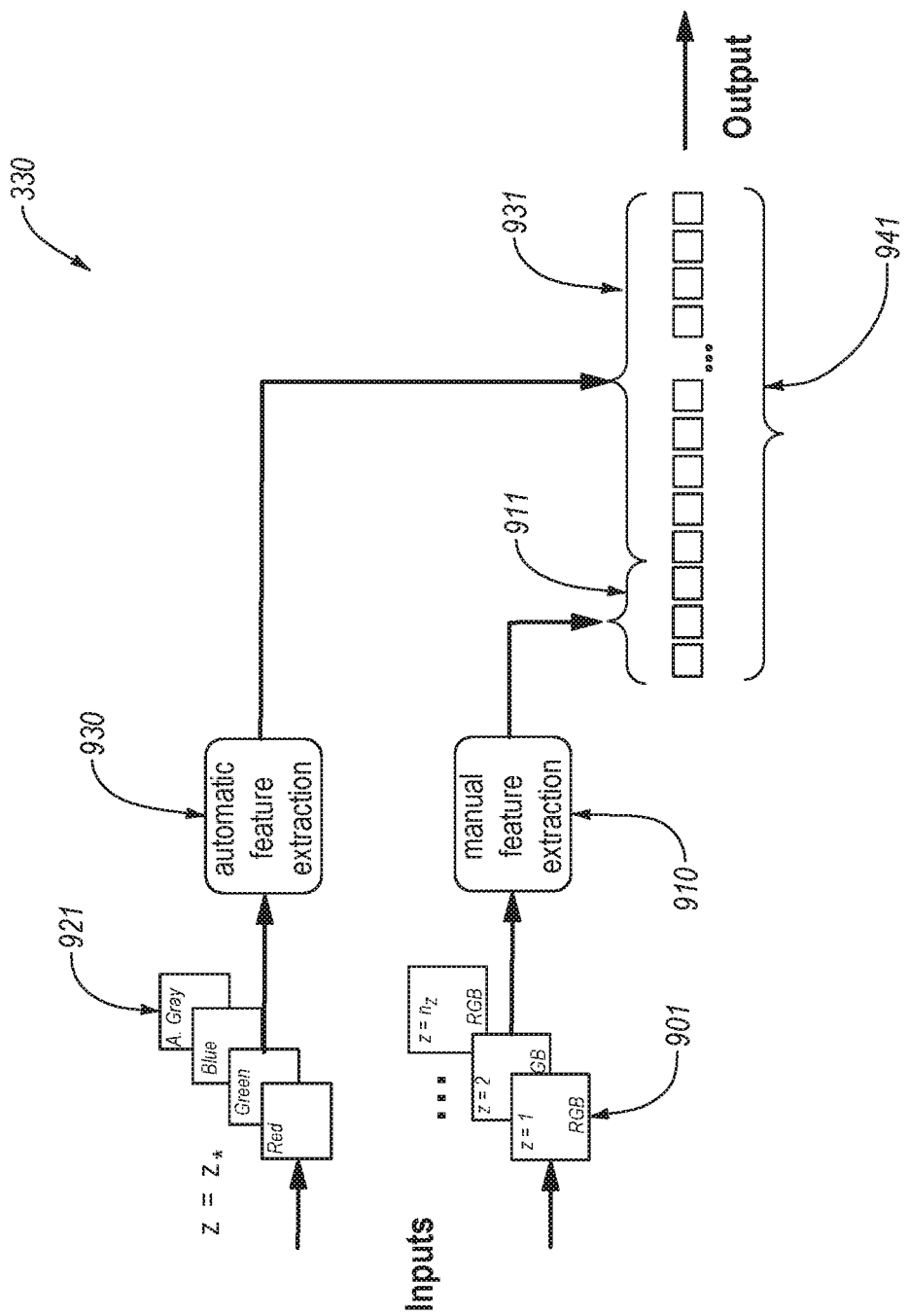
FIG. 9 is a detailed schematic of a feature extraction module of the system of FIG. 3A, according to an embodiment.

FIG. 9 is a schematic of a feature extraction module 330 also shown in FIG. 3A. The feature extraction module 330 is configured to represent each candidate object as a feature vector and output the same. The feature vector(s) can be classified as parasite (even which species or stage of parasite) or artifact by the object classifier module 340 of FIG. 3A. The feature extraction module 330 is configured to compute at least one of two types of features as shown in FIG. 9. The features can be manual features or automatic features. The feature extraction module 330 has two sets of inputs, one for the manual feature extraction and the other set for the automated feature extraction. The feature extraction module 330 can operate in one of two modes, manual feature extraction ON, or manual feature extraction OFF. In various embodiments, manual feature extraction can be ON or OFF, while the automatic feature extraction is always ON.

A first approach to feature extraction is manual feature extraction or feature engineering in the computer vision field. These are features that are intentionally designed to measure particular attributes of a candidate object, and rely heavily on learned (e.g., previously known or preprogrammed) domain knowledge.

Inputs 901 for the manual features are color-corrected R, G, B image patches containing the candidate object and all $n_z$ focal planes thereof. Submodule 910 of the feature extraction module 330 contributes three manual features 911 to the feature vector.

The first manual feature is the best focus score of the candidate object (e.g., a Brenner score). Referring back to FIG. 7, a focus score is computed over the image patch region for each of $n_z$ focal planes and the best focal plane is the one with the highest focus score. The second manual feature is the standard deviation (and/or other measure of dispersion) of the focus score across the focal planes of an FoV having the candidate object feature therein. The motivation behind this is that some artifacts, like air bubbles and dust particles on the specimen, will have the same focus score across all focal planes because they are far from being in focus, whereas ring-form malaria parasites (or other analytes) will have a narrow focus score distribution bracketing the best focal plane and thus a small standard deviation of focus score.

Submodule 910 can be configured to extract the third manual feature, which is called the red-shift score (the red-shift is being used herein as a descriptive term and is not related to the red-shift phenomenon caused by the Doppler effect). The red-shift score helps to distinguish between parasites and artifacts. The red-shift score relies on the confluence of two concepts. The first concept is optical dispersion, which refers to the variation in refractive index according to wavelength. This means that an uncorrected, simple lens will focus different wavelengths of light at different focal planes (e.g., different lengths away from the lens).

FIGS. 10A and 10B are illustrations of light rays being refracted to different focal planes through a simple lens and a lens with an achromatic correction, respectively. In FIG. 10A, rays of light for three representative wavelengths in the red, green, and blue portions of the spectrum are shown coming to focus at planes 1001, 1002, and 1003, respectively. As the light passes through the simple lens 1010, the red, green, and blue wavelengths refract to different focal planes. The focus vs. wavelength curve 1030 for a simple lens is shown in FIG. 10C and the representative focal planes for the rays that came to focus at 1001, 1002, and 1003 are indicated by the points on the curve 1030 at 1031, 1032, and 1033, respectively.

Lenses with achromatic correction help to limit the amount of chromatic aberration caused by dispersion. An achromatically corrected lens is shown in FIG. 10B, along with three representative wavelengths in the red, green, and blue portions of the spectrum. The achromatically corrected lens can include, for example, a simple lens component 1010 (e.g., crown glass component) that is convex, mounted or bonded to an achromatic component 1020 (e.g., flint glass component) that is concave. An achromatically corrected lens is designed to bring two wavelengths to focus at the same plane, such as plane 1005 shown in FIG. 10B. As shown, in some embodiments, the two wavelengths are in the red and blue portions of the spectrum.

A focus vs. wavelength curve for an achromatic lens is shown as curve 1040 in FIG. 10C and the representative focal planes for the rays that came to focus at 1004 and 1005 are indicated by points 1044 and 1045 on the curve 1040, respectively. It can be seen in FIG. 10C that the portion of the curve 1040 in the red region of the spectrum (640-700 nm) is more gently sloping upward than the portion of the curve 1040 in the blue region (450-500 nm). Thus, as the focus setting on the microscope is moved towards the upper portion of the graph, blue light will defocus more quickly than red light. Green light does not go out of focus as quickly as either the red or the blue components of light as the microscope focus is shifted upward. This can be seen from the relative flatness of the bottom of the curve 1040 in FIG. 10C, which is in the green region of the spectrum. The first concept relies on this shift in light focal planes as the microscope focus is adjusted.

Figure 11:
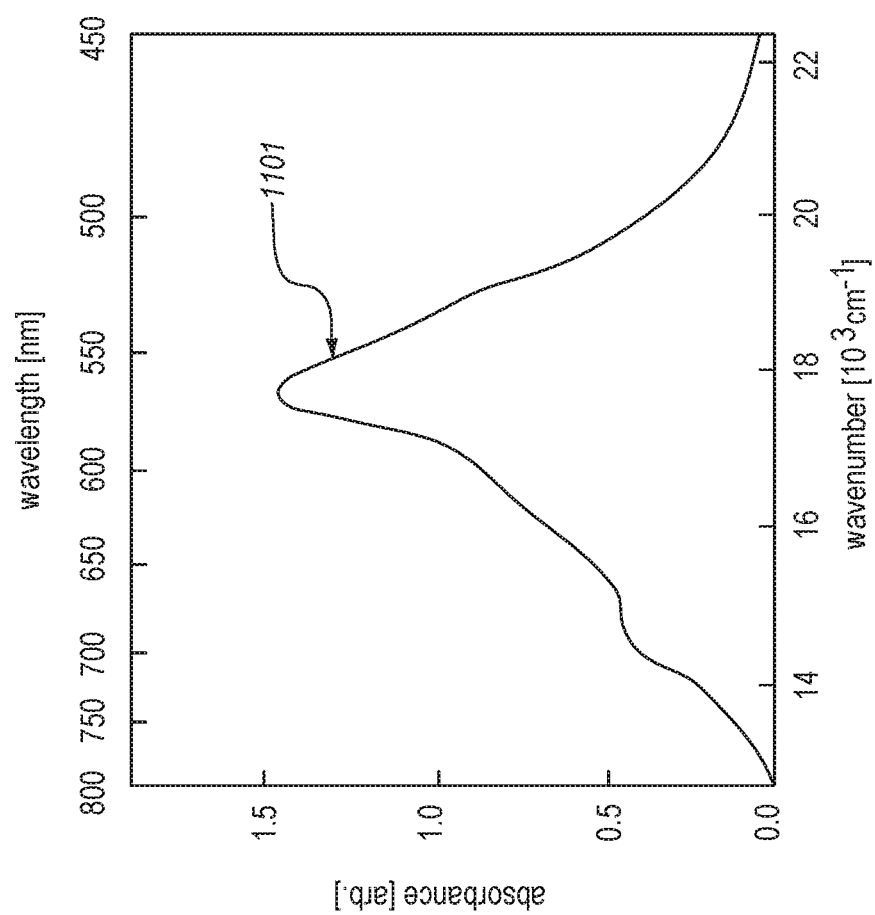
FIG. 11 is a graph of the absorption spectrum of a Giemsa stained DNA sample, according to an embodiment.

The second concept which the red-shift score depends on, are the light absorption properties of analytes (e.g., DNA) when stained, such as with Giemsa. FIG. 11 is a graph of the absorption spectrum 1101, which shows peak absorption in the green region of the spectrum. The absorption of green light by a conjugate of Methylene blue and Eosin Y is amplified in the presence of DNA. This means that material on a microscope slide containing DNA—cell nuclei for example—will largely absorb green light and transmit red and blue light, which accounts for their magenta color in transmitted light microscopy. Artifact objects do not contain DNA, and, therefore, tend to absorb less in the green portion of the spectrum. Accordingly, the artifacts do not appear magenta in the image.

Based on the observation above that changing the focal plane of the microscope upward will defocus blue wavelengths faster than red wavelengths, it follows that magenta objects will appear more red because the blue component of the light will have diffused to a larger spatial region, more so than the red light. This is the basis of the red-shift score, which measures the increase in redness of the darkest portion of the detected candidate object, which for a true Malaria parasite is the nucleus of the parasite cell. An artifact that transmits red, green, and blue light more equally will not turn more red as the focus of the microscope is shifted upward, which counterbalances the red-shift effect of the red and blue components as described above. Thus, the red-shift score provides a basis for distinguishing between parasites and artifacts.

The systems and methods disclosed herein are configured to analyze the candidate object images for red-shift and provide a score based thereon. The manual feature extraction submodule 910 (and associated microscope) can be configured to determine the red-shift score as described above. While DNA, Malaria parasites, and the color red are provided as an example, the concept of red-shift scoring can be applied to different colors and analytes, without limitation.

The second type of features extracted by the feature extraction module are automatic features, which can be automatically learned by a system including at least one memory storage device and at least one processor, such as a convolutional neural network (CNN). CNNs are deep learning models (applied by computer systems) that learn multiple levels of representation. Starting with the raw input layer, each successive layer (e.g., convolutional, pooling, sub-sampling, or fully connected layer) represents the information in the image at a slightly more abstract level. The weights (filters) in each layer are learned using a standard learning procedure such as back-propagation of error (backprop). In a CNN, each layer (of calculations) is performed by a distinct plurality of neurons (processing modules), and the neurons in each convolutional layer are not fully interconnected with all of the neurons in adjacent layers of the system. Rather, the neurons in the convolutional layers have only selected connectivity with adjacent convolutional layers to reduce the amount of inputs carried through to successive convolutional layers. At each convolutional layer, a convolutional kernel defines the region of connectivity with neurons in the previous layer. The convolutional kernel is sometimes referred to as the receptive field of the neuron in the convolutional layer. One or more of the final layers in the CNN is a fully connected layer having full connectivity to the immediately previous layer, effective to perform high-level reasoning based on the data (that has been repeatedly abstracted throughout the layers) provided therefrom. In some embodiments, ground truth(s) (e.g., image patches that contain ground truth objects, which have been identified by a human expert) can be used to train the weights of the CNN via a learning procedure. CNN's can be stored on and performed by a computer having one or more processors (e.g., central processing units (CPUs) or graphics processing units (GPUs)). The ground truths images or image patches can include known positive samples (e.g., identified to the CNN as having the analyte of interest) and known negative samples, (e.g., identified to the CNN as having no analyte therein, or having only known artifacts or other non-analyte objects therein). Accordingly, the CNN can learn weights from both known analyte and non-analyte species, which can be used to identify the same in samples.

In an embodiment, a computer vision system such as a microscope operably coupled to a digital recorder can be operably coupled to a CNN. Such systems can exceed human level performance in terms of accuracy. The automatic feature extraction submodule 920 can be configured to carry out feature extraction based at least in part on a feed-forward application of weights, pooling, and non-linear operations.

A large amount of data is required to train a CNN because of the richness of the model. If insufficient data are available for training, overfitting can occur, which results in poor generalization performance. In some embodiments, the systems and methods herein can increase the amount of training data by generating artificial data based at least in part on the training data itself. This process is called augmentation. Augmentation can take the form of one or more random transforms applied to the training images. Examples of augmentation transforms are translation, rotation, scaling, reflection, and color distortion.

One technique for color distortion consists of the following steps. First, the principal components transform of the training images in the R, G, B color space is computed. The eigenvectors are denoted $p_1$, $p_2$, $p_3$ with corresponding eigenvalues $\lambda_1$, $\lambda_2$, $\lambda_3$, respectively. Three random numbers $r_1$, $r_2$, $r_3$, are sampled from a bounded distribution, for example, a Gaussian with zero mean and standard deviation 0.1. To generate the augmented image, the following quantity is added to each pixel in the image:

$$[p_1\ p_2\ p_3][r_1\ \lambda_1\ r_2\ \lambda_2\ r_3\ \lambda_3]^T$$

The random numbers, $r_1$, $r_2$, $r_3$ are sampled once per image presentation during the training of the CNN.

The above technique for color distortion can lead to images with unrealistic color. It is desirable to introduce a color distortion method (and system for carrying out the same) that generates images with realistic color, while at the same time providing enough color distortion to avoid overfitting of the CNN. Such color distortion can aid in normalizing color variations in images due to color variations of stains from one sample to another. For example, in Giemsa stain, the relative amounts of basophilic blue and acidophilic eosin (red) present in the stained sample depends on pH of the stain, which varies in the field. Color normalization through the distortion methods herein may aid in achieving more accurate diagnoses. In a second color augmentation method of the present disclosure, each of the red, green, and blue channels (e.g., components) of the image can be distorted with a gamma non-linearity, which is also called a gamma correction, although in this case it is being used to transform the colors of the image rather than correct them. Gamma correction is defined by the following non-linear transform in equation 8:

$$\tilde{\psi} = \alpha \psi^\gamma \quad \text{Eq. 8}$$

where $\psi$ is the input value, $\tilde{\psi}$ is the output value and $0 < \gamma < \infty$ is the exponent of the non-linearity, and $\alpha$ is a scaling constant. When the input values $\psi$ are in the range [0,1], the scaling constant $\alpha=1$. The color augmentation method of the present disclosure samples four random numbers $r_1$, $r_2$, $r_3$, $r_4$ from a Gaussian with zero mean and standard deviation $\sigma$. Then, four values of $\gamma$ are computed via the relation $\gamma_i = e^{r_i}$, where is e the base of the natural logarithm. The augmented red, green, blue, and adaptive gray channel/component images are generated by equation 9 respectively, as follows:

$$\tilde{R} = R^{\gamma_1}$$

$$\tilde{G} = G^{\gamma_2}$$

$$\tilde{B} = B^{\gamma_3}$$

$$\tilde{\phi}_\alpha = \phi_\alpha^{\gamma_4} \quad \text{Eq. 9}$$

The random numbers $r_1$, $r_2$, $r_3$, $r_4$ are sampled once per image, per augmentation. Accordingly, each of the R, G, B and intensity $\phi$ channels can be individually and collectively augmented to provide a larger sampling of data to train a CNN suitable for use with the systems and methods herein.

Referring again to FIG. 9, image patches 921 are inputs to the CNN feature extractor 930. In some embodiments, an augmented set of ground truth image patches that have been augmented using a data augmentation scheme can be used to train the CNN to recognize analytes or non-analyte objects. That is, the raw images or portions thereof such as image patches are augmented using translation, rotation, scaling, reflection, and gamma-based color distortion as described above. In some embodiments, the at least one processor (associated with the CNN) is configured to learn a set of weights based at least in part on one or more of an augmented set of ground truth image patches, color-corrected image patches, or grayscale intensity image patches that have been augmented according any of the methods disclosed herein. For example, the ground truth image patches can be augmented by a data augmentation scheme that includes a random gamma correction of one or more of a red, green, blue, or grayscale intensity component of the ground truth image patches. In some embodiments, image patches at the best focal plane for each candidate object are presented for CNN training. In other embodiments, image patches of all focal planes are presented for CNN training. In some embodiments, the at least one processor is configured to augment color-corrected image patches and adaptive grayscale intensity image patches using an augmentation scheme. In some embodiments, outputting of the color-corrected image patches and the adaptive grayscale intensity image patches can include using an augmentation scheme to augment the color-corrected image patches and the adaptive grayscale intensity image patches. In some embodiments, during the testing phase of the CNN feature extractor, no augmentation is performed. In other embodiments, augmentation is performed during the testing phase and the outputs of the classifier module, shown as block 340 in FIG. 3A, are averaged over the augmented versions of each testing sample. In some embodiments, the at least one processor is configured to average an output of a machine learning classifier over the feature vectors corresponding to augmented versions of each of the color-corrected image patches and the adaptive grayscale intensity image patches.

The output of the CNN feature extraction submodule 930 is the CNN components 931 of the feature vector. In an embodiment that uses both manual and CNN features, the manual features 911 and the CNN features 931 can be concatenated to form the full output feature vector 941. In embodiments without manual features, the manual feature extraction submodule 910 is not executed and manual features 911 are not prepended to the output feature vector 941.

Returning to the system diagram in FIG. 3A, the output of the feature extraction module 330 are the feature vectors 331 of the candidate objects.

D. Object Classifier Module

The object classifier module 340 is configured to classify the feature vectors 331, as corresponding to an analyte (e.g., parasite) or artifact. The object classifier module 340 is configured to classify the feature vectors 331 or output from the feature vector extraction module 330, as parasite or artifact using a machine learning classifier. The machine learning classifier can be a program stored in one or more memory storage mediums, which is executable by one or more processors, such as in a computer system or network. The object classifier module 340 can be trained as disclosed above using the parasite ground truth data disclosed above. Different embodiments of the object classifier module 340 can include different types of classifiers. In an embodiment, the object classifier module 340 is configured as a linear support vector machine. For example, a linear support vector machine can include a computing device configured to perform a linear support vector classification. In various embodiments, the object classifier module 340 can be configured as one or more of the following types of classifiers: a non-linear kernel support vector machine, neural network, logistic regression, random forest decision trees, gradient boosted decision trees, AdaBoost, or Naïve Bayes classifier.

The output of the object classifier module 340 can include a calibrated probability that the candidate object is a parasite (e.g., analyte) or artifact. The object classifier module 340 is configured to output classified object data 341 (FIG. 3A). The classified object data 341 can include a score(s) corresponding to (e.g., indicating the extent of) the similarity between the ground truth object(s) and the candidate object(s). The similarity can be expressed as a probability that the candidate object (or one or more aspects thereof) is an analyte such as a parasite (or one or more aspects thereof). In some embodiments, the object classifier module 340 (machine learning classifier) can be configured to classify the one or more feature vectors by averaging the output of the machine learning classifier (e.g., probabilities) over the feature vectors corresponding to augmented versions of each of the input image patches.

E. Diagnosis Module

The diagnosis module 350 (FIG. 3A) can be configured to determine and to output a diagnosis 351 for the sample (e.g., blood slide) based at least in part on the classified object data 341, i.e., either POSITIVE—the sample does contain malaria parasites, or NEGATIVE—it does not. The diagnosis 351 can include an estimate of the parasitemia ($\hat{p}$ as used in equation 10 below). In some embodiments, the diagnosis module 350 can be configured to determine the parasitemia. In some embodiments, the diagnosis module is configured to run a diagnosis algorithm that counts the number of candidate objects $H_c$, whose object classifier scores are above some threshold $\Theta_c$. In some embodiments, more than one type of candidate object (e.g., ring form malaria parasite and late-stage parasite objects) can be counted at one time. Subsequently, the number of candidate objects with object classifier scores above $\Theta_c$, is thresholded at some level $\Theta_N$. In other words, a sample is flagged as POSITIVE if $N_c > \Theta_N$, and NEGATIVE otherwise. The thresholds $\Theta_c$ and $\Theta_N$ can be optimized on a validation set whose diagnoses are known, either through microscopic examination by a human expert or a molecular test such as polymerase chain reaction (PCR). The optimization is based at least in part on a given objective for the validation set, such as maximizing balanced accuracy, or maximizing sensitivity at a fixed level of specificity.

The image analysis systems disclosed herein, being a real-world system, can have some residual noise floor that depends on the threshold applied to the object classifier scores. In other words, at some object classifier thresholds, some non-parasite objects will have scores above that threshold. In some embodiments, the median object-level false positive rate $\overline{FPR}$ is computed on the negative samples in the validation set as a function of an object classifier score threshold $\Theta_q$. At the same time, the median object-level sensitivity rate $\overline{SNS}$ is computed on the positive samples in the validation set as a function of the same classifier threshold $\Theta_q$. The estimated parasitemia is then computed using equation 10 as:

$$\hat{p} = \frac{N_q - \overline{FPR}}{\overline{SNS}} \qquad \text{Eq. 10}$$

where $N_q$ is the number of candidate objects with classifier score above the threshold $\Theta_q$. It is understood that $\hat{p}$ is a function of the object classifier score threshold $\Theta_q$. The classifier score threshold $\Theta_q$ is determined by optimizing a given objective, such as mean square parasitemia error, across the validation set.

F. System Hardware

Figure 12:
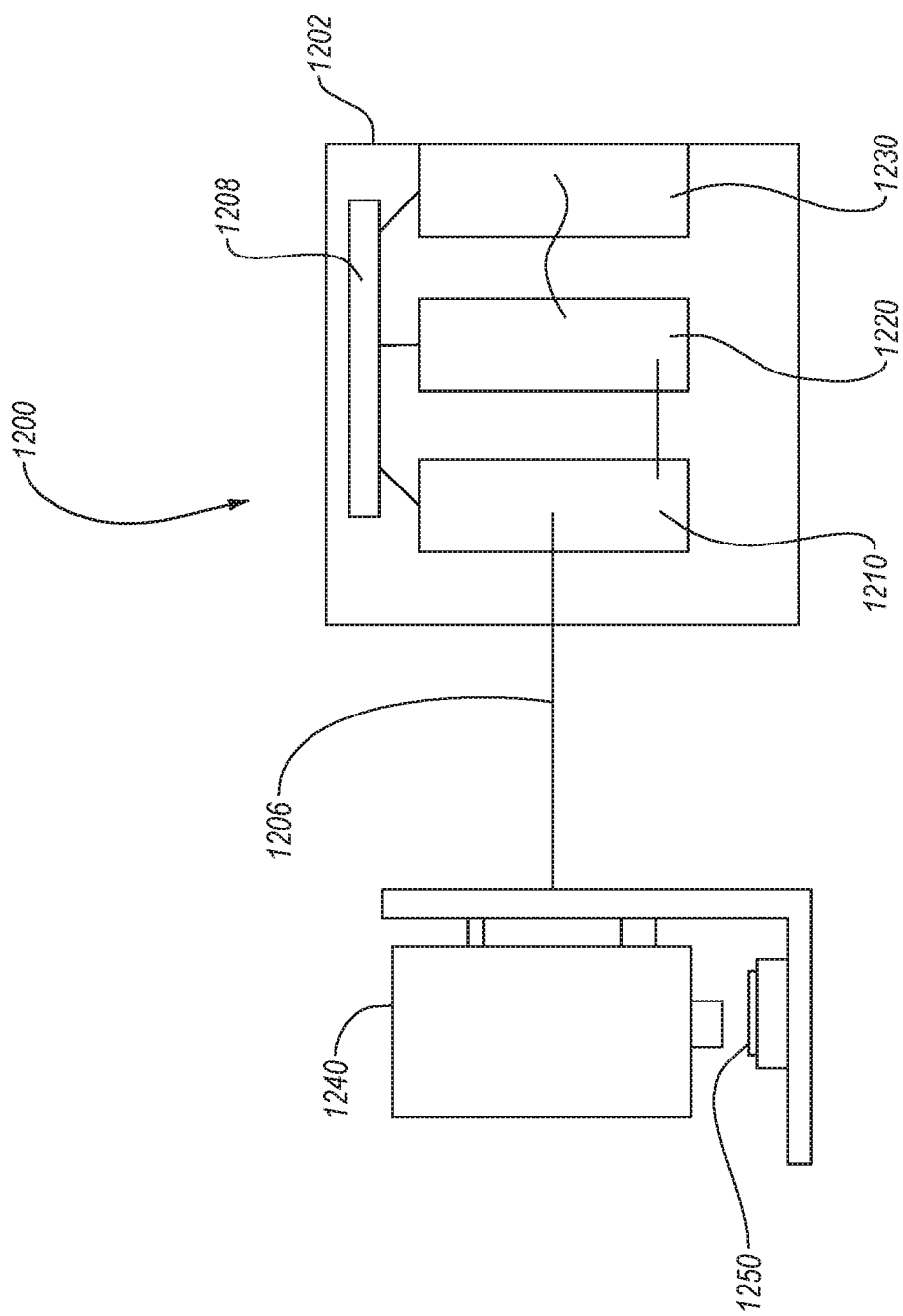
FIG. 12 is a schematic of a system for determining a presence of an analyte in a sample, according to an embodiment

FIG. 12 is a schematic of a system 1200 for determining the presence of an analyte in a sample, according to an embodiment. In some embodiments, the system 1200 can be configured to perform one or more of any of the algorithms or other operations disclosed herein. The system can include a computing device 1202. In some embodiments, the computing device 1202 can include at least one memory storage medium 1210 and at least one processor 1220. In some embodiments, the computing device 1202 can include a user interface 1230. The system 1200 can include an imaging device 1240 operably coupled thereto. Aspects of system components are described in more detail below.

In some embodiments, the computing device 1202 can include one or more of a personal computer, a network of computers, one or more servers, a laptop computer, a tablet computer, or a cellular phone. In some embodiments, one or more components of the computing device 1202 can be integrated into a microscope (imaging device). In some embodiments, one or more components of the computing device can be located remotely from the imaging device. In such embodiments, the one or more components of the computing device 1202 can be operably coupled to the imaging device 1240 through a wired or wireless connection 1206. In some embodiments, the one or more components of the computing device can be configured to receive images captured by the imaging device indirectly, such as through a disc, flash drive, e-mail, or other means.

The at least one memory storage medium 1210 can include one or more of a hard drive, a solid state drive, a disc, or any other tangible, non-transitory memory storage device. The at least one memory storage medium 1210 can include any of the modules or submodules disclosed herein as machine-readable and executable program stored thereon. In some embodiments, the system 1200 can include a plurality of memory storage mediums 1210 each having one or more modules or submodules stored thereon.

The at least one processor 1220 can be configured to read and execute one or more programs stored in the at least one memory storage medium 1210. For example, the at least one processor 1220 can be configured to read and execute one or more of any of the modules or submodules disclosed herein. In some embodiments, the at least one processor 1220 can include a plurality of processors. In such embodiments, each of the plurality of processors can be configured to read and execute one or more modules or submodules stored on the at least one storage medium 1220. In some embodiments, each of a plurality of processors 1220 can be operably coupled to a corresponding one of a plurality of memory storage mediums 1220, and be dedicated to and configured to run only one of the modules or submodules herein.

In some embodiments, the user interface 1230 can include one or more of a display screen, a keyboard, a touch screen, one or more indicators (e.g., lights, buzzers, speakers, etc.), or one or more buttons (e.g., power or start buttons). In some embodiments, the user interface can be physically connected to the computing device. In some embodiments, the user interface 1230 can be configured to display output or input from any of the modules or submodules disclosed herein. For example, the user interface 1230 can be configured to display one or more of a diagnosis, parasitemia, or any data or images disclosed herein. In some embodiments, the user interface can be configured to accept input from a user, such as via a keyboard, USB port, etc. The user interface 1230 can be operably coupled to the computing device via a wired or wireless connection. In some embodiments, the user interface 1230 can be located remotely from the computing device 1202, such as on a computer, tablet computer, or cellular phone remote from the computing device 1202. In such embodiments, one or more of the modules can be performed remotely from the user interface 1202.

In some embodiments, the computing device 1202 can include a power source 1208. The power source 1208 can include one or more of a battery (e.g., lithium ion battery, a lead acid battery, a Nickel Cadmium battery, or any other suitable battery), a solar cell, or an electrical plug (e.g., wall plug). The power source 1208 can be operably coupled to and configured to provide power to any of the components of the system 1200.

The imaging device 1240 can include a microscope, such as a high power microscope including a digital image recorder thereon. The digital imaging device 1240 can be configured to hold a sample slide 1250 thereon. The digital imaging device 1240 can include a high power lens and a digital image recorder to capture one or more high resolution images of a sample slide. The one or more high resolution images can include images of one or more FoVs and images of one or more focal planes of each FoV of the sample slide 1250. The imaging device can be directly coupled (e.g., wired or wirelessly connected) or indirectly coupled (e.g., via a computer network) to the computing device (e.g., to one or more of the memory storage medium(s), processor(s), or user interface of the computing device). In such embodiments, the imaging device 1240 can be configured to output one or more sample images to the at least one memory storage medium 1210 or at least one processor 1220. In some embodiments, the imaging device 1240 can be configured to respond to one or more instructions from the computing device (or a component thereof such as the processor). In such embodiments, the imaging device 1240 can operate based at least in part on operating instructions stored in the at least one memory storage medium 1210 and executed by the at least one processor 1220. For example, the imaging device 1220 can change the distance between or number of focal planes or FoVs based at least in part on instructions from the computing device 1202.

Any of the individual modules or submodules disclosed herein can be stored on, include, or be applied using a machine learning device or computer as disclosed herein.

In some embodiments, a computer system for determining a presence of an analyte in blood can include at least one memory storage medium configured to store a plurality of images of a sample slide. The plurality of images can include a plurality of fields-of-view, each including a unique x and y coordinate of the sample slide, and a plurality of focal planes, each having a unique z coordinate of the sample slide. The memory storage medium can include operational instructions (e.g., one or more modules) stored therein. The computer system can include at least one processor operably coupled to the at least one memory storage medium. The at least one processor can execute one or more machine readable instructions stored in the memory storage medium. The one or more machine readable instructions can include one or more modules or submodules as disclosed herein, which may be executed by a single processor or each by an individual processor dedicated to said module. The at least one processor can determine and apply a white balance transform to each of the plurality of images effective to produce a plurality of color-corrected images as disclosed herein. The at least one processor can determine and apply an adaptive grayscale transform to each of the plurality of images to provide an adaptive grayscale intensity image for each of the plurality of images as disclosed herein. The at least one processor can detect and identify one or more candidate objects in color-corrected images and adaptive grayscale intensity images as disclosed herein. The at least one processor can perform an adaptive thresholding operation on the adaptive grayscale intensity images and output one or more candidate objects based thereon as disclosed herein. The at least one processor can cluster the one or more detected candidate objects into clusters including one or more adjacent candidate objects per cluster and associate (e.g., aggregate) clusters of detected candidate objects indicating that a cluster of one or more adjacent candidate objects are a single candidate object and output locations of the clusters of one or more adjacent candidate objects. The locations can include one or more image patches containing the one or more adjacent candidate objects as disclosed herein. The at least one processor can locate the focal plane having a best focus for each single candidate object as disclosed herein. The at least one processor can determine attributes (e.g., color, roundness, shape) of each single candidate object in the focal plane having the best focus for each single candidate object as disclosed herein. The at least one processor can filter each single candidate object based at least in part on one or more determined attributes as disclosed herein. The at least one processor can extract and output one or more image patches each containing at least one filtered single candidate object of the one or more candidate objects as disclosed herein.

The systems disclosed herein can include the candidate object detection module and blob detection module therein (e.g., having the threshold determination submodule and blob identification submodule) to determine the local adaptive threshold of grayscale intensity for at least some windows of a plurality of windows in the plurality of fields-of-view and plurality of focal planes in the adaptive grayscale images by locally estimating a noise floor in one or more windows of in the adaptive grayscale intensity images, as disclosed herein. The candidate object detection module (e.g., blob identification module therein) can identify one or more blobs in the adaptive grayscale intensity images, based at least in part on the local adaptive threshold(s), as disclosed herein.

The computer systems disclosed herein can include machine readable programs to direct (and the systems can perform) any of the acts disclosed herein. The systems can include one or more imaging devices (e.g., microscopes fitted with cameras). Such systems can provide automated detection of parasites (e.g., malaria) in a sample at concentrations far below concentrations currently utilized. Such systems can allow for early detection (e.g., at low parasitemia) and early treatment of illnesses (e.g., malaria) not previously possible with an automated system. The systems herein allow for reliable, early detection of parasites without the presence of a trained human microscopist.

G. Methods of Diagnosing an Analyte

Figure 13:
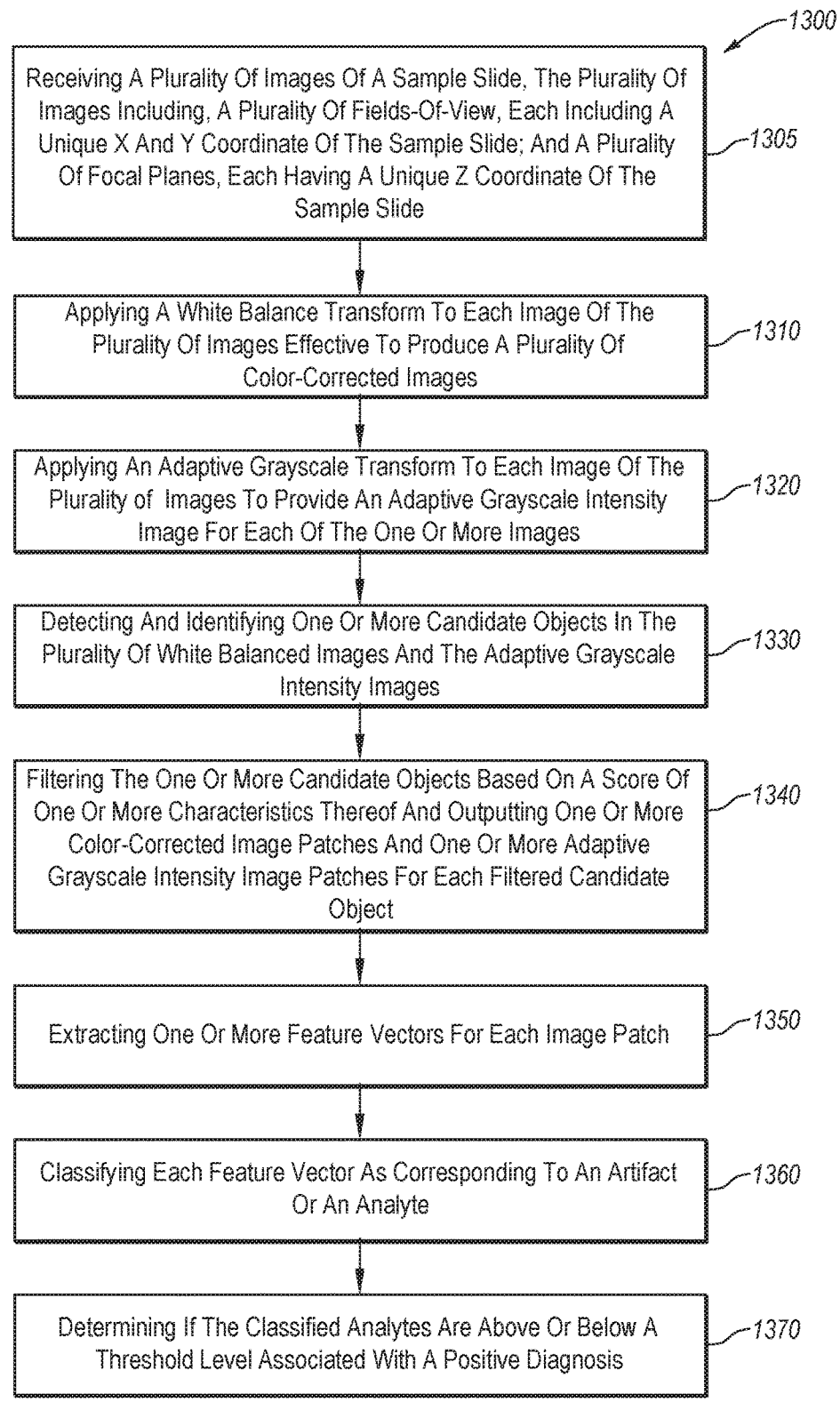
FIG. 13 is a flow diagram of a method for determining the presence of an analyte in a sample, according to an embodiment.

FIG. 13 is a flow diagram of a method 1300 for determining the presence of an analyte in a sample, according to an embodiment. Methods and individual acts for diagnosing an analyte in a sample are also described above with respect to each of the modules and submodules disclosed herein and, in the interest of brevity, are not repeated verbatim with respect to the method 1300. The method 1300 includes using a plurality of images of a sample slide to determine the presence of an analyte in a sample. The method 1300 can include an act 1305 of receiving a plurality of images of a sample slide, such as with a memory storage medium or processor. The plurality of images can include a plurality of FoVs, each including a unique x and y coordinate of the sample slide; and plurality of focal planes, each having a unique z coordinate of the sample slide. The method 1300 can include using one or more components of the system 1200 to perform any of the acts disclosed herein.

The method 1300 can include an act 1310 of applying a white balance transform to each image of the plurality of images effective to produce a plurality of color-corrected images. The method 1300 can include an act 1320 of applying an adaptive grayscale transform to each image of the plurality of images to provide an adaptive grayscale intensity image for each of the plurality of images. The method 1300 can include an act 1330 of detecting and identifying one or more candidate objects in the plurality of color-corrected (e.g., white-balanced) images and the adaptive grayscale intensity images. The method 1300 can include an act 1340 of filtering the one or more candidate objects based at least in part on a score of one or more characteristics thereof, and outputting one or more color-corrected image patches and one or more adaptive grayscale intensity image patches. The method 1300 can include an act 1350 of extracting one or more feature vectors from the color-corrected image patches and the adaptive grayscale intensity image patches and outputting the one or more feature vectors. The method 1300 can include an act 1360 of classifying each feature vector as corresponding to an artifact or an analyte. The method 1300 can include an act 1370 of determining if the classified feature vectors are above or below a threshold level associated with a positive diagnosis. Each of the acts 1310-1370 is discussed in more detail below.

The act 1310 of applying a white balance transform to each image of the plurality of images effective to produce a plurality of color-corrected images can be carried out using any of the techniques disclosed with respect to the image preprocessing module 310 disclosed above. For example, the act 1310 can include selecting a plurality of brightest pixels from a subset of the plurality of images selected such that the probability of the presence of a clear pixel being located in the subset approaches (is substantially) 1 as disclosed herein. The act 1310 can include calculating and applying a standard grayscale intensity of each pixel of the subset of images to determine the plurality of brightest pixels in each image of the subset of the plurality of images as disclosed herein. The act 1310 can include determining a red value R, a green value G, and a blue value B of each of the plurality of brightest pixels as disclosed herein. The act 1310 can include calculating an average color vector defined by an average color of the plurality of brightest pixels as disclosed herein. The act 1310 can include determining a white color vector and determining an axis vector that is perpendicular to, and calculated from the cross-product of both the average color vector and the white color vector. The act 1310 can in include computing an affine transform matrix from the axis vector and the angle between the white vector and the average color vector; and applying the affine transform matrix to each pixel in each image of the plurality of images to provide a plurality of color-corrected images.

The act 1320 of applying an adaptive grayscale transform to each image of the plurality of images to provide an adaptive grayscale intensity image for each of the plurality of image can be carried out using any of the techniques disclosed with respect to the image preprocessing module 310 disclosed above. For example, the act 1320 can include receiving as input a plurality of color-corrected images and standard grayscale intensity images and thresholding the standard grayscale intensity images at a dark threshold selected to detect blobs that may potentially be white blood cell nuclei. The act 1320 can include filtering the potential white blood cell nuclei blobs by attributes (e.g., color, area, or shape filters) to identify white blood cell nuclei as disclosed herein. The act 1320 can include outputting as white blood cell vector data a red value R, a green value G, and a blue value B of one or more pixels from the input color-corrected images that contain a while blood cell nuclei therein. The act 1320 can include outputting as background vector data, a red value R, a green value G, and a blue value B of a plurality of qualified background pixels as determined from a random sampling of pixels that are brighter in grayscale intensity than the dark threshold, in the color-corrected images. The act 1320 can include determining an adaptive grayscale projection vector from the white blood cell vector data and background vector data. The act 1320 can include outputting a plurality of adaptive grayscale intensity images.

The act 1330 of detecting and identifying one or more candidate objects in the plurality of color-corrected images and the adaptive grayscale intensity images can be carried out using any of the techniques disclosed with respect to the candidate object detection module 320 disclosed above. For example, detecting and identifying one or more candidate objects can include determining one or more potential analyte locations based upon one or more of a plurality of color-corrected images or a plurality of adaptive grayscale intensity images. The act 1330 can include determining which FoVs of the plurality of FoVs include one or more candidate objects therein. The act 1330 can include clustering of the one or more candidate objects therein to provide a candidate object cluster defined by the adjacent (e.g., nearby or overlapping) candidate objects therein. Clustering is based at least in part on the proximity or distance between candidate objects. The act 1330 can include determining the focal plane having a best focus score for each candidate object of the one or more candidate objects, as disclosed herein.

The act 1340 of filtering the one or more candidate objects based at least in part on a score of one or more characteristics thereof, and outputting one or more color-corrected image patches and one or more adaptive grayscale intensity image patches can be carried out using any of the techniques disclosed with respect to the candidate object detection module 320 disclosed above. The act 1340 can include outputting a score of one or more characteristics of each of the one or more candidate objects, the one or more characteristics including at least one of area, grayscale intensity, shape, or color. The act 1340 can include filtering the candidate objects based at least in part on the score which is based at least in part on the one or more characteristics. Filtering the one or more candidate objects can include comparing the score based at least in part on one or more characteristics of the one or more candidate objects to a threshold score based at least in part on the one or more characteristics. Filtering the candidate objects can include outputting the one or more candidate objects with a score above the threshold score as potential analyte locations and rejecting the one or more candidate objects with a score below the threshold score. The act 1340 can include outputting adaptive grayscale and color-corrected image patches and associated focal planes having potential analyte locations therein.

The act 1350 of extracting one or more feature vectors from the color-corrected image patches and the adaptive grayscale intensity image patches and outputting the one or more feature vectors can be carried out using any of the techniques disclosed with respect to the feature extraction module 330 disclosed above. For example, the act 1350 can include receiving as input a plurality of color-corrected image patches and a plurality of adaptive grayscale intensity image patches corresponding to the one or more potential analyte locations in the plurality of images and outputting one or more feature vectors each representing a potential analyte. The act 1350 can include receiving the one or more color-corrected image patches and one or more adaptive grayscale intensity image patches and teaching the CNN a set of weights based at least in part on the one or more ground truth image patches. In some embodiments, teaching the set of weights includes augmenting one or more ground truth images (e.g., image patches) using a data augmentation scheme. The data augmentation scheme can include a random gamma correction of one or more of a red, green, blue, or grayscale intensity component of the ground truth image patches. In some embodiments, teaching a set of weights to a CNN may include accepting as ground truth one or more annotated images of the analyte in ground truth samples and one or more annotated images of artifacts in ground truth samples. The annotated images may include known analytes and artifacts configured to train the CNN to recognize characteristics of the same. In some embodiments, accepting as ground truth one or more annotated images of the analyte in ground truth samples and one or more annotated images of artifacts in ground truth sample can include teaching a machine learning classifier a set of weights based at least in part on the one or more ground truth image patches. The act 1350 can include determining and extracting one or more features (e.g., one or more of manual features or automatic features) of one or more candidate objects in the plurality of color-corrected images and the plurality of adaptive grayscale intensity images corresponding to the one or more potential analyte locations. The act 1350 can include representing the one or more extracted features as the one or more feature vectors.

The act 1360 of classifying each feature vector as corresponding to an artifact or an analyte can be carried out using any of the techniques disclosed with respect to the object classifier module 340 disclosed above. For example, the act 1360 can include receiving as input one or more feature vectors of candidate objects and classifying the one or more feature vectors as corresponding to one of the artifact or the analyte. The classifying can be carried out by scoring the feature vectors with a machine learning classifier that has been trained with a set of ground truth images or associated vectors as disclosed above, with high scores (e.g., high probabilities) being classified as the analyte and low scores (e.g., low probabilities) being classified as something other than the analyte, such as background or an artifact. In some embodiments, classifying the one or more feature vectors can include averaging the scores of the machine learning classifier over the feature vectors corresponding to augmented versions of each of the color-corrected image patches and the adaptive grayscale intensity image patches. In some embodiments, the method may include outputting one or more image patches containing candidate objects (e.g., classified as analyte or artifact) therein for examination by human users. Such image patches can be output to a user interface, such as a computer screen.

The act 1370 of determining if the classified feature vectors are above or below a threshold level associated with a positive diagnosis can be carried out using any of the techniques disclosed with respect to the diagnosis module 350 disclosed above. For example, determining if the classified analytes are above or below a threshold level associated with a positive diagnosis can include determining if the analyte is present and giving an indication of the presence or absence of the analyte based upon an amount of one or more feature vectors that are classified as the analyte, or a relation thereof to a threshold value or a background noise value. In an embodiment, the method 1300 can include outputting a diagnosis or analyte concentration, such as to the user interface (e.g., displaying the diagnosis of analyte concentration).

In some embodiments, the method 1300 can include an act of obtaining a sample from a subject, such as obtaining a blood sample. In some embodiments, the method 1300 can include smearing the sample on a sample slide. In some embodiments, the method 1300 can include taking a plurality of images of a sample slide. The plurality of (sample) images can include multiple FoVs and focal planes. In an embodiment, the method 1300 can include outputting the plurality of (sample) images from the image device. The method 1300 can include receiving the plurality of (sample) images at the computing device.

In some embodiments, the method 1300 can include determining the concentration or amount of analyte in a sample (e.g., parasitemia). In some embodiments, the analyte can include a parasite such as malaria, boa loa, borrelia, helminth, tuberculosis, trypanosomiasis, or any other parasite. In some embodiments, the systems and methods herein can be used to detect specific parasite (e.g., malaria) conformations or species based upon one or more characteristics thereof.

In simplified terms, a method of detecting an analyte in a sample can include accepting as ground truth a set of annotated images of an analyte (e.g., malaria parasites) in biological samples from a geographic location. The method can include accepting a set of uncharacterized images from an automated microscope device, the uncharacterized images obtained from biological samples taken in the geographic location. The method can include preprocessing the set of uncharacterized images to create a set of images with consistent color appearance. The method can include subjecting the set of images with consistent color appearance to a candidate location classification to generate a set of candidate object images. The method can further include subjecting the set of candidate object images to a parasite detection classification based in part on the ground truth to generate a set of labelled objects. The method can include subjecting the set of labelled objects to a segmentation analysis depicting structures (e.g., nucleus and cytoplasm) in each of the set of labelled objects. The method can include performing feature extraction analysis on each of the set of labelled objects. The method can further include classifying each of the labelled objects with a classifier score related to the probability of the analyte (e.g., malaria parasite) being present in each of the labelled objects. In some embodiments, the method 1300 can include importing ground truth data associated with one or more candidate parasite species from memory storage based at least in part on meta-data corresponding to one or more of a geographic location, season, or other criteria associated with a sample, and use the same to determine or identify a species, stage, or type of parasite in a sample as disclosed above.

Figure 14:
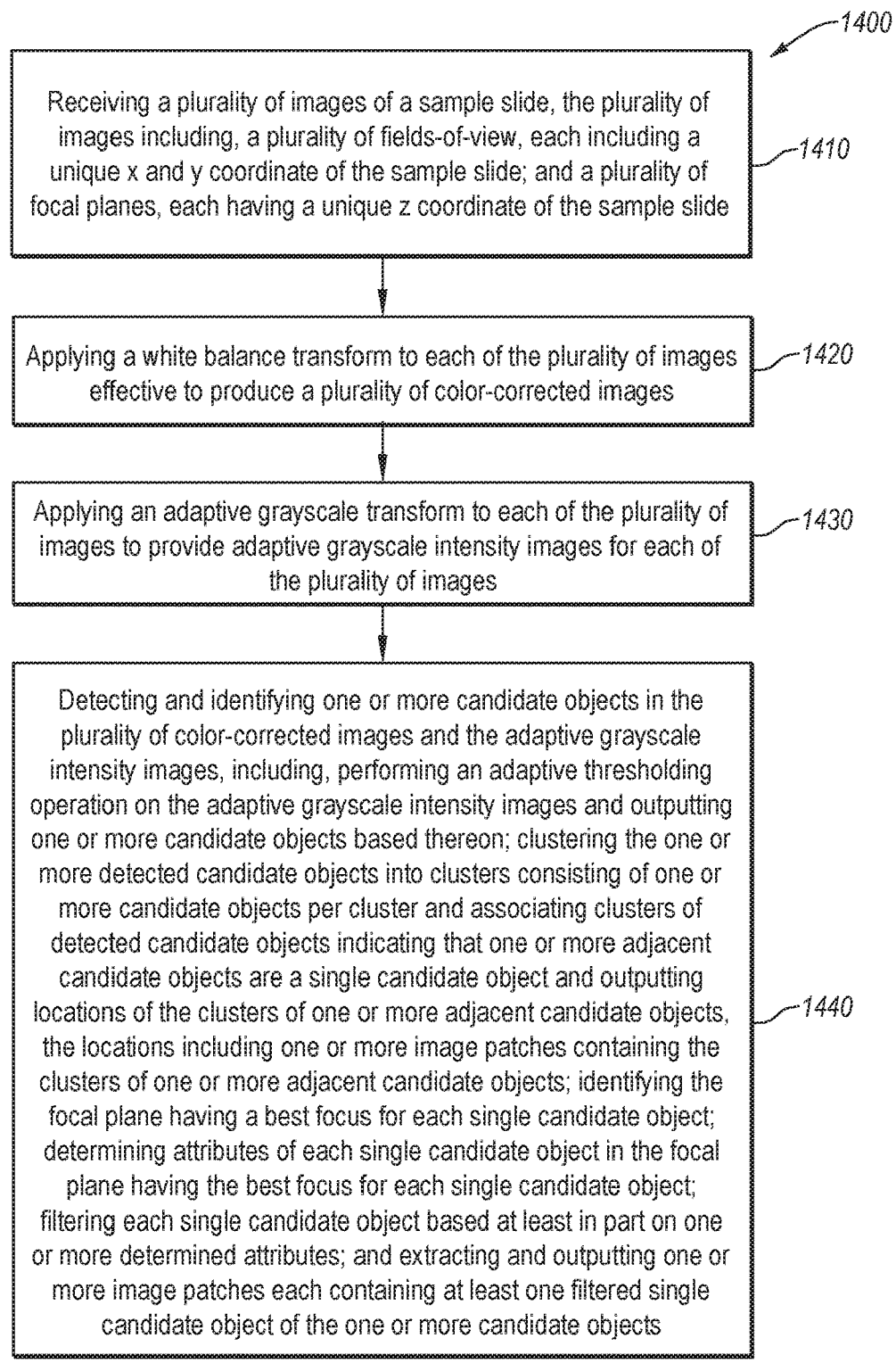
FIG. 14 is a flow diagram of a method for determining the presence of an analyte in a sample, according to an embodiment.

FIG. 14 is a flow diagram of a method 1400 for determining the presence of an analyte in a sample. Methods and individual acts for diagnosing an analyte in a sample are also described above with respect to each of the modules and submodules disclosed herein and, in the interest of brevity, are not repeated verbatim with respect to the method 1400. The method 1400 can include an act 1410 of receiving a plurality of images of a sample slide, the plurality of images including, a plurality of fields-of-view, each including a unique x and y coordinate of the sample slide; and a plurality of focal planes, each having a unique z coordinate of the sample slide. The method 1400 includes an act 1420 of applying a white balance transform to each of the plurality of images effective to produce a plurality of color-corrected images. The method 1400 includes an act 1430 of applying an adaptive grayscale transform to each of the plurality of images to provide adaptive grayscale intensity images for each of the plurality of images. The method 1400 includes an act 1440 of detecting and identifying one or more candidate objects in the plurality of color-corrected images and the adaptive grayscale intensity images. The act 1440 includes performing an adaptive thresholding operation on the adaptive grayscale intensity images and outputting one or more candidate objects based thereon. The act 1440 includes clustering the one or more detected candidate objects into clusters including one or more candidate objects per cluster, associating clusters of detected candidate objects indicating that one or more adjacent candidate objects are a single candidate object, and outputting locations of the clusters of one or more adjacent candidate objects, the locations including one or more image patches containing the clusters of one or more adjacent candidate objects. The act 1440 includes identifying the focal plane having a best focus for each single candidate object; determining attributes of each single candidate object in the focal plane having the best focus for each single candidate object. The act 1440 includes filtering each single candidate object based at least in part on one or more determined attributes. The act 1440 includes extracting and outputting one or more image patches each containing at least one filtered single candidate object of the one or more candidate objects. In embodiments, one or more of the acts of the method 1400 can be omitted or performed in a different order than provided above. For example, the act 1410 can be omitted.

The method 1400 can include an act 1410 of receiving a plurality of images of a sample slide, the plurality of images including, a plurality of fields-of-view, each including a unique x and y coordinate of the sample slide; and a plurality of focal planes, each having a unique z coordinate of the sample slide. In embodiments, receiving a plurality of images of a sample slide can include receiving the plurality of images from a microscope associated with a computer vision system, such as the system 1200 or any of the systems disclosed herein. In embodiments, receiving a plurality of images of a sample slide can include receiving the plurality of images at an image preprocessing module.

The method 1400 includes an act 1420 of applying a white balance transform to each of the plurality of images effective to produce a plurality of color-corrected images. The act 1420 of applying a white balance transform to each of the plurality of images effective to produce a plurality of color-corrected images can be similar or identical to act 1310 disclosed above in one or more aspects. For example, the act 1420 of applying a white balance transform to each of the plurality of images effective to produce a plurality of color-corrected images can be carried out using any of the techniques disclosed herein with respect to the image preprocessing module 310. For example, the act 1420 can include selecting a plurality of brightest pixels from a subset of the plurality of images selected such that the probability of the presence of a clear pixel being located in the subset approaches (is substantially) one, as disclosed herein. The act 1420 can include calculating and applying a standard grayscale intensity of each pixel of the subset of images to determine the plurality of brightest pixels in each image of the subset of the plurality of images as disclosed herein. The act 1420 can include determining a red value R, a green value G, and a blue value B of each of the plurality of brightest pixels as disclosed herein. The act 1420 can include calculating an average color vector defined by an average color of the plurality of brightest pixels as disclosed herein. The act 1420 can include determining a white color vector and determining an axis vector that is perpendicular to, and calculated from the cross-product of both the average color vector and the white color vector. The act 1420 can in include computing an affine transform matrix from the axis vector and the angle between the white vector and the average color vector; and applying the affine transform matrix to each pixel in each image of the plurality of images to provide a plurality of color-corrected images. In embodiments, applying the white balance transform can include applying the white balance transform to a color vector of each pixel of the plurality of images defined by the red value R, green value G, and blue value B therein, and outputting the color-corrected images based thereon.

The method 1400 includes an act 1430 of applying an adaptive grayscale transform to each of the plurality of images to provide adaptive grayscale intensity images for each of the plurality of images. The act 1430 of applying an adaptive grayscale transform to each image of the plurality of images to provide an adaptive grayscale intensity image for each of the plurality of image can be carried out using any of the techniques disclosed herein with respect to the image preprocessing module 310. For example, the act 1430 can include one or more of receiving as input a plurality of color-corrected images and standard grayscale intensity images; thresholding the standard grayscale intensity images at a dark threshold to detect one or more blobs; filtering at least one of color, area, or shape of the detected one or more blobs to locate and identify white blood cell nuclei at high sensitivity and specificity; outputting as white blood cell vector data a red value R, a green value G, and a blue value B of one or more pixels from the color-corrected images that contain a while blood cell nuclei therein; outputting as background vector data, a red value R, a green value G, and a blue value B of a plurality of qualified background pixels as determined from a random sampling of pixels that are brighter in grayscale intensity than the dark threshold (or darker in grayscale intensity than a brightness threshold for non-inverted grayscale intensity images) in the color-corrected images; or determining an adaptive grayscale projection vector from the white blood cell vector data and background vector data. The act 1430 can include applying the adaptive grayscale transform to one or more of the plurality of images or portions thereof to provide one or more adaptive grayscale intensity images. In embodiments, applying an adaptive grayscale transform to the plurality of images can include outputting a plurality of adaptive grayscale intensity images, such as to the candidate object detection module (or threshold determination submodule therein).

In embodiments, applying an adaptive grayscale transform can include determining and applying an adaptive grayscale projection as a vector using a plurality of white blood cell pixels, a plurality of qualified background pixels, and a regression (e.g., using any of the regression techniques disclosed herein). In embodiments, applying an adaptive grayscale transform can include calculating and applying an adaptive grayscale projection vector to each of the plurality of color-corrected images effective to provide a plurality of adaptive grayscale intensity images. Applying an adaptive grayscale transform can include receiving as input a plurality of color-corrected images and standard grayscale intensity images and determining a local adaptive grayscale intensity for one or more portions thereof (e.g., windows, FoVs, image patches). The act 1430 can include using local adaptive grayscale intensity to determine an adaptive grayscale transform for the image(s).

The act 1430 can include filtering the potential WBC nuclei blobs by attributes (e.g., color, area, or shape filters) to identify WBC nuclei as disclosed herein. Filtering the potential WBC nuclei blobs by attributes can include thresholding the standard grayscale intensity images at a dark threshold to detect blobs that may potentially be WBC nuclei. The act 1430 can include outputting as WBC vector data a red value R, a green value G, and a blue value B of one or more pixels from the input color-corrected images that contain a WBC nuclei therein. The act 1430 can include outputting as background vector data, a red value R, a green value G, and a blue value B of a plurality of qualified background pixels as determined from a random sampling of pixels that are brighter in grayscale intensity than the dark threshold, in the color-corrected images. The act 1430 can include determining an adaptive grayscale projection vector from the WBC vector data and background vector data. The act 1430 can include outputting a plurality of adaptive grayscale intensity images and WBC detection masks.

The method 1400 includes an act 1440 of detecting and identifying one or more candidate objects in the plurality of color-corrected images and the adaptive grayscale intensity images. The act 1440 can include performing an adaptive thresholding operation on the adaptive grayscale intensity images and outputting one or more candidate objects based thereon. The act 1440 can include clustering the one or more detected candidate objects into clusters including one or more candidate objects per cluster, associating (e.g., aggregating) clusters of detected candidate objects indicating that one or more adjacent candidate objects are a single candidate object, and outputting locations of the clusters of one or more adjacent candidate objects, the locations including one or more image patches containing the clusters of one or more adjacent candidate objects. The act 1440 can include identifying the focal plane having a best focus for each single candidate object and determining attributes of each single candidate object in the focal plane having the best focus for each single candidate object. The act 1440 can include filtering each single candidate object based at least in part on one or more determined attributes. The act 1440 can include extracting and outputting one or more image patches each containing at least one filtered single candidate object of the one or more candidate objects.

Performing an adaptive thresholding operation on the adaptive grayscale intensity images and outputting one or more candidate object cluster (blob) detection masks based thereon can include determining an adaptive threshold (e.g., local adaptive grayscale intensity threshold as differentiated from an adaptive grayscale image) for one or more windows of an FoV or image. For example, performing an adaptive thresholding operation can include determining an adaptive threshold using any of thresholding techniques disclosed herein with respect to FIGS. 8A-8G. For example, performing an adaptive thresholding operation can include determining the adaptive (grayscale intensity) threshold for an image or portion(s) thereof, and applying the adaptive threshold to determine if any pixels exceed or fall short of the adaptive threshold, such pixels indicating the presence of an object of interest (e.g., candidate object and/or blob).

In embodiments, performing an adaptive thresholding operation can include receiving one or more one or more adaptive grayscale intensity images and receiving a one or more WBC detection masks that include information about locations of WBCs in the plurality of fields-of-view and plurality of focal planes. Further, performing an adaptive thresholding operation can include determining a local adaptive threshold of grayscale intensity for one or more regions in the adaptive grayscale intensity images using the one or more adaptive grayscale intensity images and WBC detection mask. For example, determining a local adaptive threshold of grayscale intensity for one or more regions in the adaptive grayscale intensity images can include determining the local adaptive (grayscale intensity) threshold for at least some windows of a plurality of windows in the plurality of fields-of-view and plurality of focal planes in the adaptive grayscale images, including at least some windows containing one or more candidate objects therein, by locally estimating a noise floor of the at least some of the windows. Determining an adaptive threshold can include determining a noise floor for a window, image patch, or FoV, and selecting an adaptive threshold based thereon. The adaptive threshold may be set at the noise floor, or some value above or below the noise floor (e.g., the noise floor plus some delta grayscale intensity thereabove).

Locally estimating the noise floor of at least some of the windows can be carried using the estimation techniques disclosed above with respect to FIGS. 8A-8G. For example, locally estimating the noise floor in at least some windows can be carried out by determining the median grayscale intensity of the pixels in each of the at least some windows. In embodiments, locally estimating the noise floor of at least some of the windows can include determining a median pixel grayscale intensity value in each of the at least some windows in the adaptive grayscale intensity images, discounting any variations in the median pixel grayscale intensity value due to presence of WBCs, such as by replacing the value of the pixels of WBCs with an image-wide, FoV-wide, or window-wide median grayscale intensity value. For example, determining a median pixel grayscale intensity value in each of the at least some windows in the adaptive grayscale intensity images can include receiving information noting a presence and location of WBCs within one or more identified windows of a field-of-view of the plurality of fields-of-view (e.g., from a WBC detection mask). When a WBC is indicated as present, determining a median pixel grayscale intensity value can include replacing pixels containing the WBC in a specific region of the one or more identified windows of the field-of-view with a replacement median grayscale pixel intensity value determined from all pixels in the field-of-view. In embodiments, determining a median pixel grayscale intensity value in each of the at least some windows in the adaptive grayscale intensity images can further include determining a local median pixel grayscale intensity value for all pixels in each of the one or more identified windows after WBC pixels have been replaced by the replacement median grayscale intensity value. This median grayscale intensity is the noise floor. The noise floor can be set as the local adaptive (grayscale intensity) threshold, or can be modified by some delta in grayscale intensity to set the adaptive threshold above or below the noise floor. In embodiments, determining a median pixel grayscale intensity value in each of the at least some windows in the adaptive grayscale intensity images can further include outputting the local adaptive threshold for each of the one or more identified windows. The local adaptive threshold of a window, image patch, or FoV may be based on the local median grayscale intensity value therein. For example, the local adaptive threshold may be the local median grayscale intensity value (e.g., noise floor) or some value thereabove or therebelow.

In embodiments, the method 1400 can further include applying a local adaptive threshold to each of the at least some windows of the adaptive grayscale intensity images. In embodiments, applying the local adaptive threshold(s) to corresponding image patches of the plurality of fields-of-view includes determining a presence of one or more candidate objects in the corresponding image patches, the one or more candidate objects having a grayscale intensity above or below the local adaptive threshold depending on whether the grayscale intensity of the image patches has been inverted. For example, applying the local adaptive threshold to each of the at least some windows of the adaptive grayscale intensity images and determining a presence of one or more candidate objects in the corresponding image patches can include determining if any pixels in the at least some windows have a grayscale intensity value that is below (or above, for inverted grayscale intensities) the local adaptive threshold. Pixels having a grayscale intensity value that is below (or above, for inverted grayscale intensity images) the local adaptive threshold can indicate the presence of an object of interest (e.g., candidate object) at the pixel. For example, determining a presence of one or more candidate objects in the corresponding image patches, can include determining the presence of one or more candidate objects (as indicated by grayscale intensity values for pixels corresponding thereto) having a grayscale intensity below the local adaptive threshold. In embodiments, determining the presence of one or more candidate objects having a grayscale intensity below the local adaptive threshold can include determining the presence of the one or more candidate objects in each image patch below the local adaptive threshold based upon a darkness threshold of the adaptive grayscale intensity images (e.g., pixels below the darkness threshold indicate an object of interest). In embodiments, the method can include inverting a brightness of the adaptive grayscale intensity images to produce a plurality of inverted grayscale intensity images, determining the local adaptive threshold based upon the plurality of inverted grayscale intensity images, and determining the presence of the one or more candidate objects in each image patch above the local adaptive threshold based upon a brightness threshold of the plurality of inverted grayscale images (e.g., brighter pixels indicate objects of interest). The pixels having values above (or below depending on whether or not the grayscale intensity is inverted) can be output as objects of interest (e.g., candidate objects).

In embodiments, applying an adaptive grayscale transform to each of the plurality of images to provide adaptive grayscale intensity images for each of the plurality of images, performing an adaptive thresholding operation on the adaptive grayscale intensity images, and outputting one or more candidate object cluster detection masks (e.g., detection masks 811, FIG. 8B) based thereon can be performed by a blob detection submodule as disclosed herein.

In embodiments, the method 1400 can include clustering the one or more detected candidate objects into clusters including one or more candidate objects per cluster and associating (e.g., grouping) clusters of detected candidate objects to indicate that one or more adjacent candidate objects are a single candidate object. In embodiments, the method 1400 can include outputting locations of the clusters of one or more adjacent candidate objects (e.g., blobs), the locations including one or more image patches containing the clusters of one or more adjacent candidate objects. In embodiments, associating clusters of detected candidate objects indicating that one or more adjacent candidate objects are a single candidate object and outputting locations of the clusters of one or more adjacent candidate objects can include determining which fields-of-view of the plurality of fields-of-view include one or more candidate objects therein, and clustering one or more candidate objects based at least in part on a distance between adjacent candidate objects of the one or more candidate objects in a field-of view to provide a candidate object cluster defined by the adjacent candidate objects therein.

In embodiments, identifying the focal plane having a best focus for each single candidate object can include determining the focal plane with a highest focus score for each image patch having each single candidate object. In embodiments, the method can further include (automatically) selecting and outputting the respective the focal planes with the highest focus score for each candidate object, such as to submodule 840 (e.g., for blob attribute extraction).

In embodiments, the method 1400 can include determining attributes of each single candidate object in the focal plane having the best focus for each single candidate object. Determining attributes of each single candidate object in the focal plane having a best focus for each single candidate object can include determining one or more of an area, a roundness, a shape, or a grayscale intensity of each single candidate object in the focal plane having the best focus for each single candidate object. In embodiments, determining attributes of each single candidate object can include identifying one or more blobs (e.g., in the focal plane(s) having the highest focus score) based on one or more determined attributes or characteristics thereof. For example, the method 1400 can include identifying a darkest blob in the focal plane having the highest focus score for each single candidate object and assigning the darkest blob as a candidate object of interest. The method 1400 can include identifying a roundest blob in the focal plane having the highest focus score for each single candidate object and assigning the roundest blob as a candidate object of interest. In embodiments, the method 1400 can include outputting one or more determined attributes of each single candidate object (in the focal plane having the best focus for each single candidate object) and classifying each single candidate object as an artifact or candidate object based on the one or more determined attributes.

In embodiments, the method 1400 includes filtering each single candidate object based at least in part on one or more determined attributes. For example, filtering each single candidate object based at least in part on one or more determined attributes can include using an artifact classifier configured to score each single candidate object based at least in part on the one or more determined attributes. In embodiments, the method 1400 can include determining a score for each single candidate object based on the one or more determined attributes as disclosed herein. For example, determining a score can include scoring the one or more determined attributes based on known attributes corresponding to known analytes. The known attributes can be used as templates or standards by an artefact filtering submodule (e.g., submodule 850), such as to set a threshold score for the one more attributes. For example, filtering each single candidate object based at least in part on one or more determined attributes can include determining a threshold score based upon attributes of ground truth objects trained into a memory storage medium and accessed by at least one processor, and filtering each single candidate object based on a score of the determined attributes to the threshold score. In embodiments, filtering each single candidate object based at least in part on one or more determined attributes can include discarding single candidate objects with a score below a threshold score and retaining the single candidate objects having a score above the threshold score. The one or more image patches of the single candidate objects that are retained can include small regions of color corrected red, blue, and green color images and adaptive grayscale intensity images of fields-of-view and focal planes that contain at least one single candidate object.

In embodiments, the method 1400 can include extracting and outputting one or more image patches each containing at least one filtered single candidate object of the one or more candidate objects. For example, extracting and outputting can include extracting and outputting one or more image patches of the single candidate objects that are retained (e.g., retained based on the single candidate object having a score above a threshold score). In embodiments, extracting and outputting can include outputting the one or more image patches of the single candidate objects that are retained for feature extraction of the single candidate objects therein (e.g., the single candidate objects that are retained).

In embodiments, the method 1400 can include filtering the one or more candidate objects based at least in part on a score that is based at least in part on one or more characteristics of one or more the single candidate objects and outputting one or more color-corrected image patches and one or more adaptive grayscale intensity image patches for each filtered candidate object. The method 1400 can include extracting one or more feature vectors from the color-corrected image patches and the adaptive grayscale intensity image patches and outputting the one or more feature vectors. In embodiments, extracting the one or more feature vectors from the color-corrected image patches and the adaptive grayscale intensity image patches can include receiving as input a plurality of color-corrected image patches and a plurality of adaptive grayscale intensity image patches corresponding to one or more potential analyte locations in the plurality of images and outputting one or more feature vectors each representing a potential analyte. In embodiments, extracting the one or more feature vectors from the color-corrected image patches and the adaptive grayscale intensity image patches can include determining and extracting one or more features of one or more candidate objects in the plurality of color-corrected image patches and the plurality of adaptive grayscale intensity image patches corresponding to the one or more potential analyte locations and representing one or more features associated with the one or more candidate objects as one or more feature vectors In embodiments, determining and extracting one or more features (e.g., attributes) of the one or more candidate objects includes extracting one or more automatically learned features from the one or more candidate objects. Extracting the automatically learned features can include teaching a machine learning module a set of weights based at least in part on ground truth image patches having one or more ground truth objects therein. The one or more ground truth objects can include samples of the analyte and/or samples of artifacts. The machine learning module includes a convolutional neural network or any other machine learning module. In embodiments, teaching the machine learning module can include accepting as ground truth one or more annotated images of the analyte in ground truth samples and one or more annotated images of artifacts in ground truth samples. In embodiments, teaching the machine learning module a set of weights based at least in part on ground truth image patches can include augmenting the ground truth image patches using a data augmentation scheme. For example, the data augmentation scheme can include a random gamma correction of one or more of a red, green, blue, or grayscale intensity component of the ground truth image patches as disclosed herein.

In embodiments, extracting the one or more feature vectors from the color-corrected image patches and the adaptive grayscale intensity image patches can include determining a best focus plane for each image patch of a plurality of color-corrected image patches and adaptive grayscale intensity image patches containing the one or more candidate objects based at least in part on a best focus score. The best focus score can include a highest score from a plurality of focus scores for the plurality of focal planes in an image patch having a candidate object therein. Extracting the one or more feature vectors from the color-corrected image patches and the adaptive grayscale intensity image patches can include determining a standard deviation of focus scores across all of the plurality of focal planes of each image patch having the candidate object therein, and determining a red-shift score for each image patch based at least in part upon a shift in redness of a darkest portion of a candidate object between the plurality of focal planes in each image patch.

The method 1400 can include classifying each feature vector as corresponding to an artifact or an analyte. In embodiments, classifying each feature vector as corresponding to an artifact or an analyte can include receiving as input one or more feature vectors of candidate objects and classifying the one or more feature vectors as corresponding to one of the artifact or the analyte. The method 1400 can include determining if the feature vectors classified as analytes are above or below a threshold level associated with a positive diagnosis. In embodiments, classifying each feature vector as corresponding to an artifact or an analyte can include using a machine learning classifier that outputs a score indicating that each of the one or more feature vectors of the one or more candidate objects corresponds to an analyte.

In embodiments, outputting of the color-corrected image patches and the adaptive grayscale intensity image patches can include using a data augmentation scheme to augment the color-corrected image patches and the adaptive grayscale intensity image patches and classifying the one or more feature vectors can include averaging output of the machine learning classifier over the feature vectors corresponding to augmented versions of each of the color-corrected image patches and the adaptive grayscale intensity image patches. Any of the data augmentation schemes used herein can be used, such as a random gamma correction of one or more of a color-corrected red, green, blue, or adaptive grayscale intensity component of the color-corrected image patches or the adaptive grayscale intensity image patches.

In embodiments, determining if the feature vectors classified as corresponding to analytes are above or below a threshold level associated with a positive diagnosis can include determining if the analyte is present and outputting an indication of a presence or absence of the analyte based upon an amount of one or more feature vectors that are classified as the analyte (e.g., parasite). In embodiments, the methods herein can include identifying a species of one or more candidate objects based at least in part on one or more image characteristics (e.g., determinate attributes of the candidate object(s)) including one or more of shape, size, or color of the candidate object(s).

In embodiments, the methods disclosed herein can include recording, with a microscope, one or more images of one or more sample slides, such as blood slides.

In embodiments, the methods disclosed herein can be carried out using at least one memory storage medium that includes one or more modules and/or submodules as disclosed herein. For example, the methods disclosed herein can be carried out using each of an image preprocessing module, a candidate object detection module, a feature extraction module, a classification module, and a diagnosis module stored in the memory storage medium as computer readable programs that are executable by at least one processor operably coupled to the at least one memory storage medium. In embodiments, the candidate object detection module can include a candidate object cluster (e.g., blob) detection submodule, a candidate object (e.g., blob) clustering submodule, a best focus detection submodule, a candidate object cluster attribute extraction submodule, an artifact filtering submodule, and a thumbnail extraction submodule, as disclosed above. In embodiments, the candidate object detection clustering submodule can include a threshold determination submodule and a blob identification submodule as disclosed with respect to FIGS. 8A-8G.

In an embodiment, a method for determining a presence and/or concentration of an analyte in blood can include receiving a plurality of images of a sample slide, the plurality of images including, a plurality of fields-of-view, each including a unique x and y coordinate of the sample slide; and a plurality of focal planes, each having a unique z coordinate of the sample slide. The method can include applying a white balance transform to each of the plurality of images effective to produce a plurality of color-corrected images. The method can include applying an adaptive grayscale transform to each of the plurality of images to provide adaptive grayscale intensity images for each of the plurality of images. The method can include detecting and identifying one or more candidate objects in the plurality of color-corrected images and the adaptive grayscale intensity images, including, performing an adaptive thresholding operation on the adaptive grayscale intensity images and outputting one or more candidate object clusters based thereon. Performing an adaptive thresholding operation can include receiving one or more adaptive grayscale intensity images and receiving a white blood cell detection mask that includes information about locations of white blood cells in the plurality of fields-of-view and plurality of focal planes. Performing an adaptive thresholding operation can include determining a local adaptive threshold of grayscale intensity for one or more regions in the adaptive grayscale intensity images using the one or more adaptive grayscale intensity images and the white blood cell detection mask. Determining a local adaptive threshold can include determining the local adaptive threshold for at least some windows of a plurality of windows in the plurality of fields-of-view and plurality of focal planes in the adaptive grayscale images, including at least some windows containing one or more candidate objects therein, by locally estimating a noise floor of the at least some of the windows by determining a median grayscale intensity value in each of the at least some windows in the adaptive grayscale intensity images, discounting any variations in the median pixel grayscale intensity value due to presence of white blood cells. Determining a median grayscale intensity value in each of the at least some windows in the adaptive grayscale intensity images includes receiving information noting a presence and location of white blood cells within one or more identified windows of a field-of-view of the plurality of fields-of-view. Determining a median grayscale intensity value in each of the at least some windows in the adaptive grayscale intensity images includes when a white blood cell is indicated as present, replacing pixels containing the white blood cell in a specific region of the one or more identified windows of the field-of-view with a replacement median grayscale pixel intensity value determined from all pixels in the field-of-view. Determining a median grayscale intensity value in each of the at least some windows in the adaptive grayscale intensity images includes determining a local median grayscale intensity value for all pixels in each of the one or more identified windows after white blood cell containing pixels have been replaced by the replacement median grayscale pixel intensity value. Determining a median grayscale intensity value in each of the at least some windows in the adaptive grayscale intensity images includes outputting the local adaptive threshold for each of the one or more identified windows based on the local median grayscale intensity value therein. Detecting and identifying one or more candidate objects in the plurality of color-corrected images and the adaptive grayscale intensity images includes associating clusters of detected candidate objects indicating that one or more adjacent candidate objects are a single candidate object and outputting the locations of the clusters of one or more adjacent candidate objects, the locations including one or more image patches containing the one or more adjacent candidate objects. Detecting and identifying one or more candidate objects in the plurality of color-corrected images and the adaptive grayscale intensity images identifying the focal plane having a best focus for each single candidate object and determining attributes of each single candidate object in the focal plane having the best focus for each single candidate object. Detecting and identifying one or more candidate objects in the plurality of color-corrected images and the adaptive grayscale intensity images includes filtering each single candidate object based at least in part on one or more determined attributes, and extracting and outputting one or more image patches each containing at least one filtered single candidate object of the one or more candidate objects. The method includes filtering the one or more candidate objects based at least in part on a score that is based at least in part on one or more characteristics thereof and outputting one or more color-corrected image patches and one or more adaptive grayscale intensity image patches for each filtered single candidate object. The method includes extracting one or more feature vectors from the color-corrected image patches and the adaptive grayscale intensity image patches and outputting the one or more feature vectors. The method includes classifying each feature vector as corresponding to an artifact or an analyte. The method includes determining if the feature vectors classified as analytes are above or below a threshold level associated with a positive diagnosis.

Any of the acts, system components, modules, or submodules disclosed herein can be used with any of the embodiments disclosed herein.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one skilled in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electrical systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context can dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

This disclosure has been made with reference to various example embodiments. However, those skilled in the art will recognize that changes and modifications can be made to the embodiments without departing from the scope of the present disclosure. For example, various operational steps, as well as components for carrying out operational steps, can be implemented in alternate ways depending upon the particular application or in consideration of any number of cost functions associated with the operation of the system e.g., one or more of the steps can be deleted, modified, or combined with other steps.

Additionally, as will be appreciated by one of ordinary skill in the art, principles of the present disclosure, including components, can be reflected in a computer program product on a computer-readable storage medium having computer-readable program code means embodied in the storage medium. Any tangible, non-transitory computer-readable storage medium can be utilized, including magnetic storage devices (hard disks, floppy disks, and the like), optical storage devices (CD-ROMs, DVDs, Blu-ray discs, and the like), flash memory, and/or the like. These computer program instructions can be loaded onto a general purpose computer, special purpose computer, or other programmable data processing apparatus to produce a machine, such that the instructions that execute on the computer or other programmable data processing apparatus create a means for implementing the functions specified. These computer program instructions can also be stored in a computer-readable memory that can direct a computer or other programmable data processing apparatus to function in a particular manner, such that the instructions stored in the computer-readable memory produce an article of manufacture, including implementing means that implement the function specified. The computer program instructions can also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

In an embodiment, the printing systems disclosed herein can be integrated in such a manner that the printing systems operate as a unique system configured specifically for function of printing (e.g., three-dimensional printing), and any associated computing devices of the printing systems operate as specific use computers for purposes of the claimed system, and not general use computers. In an embodiment, at least one associated computing device of the printing systems operates as specific use computers for purposes of the claimed system, and not general use computers. In an embodiment, at least one of the associated computing devices of the printing systems are hardwired with a specific ROM to instruct the at least one computing device. In an embodiment, one of skill in the art recognizes that the printing devices and printing systems effects an improvement at least in the technological field of three-dimensional printing.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A system for determining a presence of an analyte in blood, the system comprising:
    at least one memory storage medium configured to store a plurality of images of a sample slide, the plurality of images including,
        a plurality of fields-of-view, each including a unique x and y coordinate of the sample slide; and
        a plurality of focal planes, each having a unique z coordinate of the sample slide;
    at least one processor operably coupled to the at least one memory storage medium, the at least one processor being configured to,
        determine and apply a white balance transform to each of the plurality of images effective to produce a plurality of color-corrected images;
        determine and apply an adaptive grayscale transform to each of the plurality of images to provide an adaptive grayscale intensity image for each of the plurality of images;
        detect and identify one or more candidate objects in the color-corrected images and the adaptive grayscale intensity images, and the at least one processor is further configured to,
            perform an adaptive thresholding operation on the adaptive grayscale intensity images and output one or more candidate objects based thereon;
            cluster the one or more detected candidate objects into clusters including one or more adjacent candidate objects per cluster and associate clusters of detected candidate objects indicating that a cluster of one or more adjacent candidate objects are a single candidate object and output locations of the clusters of one or more adjacent candidate objects, the locations including one or more image patches containing the one or more adjacent candidate objects;
            locate the focal plane having a best focus for each single candidate object;
            determine attributes of each single candidate object in the focal plane having the best focus for each single candidate object;
            filter each single candidate object based at least in part on one or more determined attributes; and
            extract and output one or more image patches each containing at least one filtered single candidate object of the one or more candidate objects.

2. The system of claim 1, further comprising:
    a threshold determination module configured to determine a local adaptive threshold of grayscale intensity for one or more regions in the adaptive grayscale intensity images and is operably coupled to,
        an image preprocessing module that is configured to receive one or more adaptive grayscale intensity images therefrom; and
        a white blood cell detection module that is configured to receive a white blood cell detection mask therefrom, the white blood cell detection mask including information about locations of white blood cells in the plurality of fields-of-view and plurality of focal planes.

3. The system of claim 2, wherein the threshold determination module is configured to,
    determine the local adaptive threshold of grayscale intensity for at least some windows of a plurality of windows in the plurality of fields-of-view and plurality of focal planes in the adaptive grayscale images, including at least some windows containing one or more candidate objects therein, by locally estimating a noise floor of the at least some of the windows.

4. The system of claim 3, wherein the threshold determination module is configured to locally estimate the noise floor of at least some of the windows by determining a median grayscale intensity value in each of the at least some windows in the adaptive grayscale intensity images, discounting any variations in the median grayscale intensity value due to presence of white blood cells, to produce the local adaptive threshold in each of the at least some windows.

5. The system of claim 4, wherein the threshold determination module is configured to,
    receive information noting a presence and location of white blood cells within one or more identified windows of a field-of-view of the plurality of fields-of-view;
    when a white blood cell is indicated as present, replace pixels containing the white blood cell in a specific region of the one or more identified windows of the field-of-view with a replacement median grayscale intensity value determined from all pixels in the field-of-view;
    determine a local median grayscale intensity value for all pixels in each of the one or more identified windows after white blood cell containing pixels have been replaced by the replacement median grayscale intensity value; and
    output the local adaptive threshold for each of the one or more identified windows based on the local median grayscale intensity value therein.

6. The system of claim 5, wherein the threshold determination submodule is operably coupled to a blob identification submodule configured to receive and apply the local adaptive threshold to each of the adaptive grayscale intensity images corresponding to the at least some windows.

7. The system of claim 2, further including a blob identification submodule operably coupled to the threshold determination submodule, the blob identification submodule is configured to receive one or more local adaptive thresholds from the threshold determination submodule.

8. The system of claim 7, wherein the blob identification submodule is configured to apply the local adaptive threshold to corresponding image patches of the plurality of fields-of-view and determine a presence of one or more candidate objects in the corresponding image patches, the one or more candidate objects having a grayscale intensity below the local adaptive threshold.

9. The system of claim 1, further including a blob detection submodule, wherein the blob detection submodule is configured to,
invert a brightness of the adaptive grayscale intensity images to produce a plurality of inverted grayscale intensity images;
determine the local adaptive threshold of grayscale intensity based upon the plurality of inverted grayscale intensity images; and
determine the presence of the one or more candidate objects in each image patch above the local adaptive threshold based upon a brightness threshold of the plurality of inverted grayscale intensity images.

10. The system of claim 1, wherein;
the at least one processor is configured to determine the focal plane with a highest focus score for each image patch having each single candidate object;
the at least one processor is configured to select and output the respective focal planes with the highest focus score for each candidate object; and
the at least one processor is configured to identify one or more of a roundest blob, a darkest blob, or a specifically sized blob in the focal plane having the highest focus score for each single candidate object and assign one or more of the roundest blob, the darkest blob, or the specifically sized blob as a candidate object of interest.

11. The system of claim 1, wherein the at least one processor is configured to output determined attributes of each single candidate object in the focal plane having the best focus for each single candidate object to classify each single candidate object as an artifact or candidate object based on the one or more determined attributes.

12. The system of claim 11, wherein the at least one processor is further configured as or includes an artifact classifier configured to score each single candidate object based at least in part on one or more determined attribute.

13. The system of claim 12, wherein the at least one processor is configured to discard single candidate objects with a score below a threshold score and retain each single candidate object having a score above the threshold score.

14. The system of claim 13, wherein the at least one processor is configured to extract and output one or more image patches of each single candidate object that is retained.

15. The system of claim 1, wherein the at least one processor is configured to,
determine and apply a white balance transform to each of the plurality of images effective to produce a plurality of color-corrected images;
determine and apply an adaptive grayscale transform to each of the plurality of images to provide an adaptive grayscale intensity image for each of the plurality of images;
extract and score the one or more candidate objects in the one or more image patches based at least in part on one or more characteristics of the one or more candidate objects, filter the one or more candidate objects based at least in part on the score, and output one or more color-corrected image patches and one or more adaptive grayscale intensity image patches for each filtered candidate object;
extract one or more feature vectors from the color-corrected image patches and the adaptive grayscale intensity image patches and output the one or more feature vectors;
classify each of the one or more feature vectors as corresponding to an artifact or an analyte; and
determine if the feature vectors classified as analytes are above or below a threshold level associated with a positive diagnosis.

16. The system of claim 15, wherein the at least one memory storage medium includes an image preprocessing module, a candidate object detection module, a feature extraction module, a classification module, and a diagnosis module stored therein as computer readable programs that are executable by the at least one processor.

17. A method for determining a presence of an analyte in blood, the method comprising:
receiving a plurality of images of a sample slide, the plurality of images including,
a plurality of fields-of-view, each including a unique x and y coordinate of the sample slide; and
a plurality of focal planes, each having a unique z coordinate of the sample slide;
applying a white balance transform to each of the plurality of images effective to produce a plurality of color-corrected images;
applying an adaptive grayscale transform to each of the plurality of images to provide adaptive grayscale intensity images for each of the plurality of images;
detecting and identifying one or more candidate objects in the plurality of color-corrected images and the adaptive grayscale intensity images, including,
performing an adaptive thresholding operation on the adaptive grayscale intensity images and outputting one or more candidate objects based thereon;
clustering the one or more detected candidate objects into clusters including one or more candidate objects per cluster and associating clusters of detected candidate objects indicating that one or more adjacent candidate objects are a single candidate object and outputting locations of the clusters of one or more adjacent candidate objects, the locations including one or more image patches containing the clusters of one or more adjacent candidate objects;
identifying the focal plane having a best focus for each single candidate object;
determining attributes of each single candidate object in the focal plane having the best focus for each single candidate object;
filtering each single candidate object based at least in part on one or more determined attributes; and
extracting and outputting one or more image patches each containing at least one filtered single candidate object of the one or more candidate objects.

18. The method of claim 17, wherein performing an adaptive thresholding operation on the adaptive grayscale intensity images and outputting one or more candidate objects based thereon includes:
receiving one or more adaptive grayscale intensity images and receiving a white blood cell detection mask that includes information about locations of white blood cells in the plurality of fields-of-view and plurality of focal planes; and determining a local adaptive threshold of grayscale intensity for one or more regions in the adaptive grayscale intensity images using the one or more adaptive grayscale intensity images and white blood cell detection mask.

19. The method of claim 18, wherein determining a local adaptive threshold of grayscale intensity for one or more regions in the adaptive grayscale intensity images includes determining the local adaptive threshold for at least some windows of a plurality of windows in the plurality of fields-of-view and plurality of focal planes in the adaptive grayscale images, including at least some windows containing one or more candidate objects therein, by locally estimating a noise floor of the at least some of the windows.

20. The method of claim 19, wherein locally estimating the noise floor of at least some of the windows includes determining a median grayscale intensity value in each of the at least some windows in the adaptive grayscale intensity images, discounting any variations in the median grayscale intensity value due to presence of white blood cells.

21. The method of claim 20, wherein determining a median grayscale intensity value in each of the at least some windows in the adaptive grayscale intensity images includes:
  receiving information noting a presence and location of white blood cells within one or more identified windows of a field-of-view of the plurality of fields-of-view;
  when a white blood cell is indicated as present, replacing pixels containing the white blood cell in a specific region of the one or more identified windows of the field-of-view with a replacement median grayscale intensity value determined from all pixels in the field-of-view;
  determining a local median grayscale intensity value for all pixels in each of the one or more identified windows after white blood cell containing pixels have been replaced by the replacement median grayscale intensity value; and
  outputting the local adaptive threshold for each of the one or more identified windows based on the local median grayscale intensity value therein.

22. The method of claim 21, further comprising applying the local adaptive threshold to each of the at least some windows of the adaptive grayscale intensity images.

23. The method of claim 18, further comprising applying the local adaptive thresholds to corresponding image patches of the plurality of fields-of-view and determining a presence of one or more candidate objects in the corresponding image patches, the one or more candidate objects having a grayscale intensity below the local adaptive threshold.

24. The method of claim 23, further comprising:
  inverting a brightness of the adaptive grayscale intensity images to produce a plurality of inverted grayscale intensity images;
  determining the local adaptive threshold based upon the plurality of inverted grayscale intensity images; and
  determining the presence of the one or more candidate objects in each image patch above the local adaptive threshold based upon a brightness threshold of the plurality of inverted grayscale images.

25. The method of claim 17, wherein identifying the focal plane having a best focus for each single candidate object includes determining the focal plane with a highest focus score for each image patch having each single candidate object.

26. The method of claim 25, further comprising selecting and outputting the respective focal planes with the highest focus score for each candidate object.

27. The method of claim 17, wherein determining attributes of each single candidate object in the focal plane having a best focus for each single candidate object includes determining one or more of an area, a roundness, a shape, or a grayscale intensity of each single candidate object in the focal plane having the best focus for each single candidate object and assigning one or more blobs having one or more of the area, the roundness, the shape, or the grayscale intensity as a candidate object of interest.

28. The method of claim 17, further comprising outputting one or more determined attributes of each single candidate object in the focal plane having the best focus for each single candidate object and classifying each single candidate object as an artifact or candidate object based on the one or more determined attributes.

29. The method of claim 17, further comprising:
  filtering the one or more candidate objects based at least in part on a score that is based at least in part on one or more characteristics thereof and outputting one or more color-corrected image patches and one or more adaptive grayscale intensity image patches for each filtered candidate object;
  extracting one or more feature vectors from the color-corrected image patches and the adaptive grayscale intensity image patches and outputting the one or more feature vectors;
  classifying each feature vector as corresponding to an artifact or an analyte; and
  determining if the feature vectors classified as analytes are above or below a threshold level associated with a positive diagnosis.

30. The method of claim 17, wherein the method is carried out using at least one memory storage medium that includes each of an image preprocessing module, a candidate object detection module, a feature extraction module, a classification module, and a diagnosis module stored therein as computer readable programs that are executable by at least one processor operably coupled to the at least one memory storage medium.

31. The method of claim 30, wherein the candidate object detection module includes a candidate object cluster detection module, a candidate object clustering module, a best focus detection module, a candidate object cluster attribute extraction module, an artifact filtering module, and a thumbnail extraction module.

32. The method of claim 31, wherein the candidate object cluster detection module includes a threshold determination submodule and a blob identification submodule configured to identify candidate object clusters having a grayscale intensity that differs from a threshold grayscale intensity.

33. The method of claim 17, wherein applying a white balance transform includes determining the white balance transform including:
  selecting a plurality of brightest pixels from a subset of the plurality of images randomly selected such that a probability of a presence of a clear pixel therein is substantially 1;
  calculating and applying a standard grayscale intensity of each pixel of the subset of the plurality of images to determine the plurality of brightest pixels in each of the subset of the plurality of images;
  determining a red value R, a green value G, and a blue value B of each of the plurality of brightest pixels;

calculating an average color vector defined by an average color of the plurality of brightest pixels;
determining a white color vector;
determining an axis vector that is perpendicular to, and calculated from a cross-product of, both the average color vector and the white color vector; and
determining an affine transform matrix calculated from the axis vector and an angle between the average color vector and the white color vector.

34. The method of claim 29, wherein applying an adaptive grayscale transform to the plurality of images includes outputting a plurality of adaptive grayscale intensity images.

35. The method of claim 34, wherein applying an adaptive grayscale transform includes:
receiving as input a plurality of color-corrected images and standard grayscale intensity images;
thresholding the standard grayscale intensity images at a dark threshold to detect one or more blobs;
filtering at least one of color, area, or shape of the detected one or more blobs to locate and identify white blood cell nuclei at high sensitivity and specificity;
outputting as white blood cell vector data a red value R, a green value G, and a blue value B of one or more pixels from the color-corrected images that contain a white blood cell nuclei therein;
outputting as background vector data, a red value R, a green value G, and a blue value B of a plurality of qualified background pixels as determined from a random sampling of pixels that are brighter in grayscale intensity than the dark threshold in the color-corrected images; and
determining an adaptive grayscale projection vector from the white blood cell vector data and background vector data.

36. The method of claim 34, wherein applying an adaptive grayscale transform includes determining and applying an adaptive grayscale projection vector using a plurality of white blood cell pixels, a plurality of qualified background pixels, and a regression.

37. The method of claim 29, wherein filtering each single candidate object based at least in part on one or more determined attributes includes determining a threshold score based upon attributes of ground truth objects trained into a memory storage medium and accessed by at least one processor.

38. The method of claim 29, wherein classifying each feature vector as corresponding to an artifact or an analyte includes receiving as input one or more feature vectors of candidate objects and classifying the one or more feature vectors as corresponding to one of the artifact or the analyte.

39. The method of claim 38, wherein classifying each feature vector as corresponding to an artifact or an analyte includes using a machine learning classifier that outputs a score indicating that each of the one or more feature vectors of the one or more candidate objects corresponds to an analyte.

40. The method of claim 29, further comprising accepting as ground truth one or more annotated images of the analyte in ground truth samples and one or more annotated images of artifacts in ground truth samples.

41. The method of claim 40, wherein accepting as ground truth one or more annotated images of the analyte in ground truth samples and one or more annotated images of artifacts in ground truth samples includes teaching a machine learning classifier a set of weights based at least in part on one or more learned ground truth sample image patches.

42. The method of claim 41, wherein the machine learning classifier includes a convolutional neural network and teaching the machine learning classifier a set of weights based at least in part on the one or more ground truth sample image patches includes loading the one or more annotated images of the analyte in ground truth samples and the one or more annotated images of artifacts in ground truth samples into the convolutional neural network.

43. The method of claim 42, wherein teaching the machine learning classifier a set of weights based at least in part on the one or more ground truth sample image patches includes augmenting the one or more ground truth sample image patches using a data augmentation scheme.

44. The method of claim 43, wherein the data augmentation scheme includes a random gamma correction of one or more of a red, green, blue, or grayscale intensity component of the one or more ground truth sample image patches.

45. The method of claim 29, further comprising identifying a species of one or more candidate objects based at least in part on one or more image characteristics including one or more of shape, size, or color of the one or more candidate objects.

46. The method of claim 29, wherein the analyte includes a parasite.

47. The method of claim 29, further comprising recording, with a microscope, one or more images of one or more sample slides.

48. A method for determining a presence of an analyte in blood, the method comprising:
receiving a plurality of images of a sample slide, the plurality of images including,
a plurality of fields-of-view, each including a unique x and y coordinate of the sample slide; and
a plurality of focal planes, each having a unique z coordinate of the sample slide;
applying a white balance transform to each of the plurality of images effective to produce a plurality of color-corrected images; and
applying an adaptive grayscale transform to each of the plurality of images to provide adaptive grayscale intensity images for each of the plurality of images;
detecting and identifying one or more candidate objects in the plurality of color-corrected images and the adaptive grayscale intensity images, including,
performing an adaptive thresholding operation on the adaptive grayscale intensity images and outputting one or more candidate object clusters based thereon, including,
receiving one or more adaptive grayscale intensity images and receiving a white blood cell detection mask that includes information about locations of white blood cells in the plurality of fields-of-view and plurality of focal planes;
determining a local adaptive threshold of grayscale intensity for one or more regions in the adaptive grayscale intensity images using the one or more adaptive grayscale intensity images and white blood cell detection mask, including,
determining the local adaptive threshold for at least some windows of a plurality of windows in the plurality of fields-of-view and plurality of focal planes in the adaptive grayscale images, including at least some windows containing one or more candidate objects therein, by locally estimating a noise floor of the at least some of the windows by determining a median grayscale intensity value in each of the at least some windows in the adaptive grayscale intensity images, discounting any variations in the median grayscale intensity value due to presence of white blood cells;

wherein determining a median grayscale intensity value in each of the at least some windows in the adaptive grayscale intensity images includes:

receiving information noting a presence and location of white blood cells within one or more identified windows of a field-of-view of the plurality of fields-of-view;

when a white blood cell is indicated as present, replacing pixels containing the white blood cell in a specific region of the one or more identified windows of the field-of-view with a replacement median grayscale intensity value determined from all pixels in the field-of-view;

determining a local median grayscale intensity value for all pixels in each of the one or more identified windows after white blood cell containing pixels have been replaced by the replacement median grayscale intensity value; and outputting the local adaptive threshold for each of the one or more identified windows based on the local median grayscale intensity value therein associating clusters of detected candidate objects indicating that one or more adjacent candidate objects are a single candidate object and outputting the locations of the clusters of one or more adjacent candidate objects, the locations including one or more image patches containing the one or more adjacent candidate objects;

identifying the focal plane having a best focus for each single candidate object;

determining attributes of each single candidate object in the focal plane having the best focus for each single candidate object;

filtering each single candidate object based at least in part on one or more determined attributes; and extracting and outputting one or more image patches each containing at least one filtered single candidate object of the one or more candidate objects, filtering the one or more candidate objects based at least in part on a score that is based at least in part on one or more characteristics thereof and outputting one or more color-corrected image patches and one or more adaptive grayscale intensity image patches for each filtered single candidate object;

extracting one or more feature vectors from the color-corrected image patches and the adaptive grayscale intensity image patches and outputting the one or more feature vectors;

classifying each feature vector as corresponding to an artifact or an analyte; and determining if the feature vectors classified as analytes are above or below a threshold level associated with a positive diagnosis.

* * * * *

UNITED STATES PATENT AND TRADEMARK OFFICE
CERTIFICATE OF CORRECTION

| | | |
|---|---|---|
| PATENT NO. | : 10,061,972 B2 | Page 1 of 1 |
| APPLICATION NO. | : 15/433656 | |
| DATED | : August 28, 2018 | |
| INVENTOR(S) | : Cary Richard Champlin et al. | |

It is certified that error appears in the above-identified patent and that said Letters Patent is hereby corrected as shown below:

In the Specification

Column 1, Line 35:
"MICROSCOPY AND MACHINE LEARING FOR" should read --MICROSCOPY AND MACHINE LEARNING FOR--

In the Claims

Column 57, Claim 12, Line 45:
"based at least in part on one or more determined attribute." should read --based at least in part on one or more determined attributes.--

Signed and Sealed this
Twentieth Day of November, 2018

Andrei Iancu
*Director of the United States Patent and Trademark Office*